(12) United States Patent
Hanao et al.

(10) Patent No.: US 7,855,314 B2
(45) Date of Patent: *Dec. 21, 2010

(54) ABSORBER AND ABSORBENT ARTICLE

(75) Inventors: Hiroyuki Hanao, Shikokuchuo (JP);
Taira Kubo, Shikokuchuo (JP);
Yoshiharu Miyashita, Shikokuchuo (JP); Tomotsugu Matsui, Shikokuchuo (JP); Akinori Fukae, Shikokuchuo (JP); Toshikazu Maeda, Shikokuchuo (JP); Hiroyuki Yano, Shikokuchuo (JP); Takeshi Furudoi, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 552 days.

This patent is subject to a terminal disclaimer.

(21) Appl. No.: 11/630,914

(22) PCT Filed: Jun. 28, 2005

(86) PCT No.: PCT/JP2005/011863

§ 371 (c)(1),
(2), (4) Date: Sep. 24, 2007

(87) PCT Pub. No.: WO2006/006395

PCT Pub. Date: Jan. 19, 2006

(65) Prior Publication Data

US 2009/0004435 A1 Jan. 1, 2009

(30) Foreign Application Priority Data

| Jun. 28, 2004 | (JP) | 2004-190411 |
| Jun. 30, 2004 | (JP) | 2004-194851 |
| Jun. 30, 2004 | (JP) | 2004-194852 |
| Jun. 30, 2004 | (JP) | 2004-194854 |
| Nov. 25, 2004 | (JP) | 2004-340951 |
| Nov. 29, 2004 | (JP) | 2004-344715 |
| Feb. 8, 2005 | (JP) | 2005-031662 |
| Mar. 31, 2005 | (JP) | 2005-103856 |

(51) Int. Cl.
*A61F 13/15* (2006.01)
(52) U.S. Cl. .................. 604/358; 604/385.101; 442/417; 428/156
(58) Field of Classification Search ............ 604/375, 604/385.101, 385.19, 383; 442/417; 428/156
See application file for complete search history.

(56) References Cited

U.S. PATENT DOCUMENTS

| 6,646,180 | B1 | 11/2003 | Chmielewski | |
| 6,660,902 | B2 | 12/2003 | Widlund et al. | |
| 2003/0212376 | A1* | 11/2003 | Walter et al. | 604/358 |
| 2004/0138634 | A1* | 7/2004 | Litvay et al. | 604/374 |
| 2004/0204696 | A1* | 10/2004 | Chen | 604/367 |
| 2008/0038504 | A1* | 2/2008 | Manabe et al. | 428/71 |
| 2008/0044616 | A1* | 2/2008 | Hanao et al. | 428/68 |
| 2008/0262459 | A1* | 10/2008 | Kamoto et al. | 604/375 |

FOREIGN PATENT DOCUMENTS

| CN | 2258390 | 7/1997 |
| CN | 1342446 | 4/2002 |
| CN | 1372451 | 10/2002 |
| CN | 1507336 | 6/2004 |
| JP | H1-285265 | 11/1989 |
| JP | H04-504285 | 7/1992 |
| JP | H6-509399 | 10/1994 |
| JP | 3025258 | 6/1996 |
| JP | H10-118113 | 5/1998 |
| JP | H10-168230 | 6/1998 |
| JP | H11-081116 | 3/1999 |
| JP | 2000-015093 | 1/2000 |
| JP | 2001-316902 | 11/2000 |
| JP | 2000-333992 | 12/2000 |
| JP | 2001-214399 | 8/2001 |
| JP | 2001-524350 | 12/2001 |
| JP | 2002-65743 | 3/2002 |
| JP | 2002-509764 | 4/2002 |
| JP | 2002-282304 | 10/2002 |
| JP | 2003-33397 | 2/2003 |
| JP | 2003-033398 | 2/2003 |
| JP | 2003-70820 | 3/2003 |
| JP | 2003-088555 | 3/2003 |
| JP | 2003-88555 | 3/2003 |
| JP | 2003-144489 | 5/2003 |
| JP | 2003-190210 | 7/2003 |
| JP | 2003-192732 | 7/2003 |
| JP | 2004-41339 | 2/2004 |
| WO | WO 2004/017883 | 3/2004 |

* cited by examiner

*Primary Examiner*—Arti Singh-Pandey
(74) *Attorney, Agent, or Firm*—DLA Piper LLP (US)

(57) ABSTRACT

An Absorber and an absorbent article including a fiber aggregate wherein a tow composed of fibers is used as the fiber aggregate, and the compression resilience RC is 45 to 60%. Also, the fiber aggregate has a density of 0.0075 g/cm$^3$ or less, weight of 0.0075 g/cm$^2$ or less and a mass of 1 to 15 grams.

3 Claims, 50 Drawing Sheets

Fig. 36
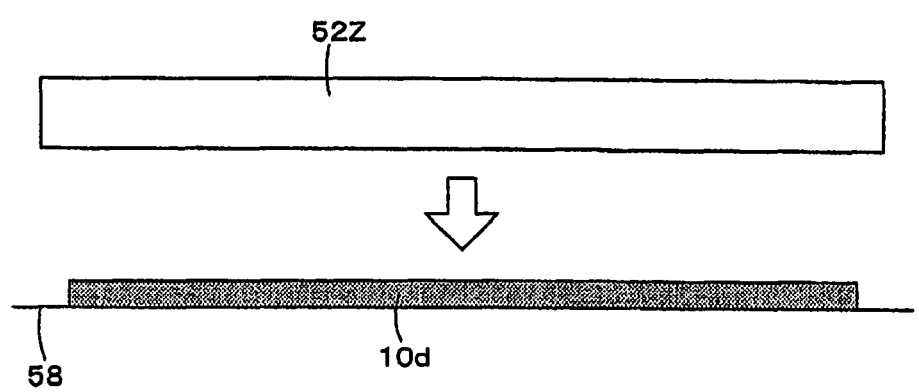
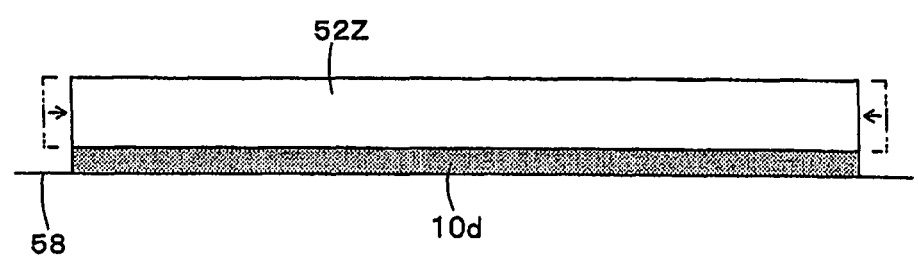

ABSORBER AND ABSORBENT ARTICLE

BACKGROUND OF THE INVENTION

1. Field of the Invention

The present invention relates to absorbent article such as paper diaper and sanitary napkin, and to absorbers used for such absorbent article.

2. Prior Art

Absorbers imbedded in absorbent article of body fluid have been generally ones that super absorbent polymer particles are dispersed and held in air formed core of short fiber pulp. Such absorbent article of body fluid are sold in plastic wrapping, particularly in a paper diaper field, they are packed in a compressed state to accommodate as many body absorbent article in a package as possible or to enable them to be delivered in a compact state. On the occasion of use, necessary pieces are taken out from the package. In this way, absorbent article of body fluid are relieved from the compressed state.

In the above conventional absorbers, however, there has been room to be improved on resilience in relieving the compressed state. When resilience of absorber is not good, it is not preferable because desired absorption performance cannot be exhibited, otherwise, sense of anxiety about absorption performance arises in users.

To solve the problems, there is proposed a solution that special resilient members called cushion material or foam material are attached on absorbent article of body fluid (see, e.g. Patent reference 1), in this case, there has been a problem that an increase in weight, thickness or costs is involved therein.

patent document 1 Japanese Unexamined Patent Application Publication 2000-316902.

SUMMARY OF THE INVENTION

Therefore, a primary object of the present invention is to improve resilience from a packing state without increasing weight, thickness or costs.

The present invention that has solved the problems is as follows:

An absorber comprising a fiber aggregate, wherein a tow composed of fibers is used as the fiber aggregate, and the compression resilience RC is 45 to 60%.

The absorber described above, wherein the compression energy WC based on KES test is 4.0 to 7.0 gf·cm/cm$^2$.

The absorber described above, wherein the fiber density is 0.0075 g/cm$^3$ or less when the thickness of the fiber aggregate is set to 10 mm.

The absorber described above, wherein the basis weight of the fiber aggregate is 0.0075 g/cm$^2$ or less.

The absorber described above, wherein the mass of the fiber aggregate is 1 to 15 g.

The absorber described above, wherein the planar projection area of the absorber is 400 cm$^2$ or more, and the thickness is 0.1 to 1 cm.

Absorptive goods wherein the absorber described above is disposed between a top sheet and a back surface sheet.

The absorbent article described above, wherein a holding sheet is disposed on the back surface side of the absorber.

The absorbent article described above, wherein the holding sheet has a compression energy WC based on KES test of 0.01 to 10.00 gf·cm/cm$^2$ and is a non-woven fabric with compression resilience of 10 to 100%.

The absorbent article described above, wherein the constituent fiber of the fiber aggregate composed of tow is cellulose acetate fiber.

MAIN EFFECT OF THE INVENTION (I) An absorber itself has sufficient resilience when it employs a specific "fiber aggregate composed of tow" with compression resilience of 45 to 60%. Accordingly; no use of special resilient member is required, so that resilience from a packing state can be improved without increasing weight, thickness, or costs.

(2) When the compression energy WC based on KES test is 4.0 to 7.0 gf·cm/cm$^2$, packing can be compressed as compactly as conventional level, or more compactly.

(3) Depending on fineness and material of fiber aggregate, bonding level of fibers one another, but in general case, the fiber density of 0.0075 g/cm$^3$ or less when the thickness is set to 10 mm is advantageous in resilience and ease of compression.

(4) Depending on fineness and material of fiber aggregate, bonding level of fibers one another, but in general case, basis weight of 0.0075 g/cm$^2$ or less is advantageous in the points of resilience, ease of compression, increase in weight and costs.

(5) Even if the mass of fiber aggregate exceeds 15 g, there are effects due to no use of special resilient member, and suppressing effects against weight increase and costs as well. However, in such high weight, influence of the mass of special resilient members to a total mass becomes small, thus significance to construct an absorber by using a specific fiber aggregate with high resilience becomes small. Therefore, the mass of fiber aggregate is preferably less than 15 g from this point.

(6) When the plan project area is 400 cm$^2$ or more, and the thickness of the absorber is 0.1 to 1 cm, by the characteristic constitution of the above respective inventions, it is very advantageous for improving resilience without increasing weight, thickness and costs.

(7) In the case where super absorbent polymer particles are included in a fiber aggregate formed by opening tows, when back surface side of a product is touched, concave-convex clump of SAP particles fallen from fiber aggregate or in lower part of fiber aggregate yields shingly uncomfortable feeling, lowering the product value. In contrast, in the case where a holding sheet is disposed in back surface side of absorber, such shingly uncomfortable feeling when touched from back surface side of product is reduced or not generated.

Based on the present invention, it becomes possible to improve resilience from a packing state without increasing weight, thickness or costs.

BRIEF DESCRIPTION OF THE DRAWINGS

FIG. 36 is a schematic diagram showing an adhesive application example to sheet.

DETAILED DESCRIPTION OF THE INVENTION

An embodiment of the present invention will be described in detail with reference to paper diapers and the production equipment thereof shown in the attached drawings below.

Figure 1:
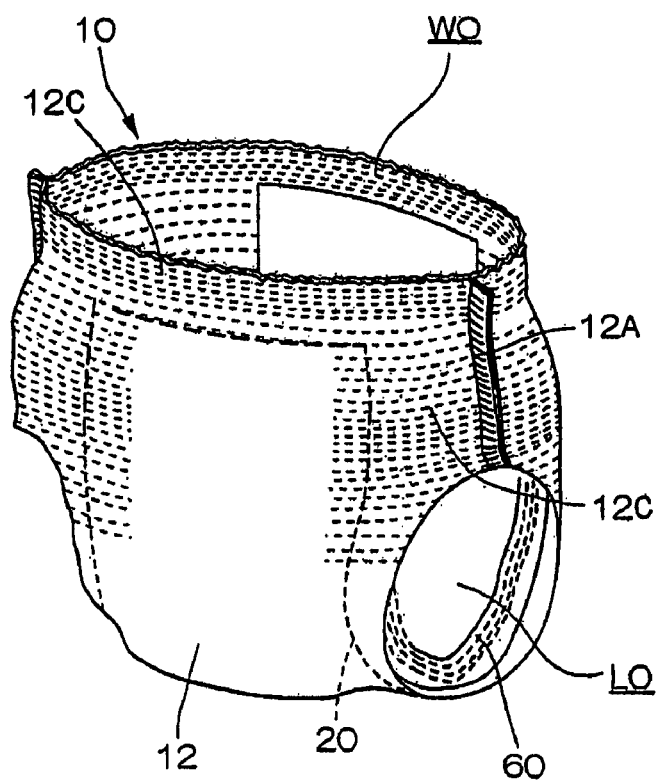
FIG. 1 is a perspective view of underpants type diaper.

FIG. 1 shows an example of underpants-type disposable diaper. This underpants type disposable diaper 10 is provided with an external sheet 12 of outer face (rear face) side and an aborptive body 20 of inner face (front face) side, and the absorptive body 20 is fixed with the external sheet 12. The absorptive body 20 is a part to receive body fluids such as urine and soft shit (menstrual blood in sanitary napkin described below), adsorb and maintain them. The external sheet 12 is a part to wear a wearer.

The external sheet 12 is shaped like a sand clock as shown in the figure for example, the both sides are narrowed for a wearer to put legs. The absorptive body 20 can shape any form, in the figure, it is rectangular.

Figure 2:
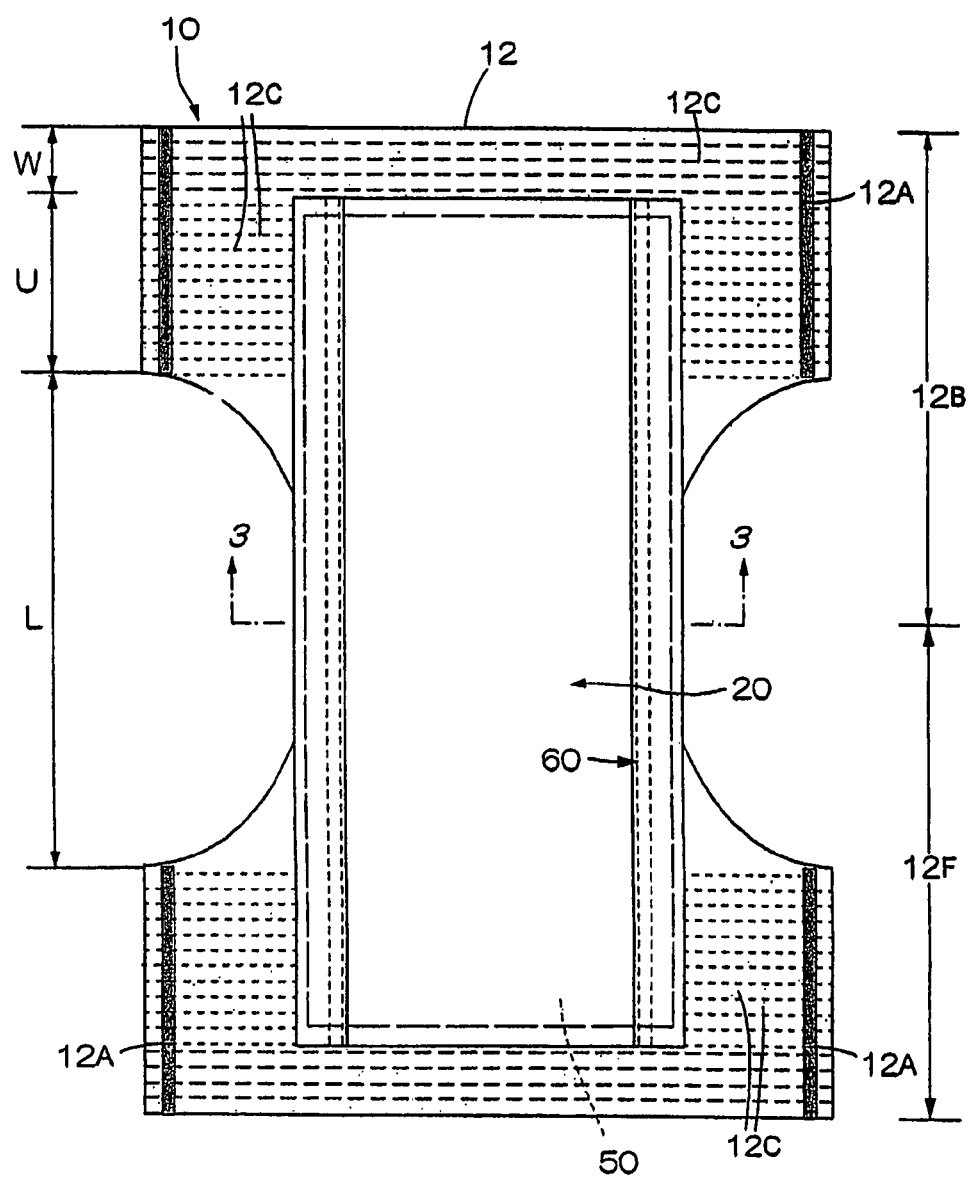
FIG. 2 is a plan view of underpants type diaper in a development state.

As shown in FIG. 2, the external sheet 12 is folded back and forth after the absorptive body 20 is set and fixed in a given place, a bonding region 12A is bonded by thermal bonding at both sides of a front body 12F and a back body 12B in the external sheet 12. In this way, an underpants-type disposable diaper is obtained having a waist opening WO and a pair of leg openings LO in a structure shown in FIG. 1.

The width in the middle of absorptive body 20 shown in the figure in the longitudinal direction (namely in the up and down direction in FIG. 2, also, back and forth direction of product) is shown as in a shape shorter than the width fastening the narrow part of external sheet 12. This relationship of width may be reverse or may be the same width.

The external sheet 12 is desirably constructed with two pieces of water repellent non-woven sheets for example, a shape is desirable such that an elastic member is interposed between these sheets to fit a wearer by the contractive force. As the elastic member, rubber thread and strip material like elastic foam can be used, use of many rubber threads is preferable. In the mode shown in the figure, rubber threads 12C are continuously provided in the width direction in a waist region W, they are provided only in both sides in a hip region U, and not provided in a crotch region L. Since the rubber threads 12C are provided in the waist region W and hip region U, even if rubber thread 12 itself is weak in compressive force, a product fits well to a wearer because they touch a wearer in hip region U as a whole.

Figure 3:
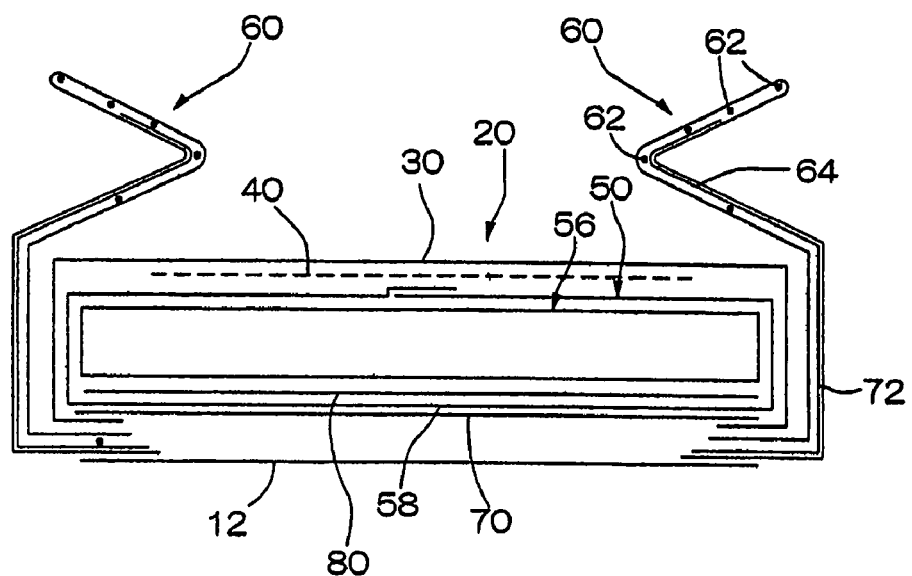
FIG. 3 is a plan view of underpants type diaper in a development state.

As shown in FIG. 3, an absorptive body 20 in an embodiment is provided with a top sheet 30 composed of non-woven fabric permeating body fluids for example, a medium sheet (second sheet) 40 and an absorber 50 including an absorbent core 56. Also, at the back surface side of absorber 50, a body liquid impermeable sheet (also called back sheet) 70 composed of plastic sheet etc. In the back surface side of this body fluid impermeable sheet 70. An external sheet 12 is provided. Further, barrier cuffs 60 are provided.

A top sheet 30 has a property permeating body fluids. Thus, material for the top sheet 30 is any one exhibiting permeability, for example, porous or nonporous non-woven fabric and porous plastic sheet can be listed. Also, fiber material of non-woven fabric is not particularly limited. For example, there can be exemplified synthetic fibers such as olefin type like polyethylene and polypropylene, polyester type and polyamide type; regenerated fibers such as rayon and cupra; natural fibers such as cotton; and mixed fibers used in 2 or more kinds thereof. Further, non-woven fabric may be produced in any processing. As the processing method, for example, there can be listed known methods such as spun lace method, spun bond method, thermal bond method, melt blown method and needle punch method. For example, spun lace method is a preferable processing method for flexibility and drape property, and thermal bond method is a preferable processing method for bulkiness and softness.

Also, the top sheet 30 may be constructed of one sheet, or a laminated sheet consisting of two or more sheets. Similarly, the top sheet 30 may consist of one sheet or, two or more sheets in regard to the plane direction.

To transport body fluids passed through top sheet 30 quickly, a medium sheet 40 ordinarily called "second sheet" whose permeation velocity is faster than that of top sheet 30 can be disposed. This medium sheet can not only make body fluids transport into an absorber quickly to enhance absorption performance by an absorber but also prevent "flow back" of body fluids from the absorber once absorbed to always keep a dry state on the top sheet 30.

Figure 20:
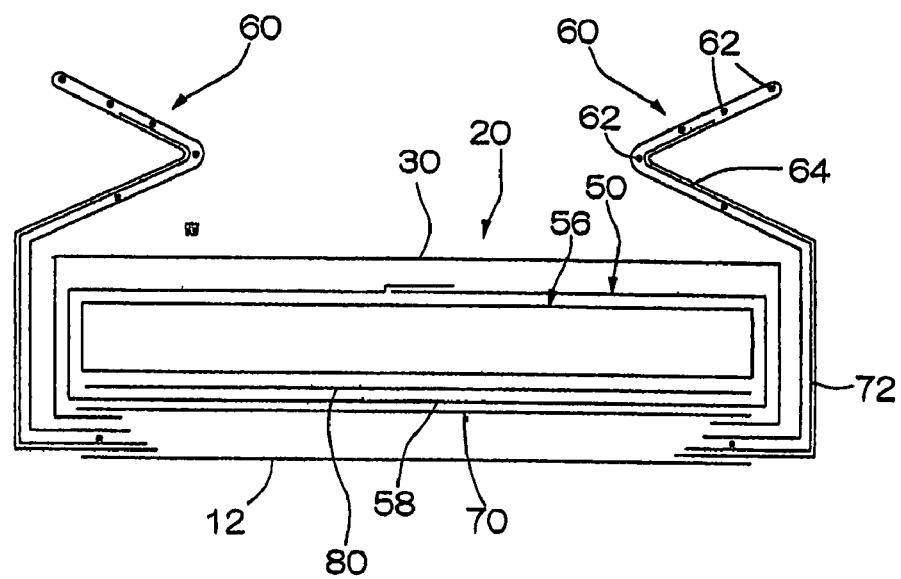
FIG. 20 is a sectional view showing other mode of absorber.

The medium sheet (second sheet) 40 is interposed between the top sheet 30 and wrapping sheet 58. A mode without disposing medium sheet (second sheet) 40 can be also used as shown in FIG. 20.

The medium sheet 40 shown in the figure is shorter than an absorbent core 56 and disposed in the middle, may be disposed in the entire width. The length of medium sheet 40 in the longitudinal direction may be the same as the absorbent core 56 or in a range of shorter length centered in a region of receiving body fluids. A typical material of medium sheet 40 is non-woven fabric having excellent permeability of body fluid.

As the medium sheet 40, there can be exemplified the same material as the top sheet 30, spun lace, non-woven pulp, mixed sheet of pulp and rayon, point bond or crepe paper. In particular, air-through non-woven fabric and spun bond non-woven are preferred.

An elastic degree of medium sheet in the length direction of a product is preferably 0.05 to 0.75 g·cm2/cm to reduce or not to generate shingly uncomfortable feeling when touched from the surface side of a product. Herein, "elastic degree in the length direction of product" means a value obtained in such manner that a cut sample of 200 mm long and 200 mm wide is bent in DEF sensitivity of 20, in a range of curvature radius of 0.0 cm$^{-1}$ to 0.5 cm$^{-1}$, using a single bending tester (KES-FB2 manufactured by Kato Tech Co. Ltd.). This is the same as in a wrapping sheet.

The absorber 50 comprises an absorbent core 56 having a fiber aggregate of opened tow, super absorbent polymer particles and a wrapping sheet 58 for wrapping at least rear face and side face of this absorbent core 56. Further, a holding sheet 80 is disposed between the absorbent core 56 and rear face side (under part) of wrapping sheet 58.

Figure 4:
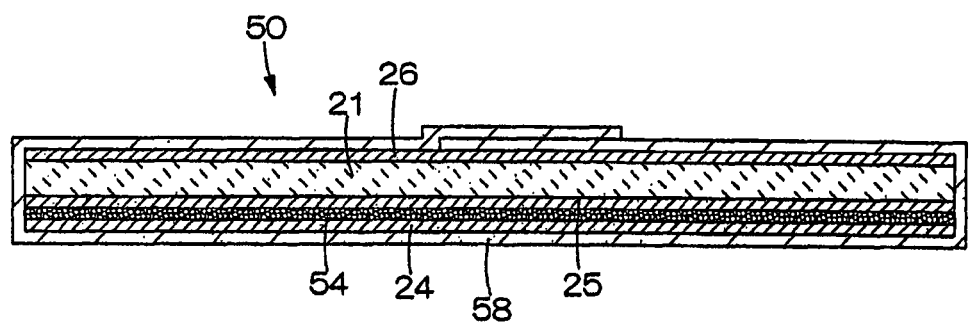
FIG. 4 is a sectional view showing a first mode of absorber.

First mode of absorber is shown in FIG. 4, this absorber 50 comprises an absorbent core 56 having a fiber aggregate 21, an absorptive polymer particles 54, and a wrapping sheet 58 for wrapping at least rear face and side face of the absorbent core 56, an adhesive 24 is applied continuously on the entire surface or almost entire surface of parts providing at least super absorbent polymer particles in the wrapping sheet 58. Additionally, "almost entire surface" means 80% of parts providing super absorbent polymer particles More specifically, a layer composed of super absorbent polymer particles 54 is provided with a adhesive 24 on the inner face of wrapping sheet 58, on which a layer composed of fiber aggregate 21 is further provided with adhesive 25, further, on the fiber aggregate 21, a wrapping sheet 58 is bonded with adhesive 26. The wrapping sheet 58 in the illustrative example is folded in both sides, so that it is constructed for the fiber aggregate 21 and super absorbent polymer particle 54 to be wrapped, a mode that wrapping is done by tucking two sheets up and down can be adopted. As this wrapping sheet 58, absorptive sheets such as crepe paper and non-woven fabric are preferably used as described below.

Also, not shown in figures, the following construction can be realized: on the entire surface or almost entire surface of parts providing at least high adsorptive polymer particles in the wrapping sheet 58, the part applied with adhesive and a plurality of parts having no adhesive being surrounded by the part applied with adhesive are provided, there are super absorbent polymer particles bonded on the wrapping sheet 58 by the part applied with adhesive and high adsorptive polymer particles present in the parts having no adhesive.

In the case where the adhesive 24 is applied in a continuous face, curtain coating and roll coating can be used. Also, in the case of providing the part applied with adhesive and a plurality of parts having no adhesive being surrounded by the part applied with adhesive, spiral coating can be used. As the adhesive 24, thermoplastic resins used as binders for fiber aggregate described below can be preferably employed.

In the first example of absorber, most of super absorbent polymer particles 54 are thermally bonded on the wrapping sheet 58 by the adhesive 24 or, part of super absorbent polymer particles 54 is bonded on the wrapping sheet 58 by the adhesive 24, in addition thereto, most of super absorbent polymer particles 54 are confined in a closed space with no adhesive being surrounded by the part applied with adhesive. Also, part or all of super absorbent polymer particles 54 are bonded on the fiber aggregate 21 by the adhesive 25. Therefore, shingly hand feeling and unintentional deviation of absorption characteristics can be effectively prevented. Additionally, symbol 26 shows an adhesive for bonding the opposite face of the polymer side of fiber aggregate 21 and the wrapping sheet 58.

Figure 5:
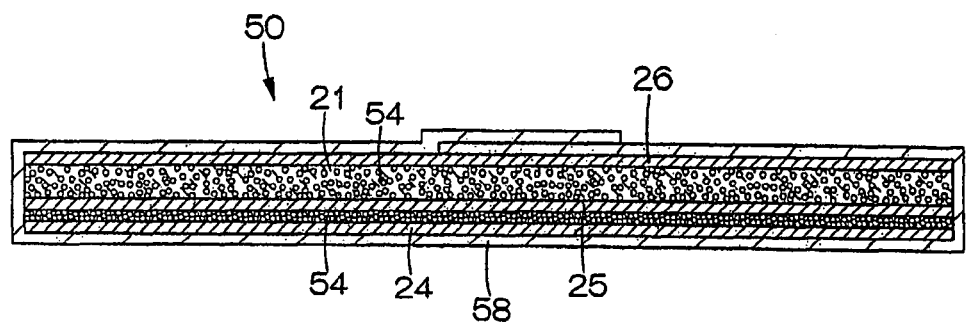
FIG. 5 is a sectional view showing a second mode of absorber.

A second mode of absorbent is shown in FIG. 5, it is different from the first mode in such point that the super absorbent polymer particles 54 are also kept in the fiber aggregate 21.

Figure 6:
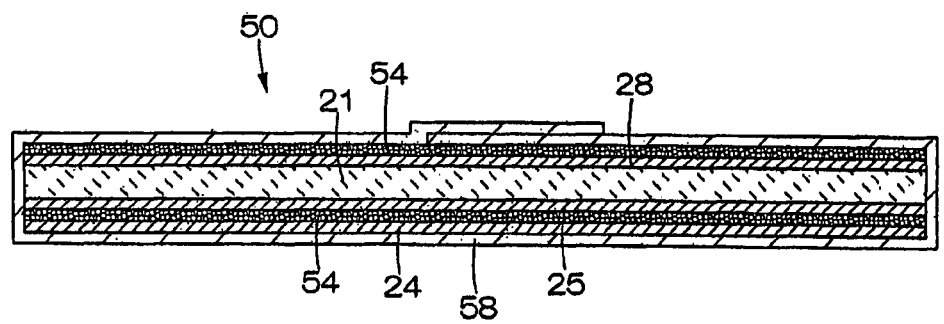
FIG. 6 is a sectional view showing a third mode of absorber.

A third mode of absorber is shown in FIG. 6, it is different from the first mode where the super absorbent polymer particles 54 are provided only in one side (under side) of fiber aggregate 21 in such point that the super absorbent polymer particles 54 are each provided on both up and down sides of fiber aggregate 21. In this case, the super absorbent polymer particles 54 positioned on the upper side of fiber aggregate 21 can be bonded on the fiber aggregated 21 by the adhesive 28.

Figure 7:
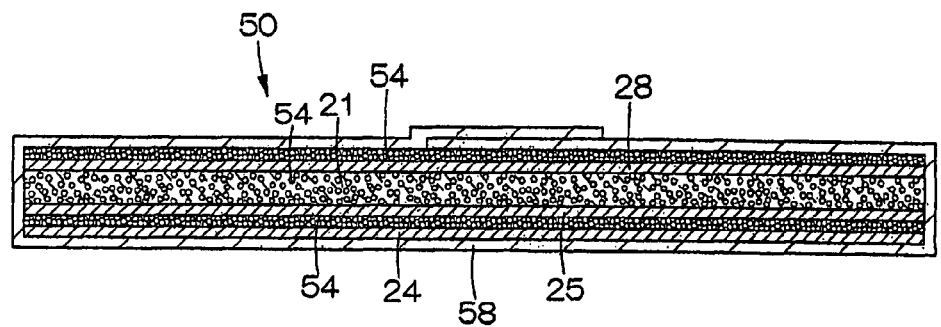
FIG. 7 is a sectional view showing a fourth mode of absorber.

A fourth mode of absorber is shown in FIG. 7, it is a mode where the super absorbent polymer particles 54 are also kept in the fiber aggregate 21, which is further the same manner as the second mode in the third mode.

Figure 8:
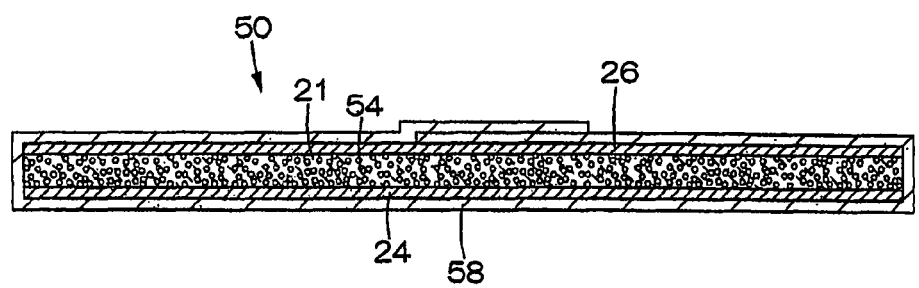
FIG. 8 is a sectional view showing a fifth mode of absorber.

A fifth mode of absorber is shown in FIG. 8, it is a mode where the super absorbent polymer particles 54 bonded on the wrapping sheet 58 and its adhesive 25 in the second mode are not used, super absorbent polymer particles 54 are kept only in the fiber aggregate 21.

Figure 9:
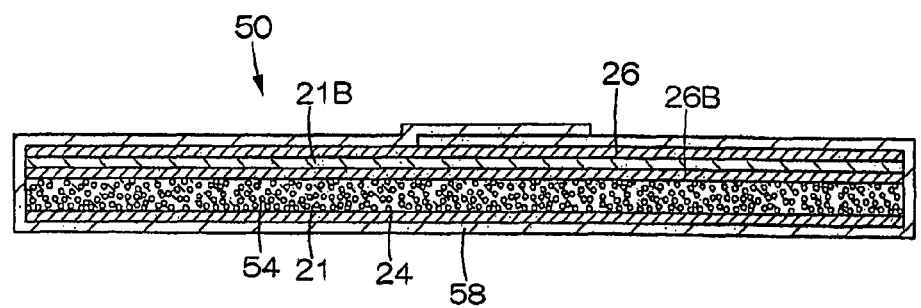
FIG. 9 is a sectional view showing a sixth mode of absorber.

A sixth mode of absorber is shown in FIG. 9, it is a mode where, in the fifth mode, a layer 21B of a fiber aggregate alone (not holding the super absorbent polymer particles 54) is provided on the fiber aggregate 21 holding the super absorbent polymer particles 54, and the fiber aggregate 21 holding the super absorbent polymer particles 54 and the layer 21B of fiber aggregate alone are bonded with the adhesive 26B.

Figure 10:
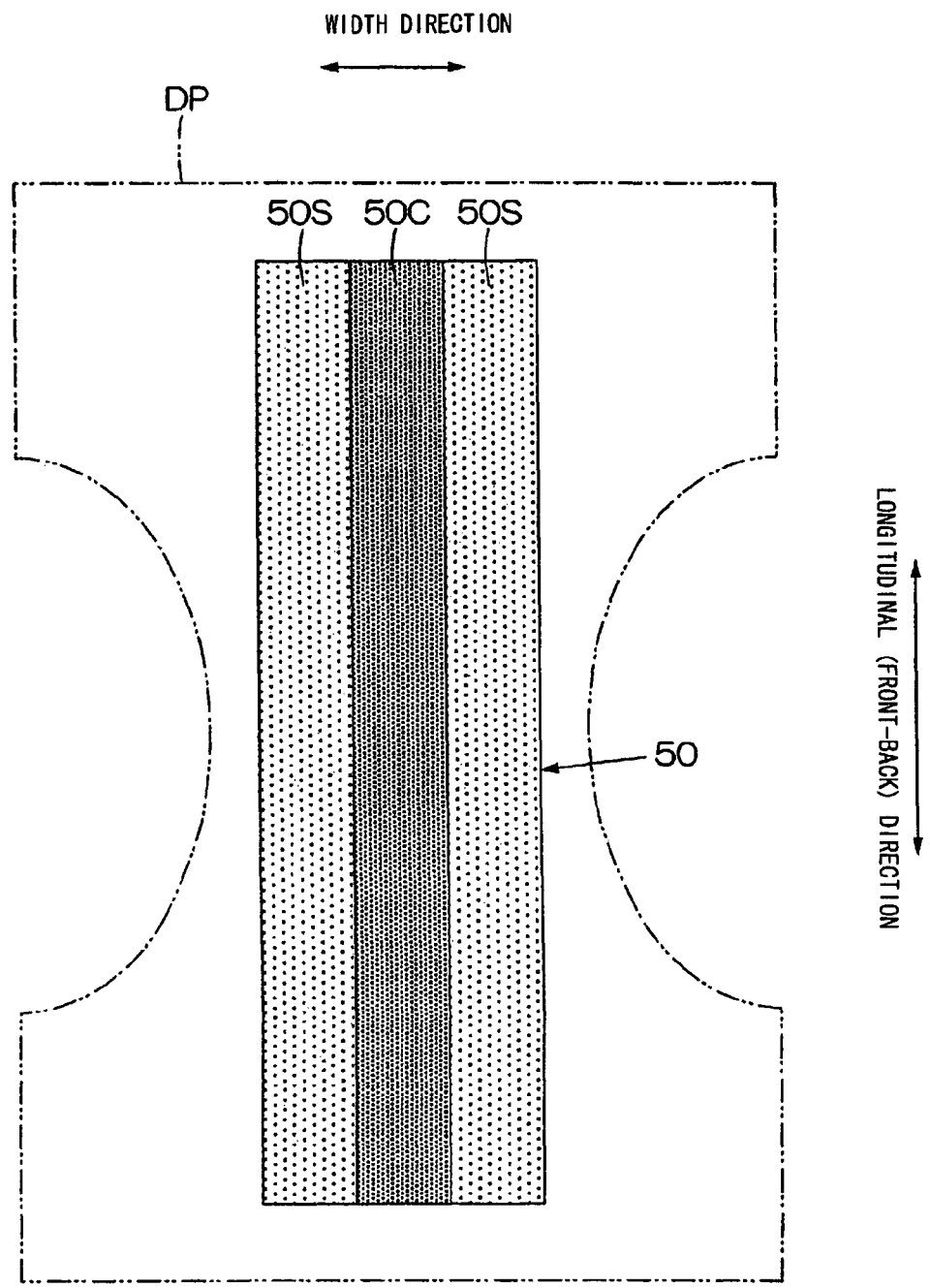
FIG. 10 is a plan view showing a seventh mode of absorber.
Figure 11:
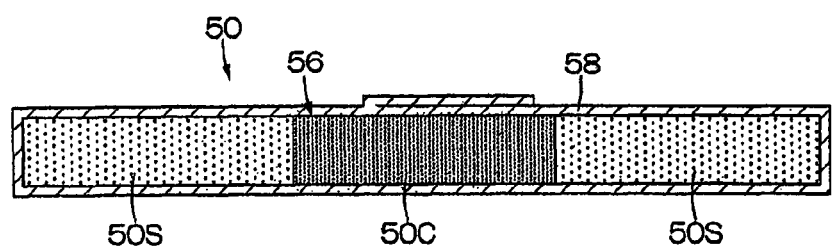
FIG. 11 is a sectional view showing a seventh mode of absorber.

A sixth mode of absorber 50 is shown in FIG. 10 and FIG. 11. This absorber 50 comprises a fiber aggregate of tow composed of fibers, an absorbent core 56 containing super absorbent polymer particles and the wrapping sheet 58 for wrapping them, is characterized in that relatively high and low content parts of super absorbent polymer particles are provided. The high and low contents are shown by dense and sparse points in the figures. By the above construction, particularly, the amount of absorption among absorption characteristics can be intentionally biased.

As the example shown in the figures, it is a preferable mode that the amount of super absorbent polymer particles in the middle in the width direction of fiber aggregate 50C is larger than the amount of super absorbent polymer particles in both sides in the longitudinal direction of fiber aggregate 50S. In this case, when it is used to the width direction in the absorbent article (the example shown in the figures is paper diaper DP), absorption amount in the middle in the width direction 50C supplied with more body fluids can be more maintained.

Figure 12:
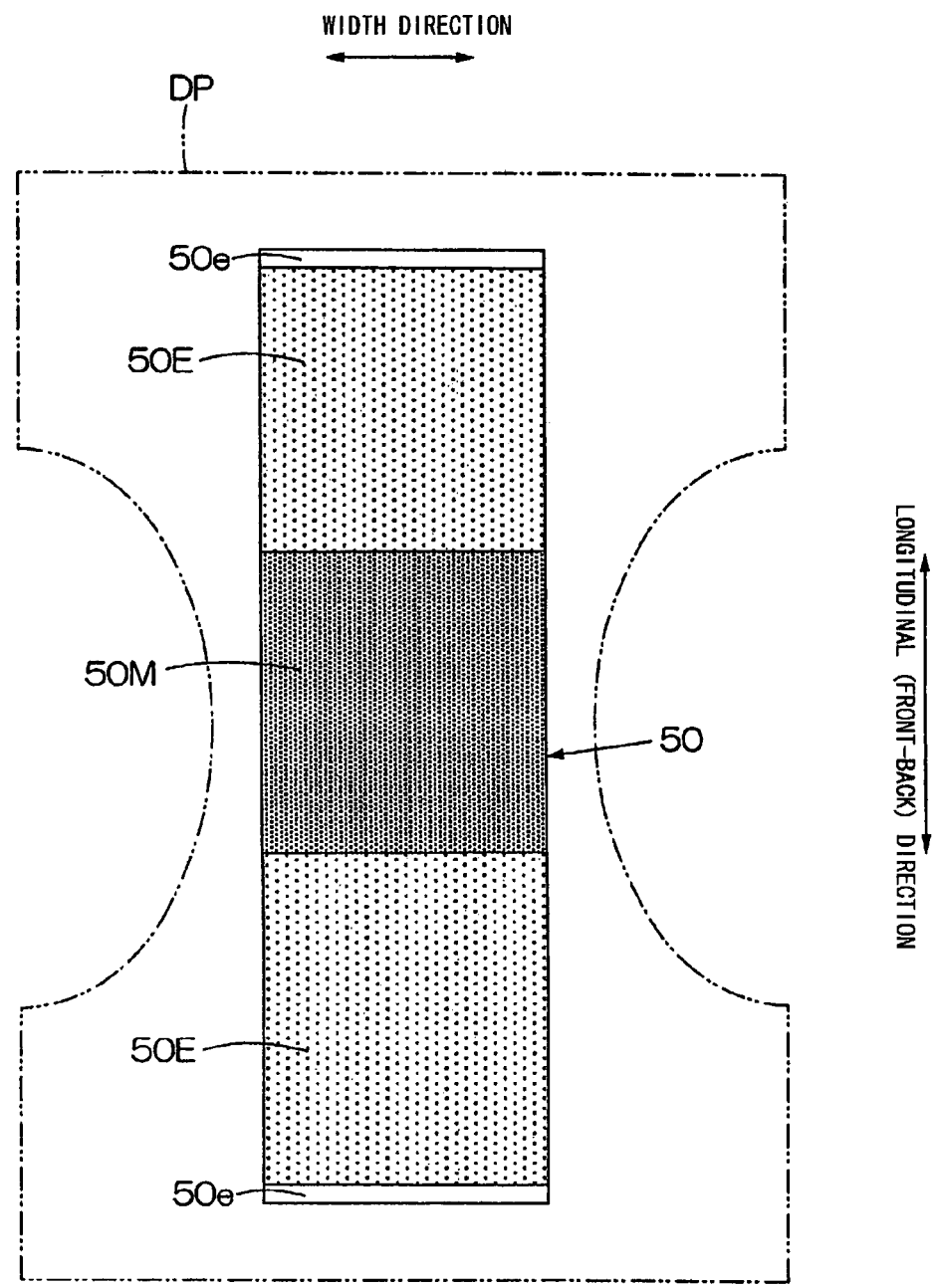
FIG. 12 is a plan view showing a seventh mode of absorber.

As shown in FIG. 12, it is also preferable mode that the amount of super absorbent polymer particles in the middle in the longitudinal direction of fiber aggregate 50 M is larger than the amount of super absorbent polymer particles in back and forth in the longitudinal direction of fiber aggregate 50E. In this case, when it is used to the longitudinal direction in the absorbent article (the example shown in the figures is paper diaper DP), absorption amount in the middle in the longitudinal direction 50M supplied with more fluids can be more maintained.

It is also a preferable mode that the super absorbent polymer particles are not provided in a cut part 50e at both ends in the longitudinal direction. It can prevent cuter blade from suffering short life in production. This mode can be produced in such way that the application amount of super absorbent polymer particles is set in three levels (large, small, none), and a cycle of small-large-small-none is repeated.

On the other hand, depending on the circumstances, the amount of super absorbent polymer particles at both ends in the longitudinal direction of fiber aggregate 50E can be larger than the amount of super absorbent polymer particles in the middle in the longitudinal direction of fiber aggregate 50M. Also, in the example in the figure, there are divided into three sections of the middle and both sides in the longitudinal direction of absorber 50, the amount of super absorbent polymer particles can be differentiated each other by separating into two or, four or more, also, the amount of super absorbent polymer particles can be changed continuously in the longitudinal direction of absorber 50.

In absorber 50, super absorbent polymer particles may be held in a fiber aggregate, on the surface of fiber aggregate, or in both. Furthermore, super absorbent polymer particles may be held partly on the surface of fiber aggregate and may be held entirely in a fiber aggregate.

Figure 13:
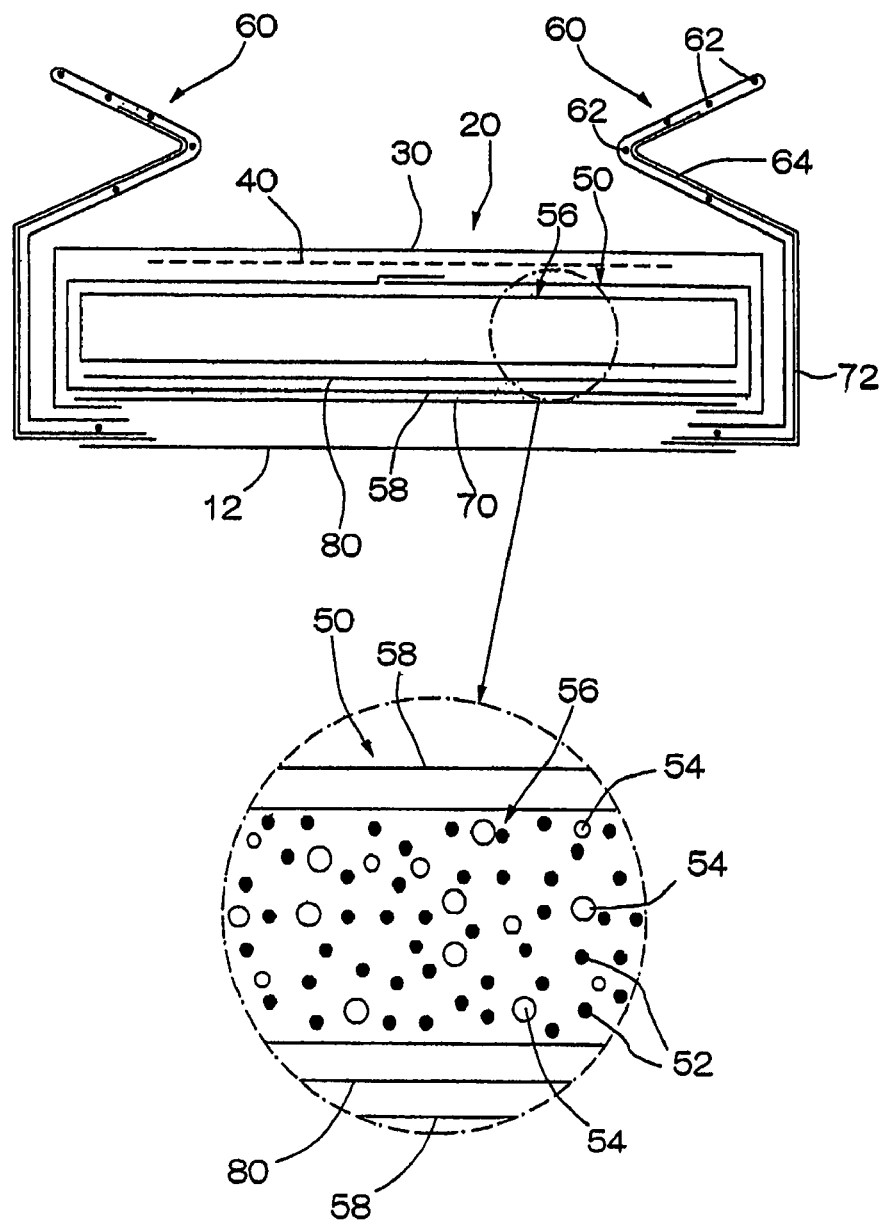
FIG. 13 is a sectional view showing a seventh mode of absorber.

However, at least in a region receiving body fluids, it is desirable for a fiber aggregate that super absorbent polymer particles (SAP particles) are dispersed essentially in the whole thickness direction. A state dispersed essentially in the whole thickness direction is schematically shown in FIG. 13 as an enlarged view of essential part. Additionally, symbol 52 in FIG. 13 shows a constituent fiber (filament) of fiber aggregate.

Figure 14:
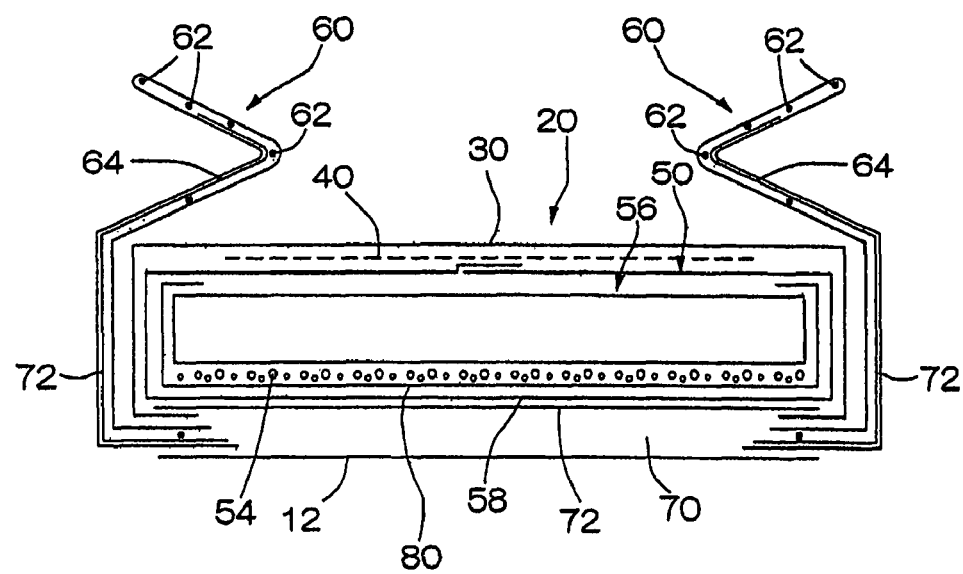
FIG. 14 is a sectional view showing a seventh mode of absorber.

The case where there is no SAP particle in the upper, under and middle parts of absorbent core 56 can be hardly said that it is "dispersed wholly in the thickness direction." Therefore, "dispersed wholly in the thickness direction" means a mode where it is "uniformly" dispersed wholly in the thickness direction for a fiber aggregate, in addition thereto includes a mode where it is biased in upper, under and middle parts, still dispersed in each part of upper, under and middle parts. Also, there is no exclusion of modes where parts of SAP particles do not enter into a fiber aggregate, but stay on the surface; parts of SAP particles pass through a fiber aggregate and are present on the wrapping sheet 58; and they are present on the holding sheet 80 as shown in FIG. 14. Additionally, in the case where gel blocking is not concerned, they may be biased only in the upper part or only in the middle part, in the case where back flow is not concerned, they may be biased only in the middle part or only in the under part.

This seventh mode relates to at least one direction of width direction, longitudinal direction and thickness direction of a product, although the amount of super absorbent polymer particles in each part (hereinafter called dispersion density) is large or small, relates to all directions of width direction, longitudinal direction and thickness direction of a product as another mode, a mode where the amount of super absorbent polymer particles is uniform can be adopted.

Figure 15:
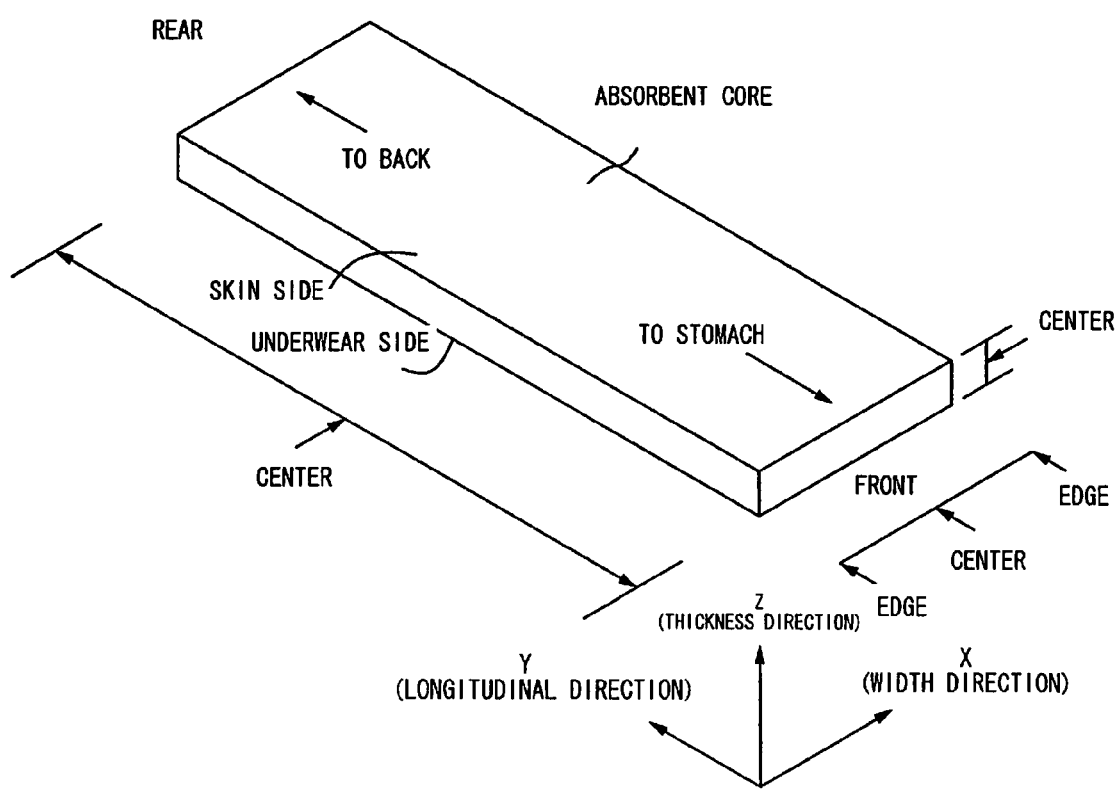
FIG. 15 is a brief overview explaining the directions of absorber.

Summary of a mode "dispersion density of super absorbent polymer particles being large and small" is as follows. As shown in FIG. 15, in regard to absorbent core 56, when the width direction of a product is X, the longitudinal direction is Y, and the thickness direction is Z, as shown in Table 1, the case where dispersion density of super absorbent polymer particles in one region is enlarged (enhanced) more than that in other region is defined as "bias", the case where dispersion density of super absorbent polymer particles is the same is defined as "uniformity", specific effect of each mode is shown in Table 2 through Table 4. Needless to say, a combination of each condition can be used.

TABLE 1

| | | | | |
|---|---|---|---|---|
| X(width direction) | Near to center | Uniform | Near to edge | |
| Y(longitudinal direction) | Near to stomach | Near to center | Uniform | Near to back |
| Z(thickness direction) | Near to center | Uniform | Skin side | Underwear side |

TABLE 2

In respect of X direction, when "near to center", SAP can be provided efficiently at necessary sites, thus enabling manufacturing at low costs, as well as SAP loss at the time of manufacturing is less.

| X | Y | Z | Characteristic advantages | |
|---|---|---|---|---|
| Near to center | Near to stomach | Near to center | Advantageous for boys, less SAP discomfort. | (1) |
| | | Uniform | Advantageous for boys, good balance of absorption performance. | (2) |
| | | Skin side | Advantageous for boys, almost no back flow. | (3) |
| | | Underwear side | Advantageous for boys, high absorption speed. | (4) |

TABLE 2-continued

In respect of X direction, when "near to center", SAP can be provided efficiently at necessary sites, thus enabling manufacturing at low costs, as well as SAP loss at the time of manufacturing is less.

| X | Y | Z | Characteristic advantages | |
|---|---|---|---|---|
| | Near to center | Near to center | Advantageous for girls, less SAP discomfort. | (5) |
| | | Uniform | Advantageous for girls, good balance of absorption performance. | (6) |
| | | Skin side | Advantageous for girls, almost no back flow. | (7) |
| | | Underwear side | Advantageous for girls, high absorption speed. | (8) |
| | Uniform | Near to center | Advantageous for both boys and girls, less SAP discomfort. | (9) |
| | | Uniform | Advantageous for both boys and girls, good balance of absorption performance. | (10) |
| | | Skin side | Advantageous for both boys and girls, almost no back flow. | (11) |
| | | Underwear side | Advantageous for both boys and girls, high absorption speed. | (12) |
| | Near to back | Near to center | Advantageous for few month-old-babies e.g., newborn babies, less SAP discomfort. | (13) |
| | | Uniform | Advantageous for few month-old-babies e.g., newborn babies, good balance of absorption performance. | (14) |
| | | Skin side | Advantageous for few month-old-babies e.g., newborn babies, almost no back flow. | (15) |
| | | Underwear side | Advantageous for few month-old-babies e.g., newborn babies, high absorption speed. | (16) |

TABLE 3

In respect of X direction, when "uniform", discomfort with SAP is reduced, and less SAP movement in use is achieved.

| X | Y | Z | Characteristic advantages | |
|---|---|---|---|---|
| Uniform | Near to stomach | Near to center | Advantageous for boys, less SAP discomfort. | (17) |
| | | Uniform | Advantageous for boys, good balance of absorption performance. | (18) |
| | | Skin side | Advantageous for boys, almost no back flow. | (19) |
| | | Underwear side | Advantageous for boys, high absorption speed. | (20) |
| | Near to center | Near to center | Advantageous for girls, less SAP discomfort. | (21) |
| | | Uniform | Advantageous for girls, good balance of absorption performance. | (22) |
| | | Skin side | Advantageous for girls, almost no back flow. | (23) |
| | | Underwear side | Advantageous for girls, high absorption speed. | (24) |
| | Uniform | Near to center | Advantageous for both boys and girls, less SAP discomfort. | (25) |
| | | Uniform | — | (26) |
| | | Skin side | Advantageous for both boys and girls, almost no back flow. | (27) |
| | | Underwear side | — | (28) |
| | Near to back | Near to center | Advantageous for few month-old-babies e.g., newborn babies, less SAP discomfort. | (29) |
| | | Uniform | Advantageous for few month-old-babies e.g., newborn babies, good balance of absorption performance. | (30) |
| | | Skin side | Advantageous for few month-old-babies e.g., newborn babies, almost no back flow. | (31) |
| | | Underwear side | Advantageous for few month-old-babies e.g., newborn babies, high absorption speed. | (32) |

TABLE 4

In respect of X direction, when "near to edge", it is advantageous for the reduction in leakage around legs or from sides. In particular, it is superior for use with an inner pad.

| X | Y | Z | Characteristic advantages | |
|---|---|---|---|---|
| Near to edge | Near to stomach | Near to center | Advantageous for boys, less SAP discomfort. | (33) |
| | | Uniform | Advantageous for boys, good balance of absorption performance. | (34) |
| | | Skin side | Advantageous for boys, almost no back flow. | (35) |
| | | Underwear side | Advantageous for boys, high absorption speed. | (36) |
| | Near to center | Near to center | Advantageous for girls, less SAP discomfort. | (37) |
| | | Uniform | Advantageous for girls, good balance of absorption performance. | (38) |
| | | Skin side | Advantageous for girls, almost no back flow. | (39) |
| | | Underwear side | Advantageous for girls, high absorption speed. | (40) |
| | Uniform | Near to center | Advantageous for both boys and girls, less SAP discomfort. | (41) |
| | | Uniform | Advantageous for both boys and girls, good balance of absorption performance. | (42) |
| | | Skin side | Advantageous for both boys and girls, almost no back flow. | (43) |
| | | Underwear side | Advantageous for both boys and girls, high absorption speed. | (44) |
| | Near to back | Near to center | Advantageous for few month-old-babies e.g., newborn babies, less SAP discomfort. | (45) |
| | | Uniform | Advantageous for few month-old-babies e.g., | (46) |

TABLE 4-continued

In respect of X direction, when "near to edge", it is advantageous for the reduction in leakage around legs or from sides. In particular, it is superior for use with an inner pad.

| X | Y | Z | Characteristic advantages | |
|---|---|---|---|---|
| | | Skin side | newborn babies, good balance of absorption performance. Advantageous for few month-old-babies e.g., newborn babies, almost no back flow. | (47) |
| | | Underwear side | Advantageous for few month-old-babies e.g., newborn babies, high absorption speed. | (48) |

Figure 16:
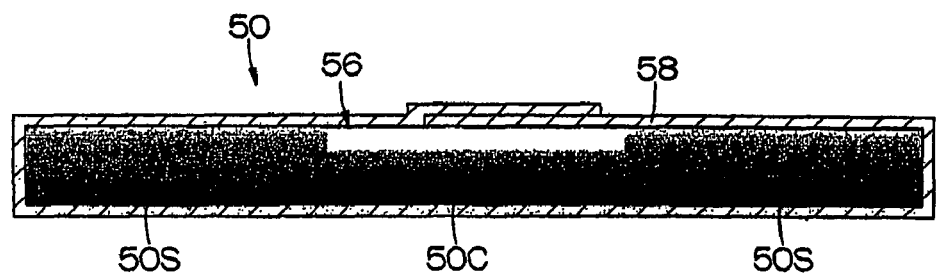
FIG. 16 is a sectional view showing an eighth mode of absorber.

Next, FIG. 16 shows an eighth mode of absorber. This absorber 50 comprises the absorbent core 56 containing a fiber aggregate and super absorbent polymer particles and the wrapping sheet 58 for wrapping them, is characterized in that relatively high part and low part in density of super absorbent polymer particles in the fiber aggregate are provided. High and low of this density are shown as gradation in the figure. In this way, by setting relatively high part and low part in density of super absorbent polymer particles in the fiber aggregate, particularly absorption speed among absorption characteristics can be intentionally biased.

In particular, as the example in the figure, it is a preferable mode that the density of super absorbent polymer particles in the middle in the width direction 50C is set to be higher than that in both sides in the width direction 50S. In this case, the absorption characteristic is that the absorption speed in the middle in the width direction 50C is slow, whereas the absorption speed in both sides in the width direction 50S is fast. Thus, when it is used to the width direction of absorbent article, more fluids are supplied to the middle in the longitudinal direction in the middle in the width direction 50C, from which, diffused well into periphery to utilize a wider area for absorption, in addition thereto, so-called transverse leakage can be prevented because of high absorption speed in both sides in the width direction 50S.

Figure 17:
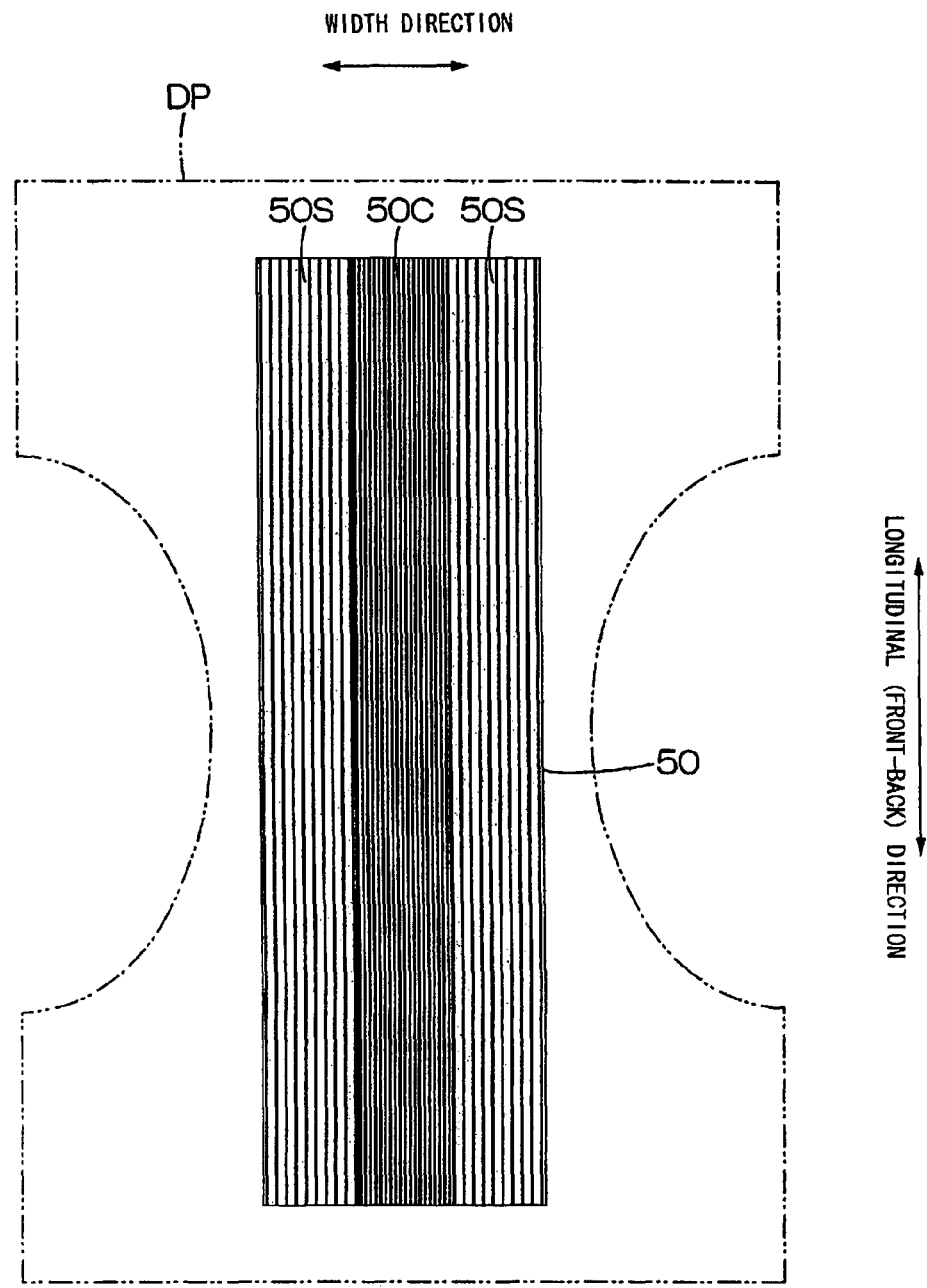
FIG. 17 is a sectional view showing a ninth mode of absorber.

Next, FIG. 17 shows a ninth mode of absorber. This absorber 50 comprises the absorbent core 56 containing a fiber aggregate and super absorbent polymer particles, and the wrapping sheet 58 for wrapping them, is characterized in that relatively high part and low part in fiber density of fiber aggregate are provided. High and low of this fiber density are shown as dense and sparse of lines in the figure. A fiber aggregate composed of tow has a property that liquid diffuses in the continuous direction of fiber, the tendency becomes prominent as the density becomes high. Thus, by setting relatively high part and low part in fiber density of fiber aggregate, absorption characteristics of absorber 50 can be intentionally biased.

The high and low of fiber density can be achieved by bias opening such as partly strong opening in production of fiber aggregate, or by partly using a plurality of piled tows.

In particular, as the example shown in the figure, it is a preferable mode that the fiber density of the middle in the width direction 50C is set to be higher than that of both sides in the width direction 50S. A fiber aggregate is excellent in upholding of body fluid when fiber density is low, on the other hand, it is excellent in diffusion of body fluid when fiber density is high. Accordingly, by setting such density difference, body fluids diffuses quickly in the middle in the width direction 50C, upholding of body fluid is improved in both sides in the width direction 50S where quick diffusion is not required, which imparts preferable characteristics to each region. More specifically, since diffusion of body fluid in the middle in the width direction 50C is higher than that in both sides in the width direction 50S, when it is used to the width direction of absorbent article of body fluid, body fluids easily diffuse in the middle in the width direction 50C where more fluids are supplied to utilize a wider area for absorption, in addition thereto, so-called transverse leakage is effectively prevented because fluids hardly diffuse in both sides in the width direction 50S.

However, regardless of how much difference of fiber density in the middle in the width direction 50C and both sides in the width direction 50S, the fiber density of both sides in the width direction 50S is preferably 10 to 100 g/m$^3$ more preferably 20 to 70 g/m$^3$, and particularly preferably 30 to 50 g/m$^3$. When the fiber density of both sides in the width direction 50S is too low, bias in the width direction of fiber aggregate could occur. On the other hand, when the fiber density in the ends of both sides is too high, it could give a wearer uncomfortable feeling.

In the case where absorber 50 is used in absorbent article, it may be used in either side as the side receiving body fluids, particularly in the first mode, it is preferably used in the fiber aggregate 21 side (upper side in the figure) as the side receiving body fluids.

Figure 18:
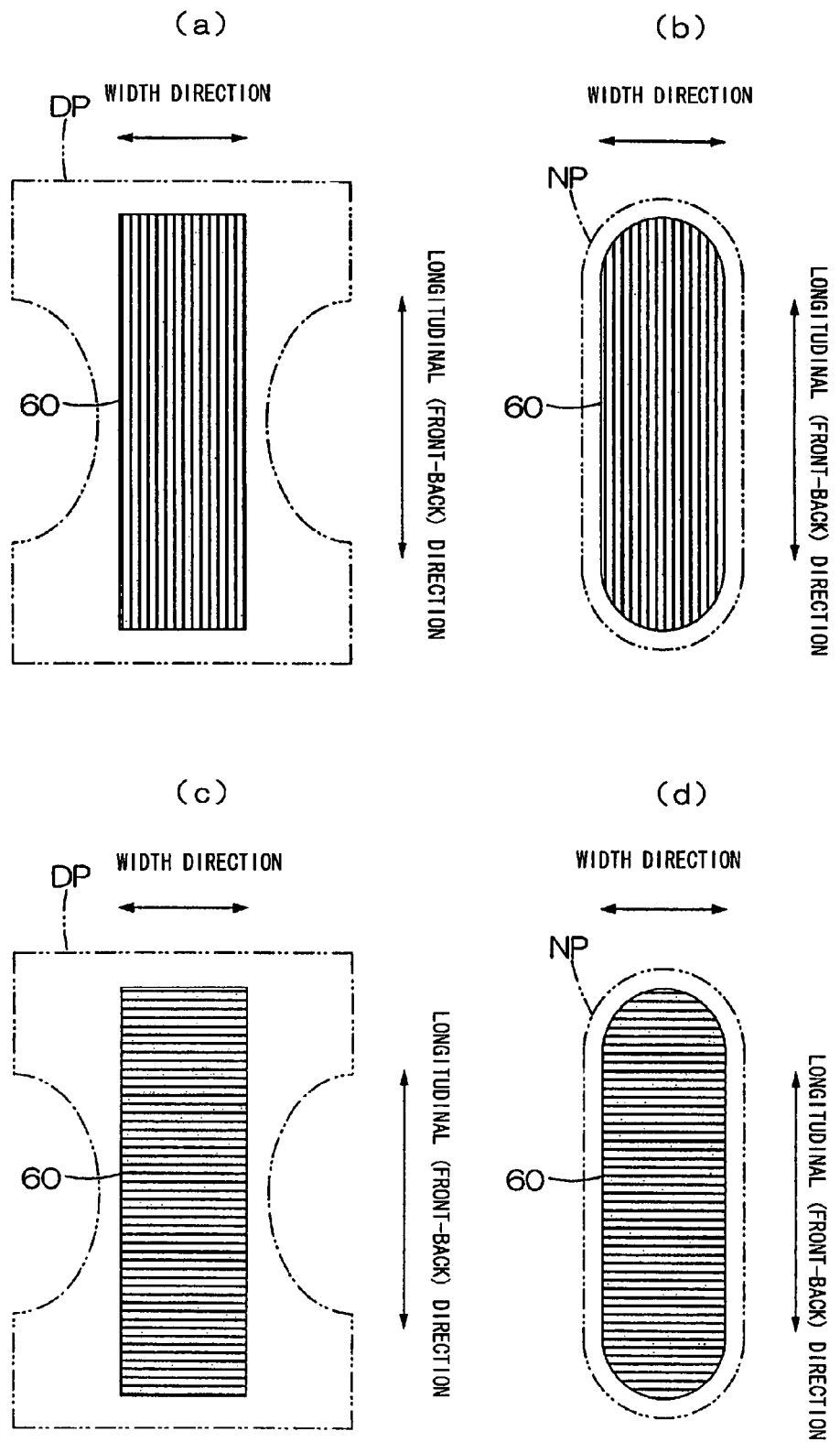
FIG. 18 is a plan view schematically showing the deposition of absorber.

Also, FIG. 18 shows a disposition example of absorber in paper diaper DP or sanitary napkin NP. A fiber aggregate of opened tow easily diffuses body fluids in the continuous direction (flow direction) of fiber, but has characteristic being difficult diffusion in the perpendicular direction to the continuous direction of fiber. Therefore, as shown in FIGS. 18 (a) and (b), it is preferable to dispose an absorber 60 so that the continuous direction of fiber (expressed by many lines) is the longitudinal direction (back and forth direction) of goods, but as shown in FIGS. 18 (c) and (d), it is possible to dispose it so that the continuous direction of fiber is the width direction of goods. When the continuous direction of fiber is the longitudinal direction of goods, fluids quickly diffuse to the longitudinal direction to utilize the entire surface of absorber 50 effectively.

A fiber aggregate is formed by opening a tow (fiber bundle) of bundle of filament essentially considered as a continuous fiber, namely, it is a filament aggregate. As a constituent fiber of tow, for example, there can be used polysaccharide and its derivatives such as cellulose, cellulose ester, chitin and chitosan, and synthetic polymers such as polyethylene, polypropylene, polyamide, polyester, polylactamide and polyvinyl acetate, cellulose ester and cellulose are particularly preferable.

As cellulose, there can be used cellulose derived from plant such as cotton, linter, wood pulp, and bacteria cellulose, regenerated cellulose like rayon may be used, regenerated cellulose may be a spun fiber.

As a preferable cellulose ester, for example, there can be used organic acid ester such as cellulose acetate, cellulose butyrate and cellulose propionate; mixed acid ester such as cellulose acetate propionate, cellulose acetate butyrate, cellulose acetate phthalate, and cellulose acetate nitrate; and cellulose ester derivatives such as polycaprolactone graft cellulose ester. These cellulose esters can be used alone or, in two or more kinds thereof. The viscosity average degree of polymerization in cellulose ester is, for example, 50 to 90, preferably about 200 to 800. The average degree of substitution in cellulose ester is, for example, about 1.5 to 3.0 (e.g. 2 to 3).

The average degree of polymerization in cellulose ester can be, for example, 10 to 1000, preferably 50 to 900, further preferably about 200 to 800, the average degree of substitution in cellulose ester can be, for example, about 1 to 3, preferably 1 to 2.15, and further preferably about 1.1 to 2.0. The average degree of substitution in cellulose ester can be selected from the points of higher biodegradation etc.

As a cellulose ester, organic acid ester (e.g. ester of organic acid having carbon atoms of about 2-4), cellulose acetate is particularly preferred. Acetylation degree of cellulose acetate is often about 43 to 62%, 30 to 50% is particularly preferable due to good biodegradation. Particularly preferable cellulose ester is cellulose diacetate.

Constituent fiber of tow may contain, for example, heat stabilizer, pigment, oil, yield improving agent, whiteness improving agent and the like.

Fineness of constituent fiber of tow can be, for example, 1 to 16 deniers, preferably 1 to 10 deniers, and further preferably about 2 to 8 deniers. Constituent fiber of tow may be non-crimped fiber, preferably crimped fiber. Degree of crimp of crimped fiber can be, for example, 5 to 75 pieces per one inch, more preferable 10 to 50 pieces, and further preferable about 15 to 50 pieces. Also, there are many cases that crimped fiber uniformly crimped is used. When crimped fiber is used, a bulky and light-weight absorbent core can be produced and also highly integrated tow can be easily produced by intertwine of fibers. Cross section of constituent fiber of tow is not particularly limited, for example, may be circular, elliptical, non-circular (e.g. Y-shape, X-shape, 1-shape, R-shape) or hollow shape. Constituent fiber of tow can be used in tow (fiber bundle) formed by bundling filaments of 3000 to 1000000 for example, preferably about 5000 to 1000000. It is preferable that fiber bundle is constructed by bundling continuous filaments of about 3000 to 1000000.

Tow is weak in intertwine of fibers, thus mainly to maintain the shape, binders capable of adhesion or thermally bonding operation at contact parts of fibers can be used. The binder can employ ester based plasticizers such as triacetin, triethylene glycol diacetate, triethylene glycol dipropionate, dibutyl phthalate, dimethoxyethyl phthalate and triethyl citrate, in addition thereto, may employ various resin adhesives, particularly thermoplastic resins.

As a thermoplastic resin for binder, it is a resin exhibiting adhesion force resulting from melting and solidification, including water insoluble or water hardly soluble resin, and water soluble resin. Water insoluble or water hardly soluble resin and water soluble resin can be in concomitant use according to need.

As a water insoluble or water hardly soluble resin that can be used, for example, there are listed olefin based homopolymer or copolymer such as polyethylene, polypropylene, ethylene-propylene copolymer and ethylene-vinyl acetate copolymer, polyvinyl acetate, acrylic resins such as polymethyl methacrylate, methyl methacrylate-acrylate copolymer, and (meth)acrylic monomer-styrene monomer copolymer; polyvinyl chloride, vinylacetate-vinylchloride copolymer, polystyrene, styrene based polymer such as copolymer of styrene type monomer with (meth)acrylic type monomer; polyesters that may be modified; polyamide such as nylon 11, nylon 12, nylon 610 and nylon 612; rosin derivatives (e.g. rosin ester); hydrocarbon resins (e.g. terpene resin, dicyclopentadiene resin, petroleum resin); hydrogenated hydrocarbon resin. These thermoplastic resins can be used alone or, in two or more kinds thereof.

As a water soluble resin that can be used, there are listed various water soluble polymers, for example, polyvinyl alcohol, polyvinyl pyrrolidone, polyvinyl ether, vinyl based water soluble resins such as copolymers of vinyl monomer with copolymerizable monomer having a carboxyl group, sulfonic group or their salts, acrylic based water soluble resin, polyalkylene oxide, water soluble polyester and water soluble polyamide. These water soluble resins may be used alone or, in combination of two or more kinds thereof.

The thermoplastic resin may be added with various additives such as stabilizers like antioxidant and ultraviolet absorbing agent, filler, plasticizer, antiseptic and fungus proofing agent.

However, it should be avoided to use a binder component preventing super absorbent polymer particles from infiltration as far as possible. It is the best way not to use a binder component preventing super absorbent polymer particles from infiltration.

Tow can be produced in known methods, so it will not be described in detail. Tow bale of cellulose diacetate that can be preferably used is commercially available from Celanese Corporation and Daicell Chemical Industries Ltd. Tow bale of cellulose diacetate has a density of about 0.5 g/cm$^3$, and has a total weight of 400-600 kg.

Tow is taken out from the bale, and open in a wide belt to be a desired size and bulkiness. The width of opened tow is arbitrary, for example, can be 100 to 2000 mm in width, preferably about 100 to 300 mm according to the width of absorbent core in a product. Also, the density of absorbent core can be adjusted by adjusting the degree of opening fibers.

A preferable fiber aggregate has a fiber density of 0.0075 g/cm$^3$ or less in the thickness of 10 mm, in particular, 0.0060 to 0.0070 g/cm$^3$. When the fiber density is too high, there becomes few merit in using a fiber aggregate formed by opening tow, for example, weight saving and reduction of thickness become difficult. Also, the base weight of fiber aggregate is 30 to 300 g/m$^2$, particularly preferably 30 to 90 g/m$^2$. The base weight of fiber can be adjusted by selecting tow for original fabric or by the production conditions.

As a method for opening tow, for example, there can be used a method that a tow is loaded to a plurality of opening rolls, in proceeding of tow, the width of tow is gradually enlarged, a method of opening tow by repeating strain (extension) and relaxation (construction) of tow, and a method of enlarging width/opening tow using a compressed air.

Highly absorptive polymer particle means inclusion of "power" in addition to "particle." The particle diameter of super absorbent polymer particle can employ one usable in this kind of absorbent article as it is, for example, preferably 20 to 850 μm. Specifically, super absorbent polymer particle having the following feature can be used.

Average particle diameter: about 350 μm

Distribution of Particle Size

850 μm on: 0%

500 μm on: 12.2%

250 μm on: 75.7%

180 μm on: 8.8%

106 μm on: 2.4%

106 μm pass: 0.9% primary particle diameter: 110-120 μm

Material of super absorbent polymer particle is not particularly limited for use, it is preferable to have an amount of water absorption of 50 g/g or more. As the super absorbent polymer particle, there can be used starch type, cellulosic and synthetic types, starch-acrylic acid (salt), graft copolymer, saponified starch-acrylonitrile copolymer, crosslinked sodium carboxymethyl cellulose and acrylic acid (salt) polymer. As a shape of super absorbent polymer particle, powder-particle usually used is preferable, but other shape can be also used.

Highly absorptive polymer particle having an absorption speed of 45 seconds or less can be preferably used. When the absorption speed exceeds 45 seconds, so-called flow back that body fluids supplied to an absorber flow back outside the absorber tends to occur.

Also, super absorbent polymer particle with gel strength of 900 Pa or more can be preferably used. Thereby, in the case of bulky absorbent core obtained by using tow, sticky feeling after absorption of body fluid can be effectively suppressed.

The base weight of super absorbent polymer particles can be suitably determined according to the amount required for applications of the absorber. Thus, being not categorically described, for example, it can be 400 g/m² or less. When the base amount of polymer is too low, absorption performance cannot be held, whereas it is too high, the effect is not only saturated but also the foregoing shingly uncomfortable feeling is given due to excess of super absorbent polymer particles.

According to need, super absorbent polymer particles can be adjusted in scattering density or application amount in the plane direction of absorbent core 56. For example, the application amount in an excretion region of body fluid can be increased more than other region. In the case of considering difference of man and woman, the scattering density (amount) can be increased in the front side for man, and the scattering density (amount) can be increased in the middle for woman. Also, a region with no presence of polymer can be disposed locally, like a spot for example, in the plane direction of absorbent core 56.

According to need, a plurality of different particle distributions of super absorbent polymer particles are prepared, which are sequentially scattered/projected in the thickness direction. For example, a plurality of scattering means 90 of super absorbent polymer particles described below are aligned at intervals in a line direction, firstly particles with smaller particle diameter distribution are scattered/projected, then particles with larger particle diameter distribution are scattered/projected, so that particles with smaller particle diameter distribution can be distributed in the underside and particles with larger particle diameter distribution can be disposed in the upper side of absorbent core 56. This mode is effective for particles with smaller particle diameter distribution to penetrate into a fiber aggregate deeply.

The ratio of super absorbent polymer particle and fiber aggregate determines absorption characteristics. As the weight ratio in a plane area of 5 cm×5 cm in a region directly receiving body fluid in the core 56, super absorbent polymer particle/filament in weight is desirably 1 to 14, particularly 3 to 9.

On the other hand, the size of absorbent core 56 is preferably a plan project area of 250 cm² or more and thickness of 0.5 to 10 mm, particularly preferably 1 to 5 mm. When the size of absorbent core is in this range, it is very advantageous for improvement of resilience without increasing weight, thickness and costs. Also, it is preferable that the mass of absorbent core is composed in 25 g or less, particularly preferably 10 to 20 g. When the mass of absorbent core is in this range, a merit of using no special member becomes remarkably prominent.

Compression resilience RC of absorbent core 56 is preferably 40 to 60%, particularly preferably 50 to 60%. Thereby, an absorbent core itself can exhibit sufficient resilience.

Further, when compression energy WC of absorbent core 56 is 4.0 to 10.0 gf·cm/cm², it is possible to be compressed compactly in the same level as conventional or more in packing.

These compression characteristics can be adjusted through the adjustment of fiber density of fiber aggregate by opening etc., selection of fiber material, selection of the kind of binder like plasticizer and the adjustment of degree of treatment thereof, or combinations thereof.

Herein, compression energy (WC) is an amount of energy consumption when a test piece cut in length of 200 mm and width of 50 mm is pushed at the center part up to 50 g (thickness of this case is used in Examples).

This compression energy can be measured by a handy compression tester (KES-G5 manufactured by Kato Tech Co., Ltd.). The conditions in using this tester are: SENS:2. the kind of pressure gauge: 1 kg, SPEED RANGE: STD, DEF sensitivity: 20. pressure area: 2 cm². input intervals: 0.1 (standard), STROKE SET: 5.0. upper limit load: 50 gf/cm²).

Moreover, compression resilience (RC) is a parameter expressing resilience when fiber is compressed. Therefore, compression resilience becomes large when resilience is good. This compression resilience can be measured by a handy compression tester (KES-G5 manufactured by Kato Tech Co., Ltd.). The conditions in using this tester are the same as the above compression energy.

As wrapping sheet 58, there can be used tissue paper, particularly crepe paper, non-woven fabric poly-laminated non-woven fabric, and a sheet with ostium opening holes. However, a sheet that super absorbent polymer particles cannot be slipped out is desirable. In the case of using non-woven fabric instead of crepe paper, hydrophilic non-woven fabric SMMS (spun bond/melt blown/melt blown/spun bond) is particularly preferable, the material can employ polypropylene, polyethylene/polypropylene, or the like. The base weight is desirably 8 to 20 g/m², particularly desirably 10 to 15 g/m².

Figure 19:
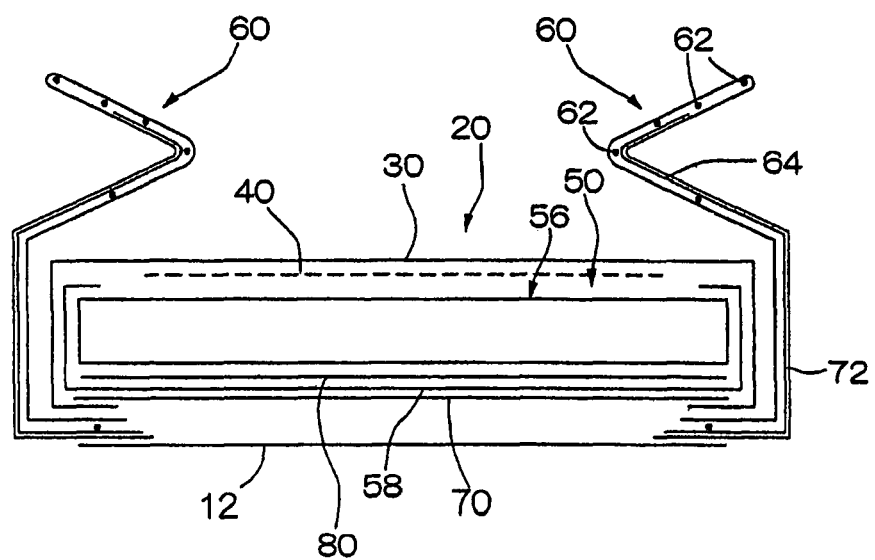
FIG. 19 is a sectional view showing another mode of absorber.

As shown in FIG. 3, it is a mode that this wrapping sheet 58 wraps a layer of fiber aggregate and super absorbent polymer particles 54 entirely, in addition thereto, for example as shown in FIG. 19, only the rear face and side face of the layer may be wrapped. Also, not shown in a figure, there may be a mode that only the upper surface and side face of absorbent core 56 are wrapped with crepe paper or non-woven fabric, the under surface is wrapped with a body fluid impermeable sheet such as polyethylene and a mode that only the upper surface of absorbent core 56 is wrapped with crepe paper or non-woven fabric, side face and under surface are wrapped with a body fluid impermeable sheet such as polyethylene (these respective materials become respective constituents of wrapping sheet). If necessary, there may be a case that a layer of fiber aggregate and super absorbent polymer particles 54 is tucked up and down with two sheets, and a case that it is disposed only in the under surface or the upper surface, but which is not a desirable mode because movement of super absorbent polymer particles can be hardly prevented.

Highly absorptive polymer particles 54 can be present by scattering them between a holding sheet 80 and an absorbent core 56. There are instances that super absorbent polymer particles 54 are passed through a fiber aggregate in scattering/projecting them on a fiber aggregate or in the following steps, or in distribution processes to use by consumers. The concavity and convexity of super absorbent polymer particles passed through a fiber aggregate give a shibly uncomfortable feeling when touched by hand in use by a consumer. Therefore, holding sheet 80 having upholding characteristic of super absorbent polymer particles is disposed between the absorbent core 56 and wrapping sheet 58. This holding sheet 80 reinforces elastic property that is not sufficient by wrapping sheet 58 like tissue paper (crepe paper) alone, and reduces or prevents uncomfortable feeling when touched by hand in the use by a consumer.

Additionally, FIG. 14 shows schematically a case where super absorbent polymer particles passed out through a fiber aggregate are gathered on the holding sheet 80 in the steps from production to use by consumers when super absorbent polymer particles 54 are provided down below the absorbent core 56, or contained in the absorbent core 56.

Material of holding sheet 80 is not particularly limited, any one with upholding characteristic of absorptive polymer is sufficient. Specifically, for example, there can be exemplified non-woven fabric, crimped pulp, low-absorptive cotton fibers such as non-degreased cotton fiber, degreased cotton fiber, rayon fiber treated with water repellent agent or hydrophobic agent; polyethylene fiber, polyester fiber, acrylic fiber, polypropylene fiber, silk, cotton, linen, nylon, polyurethane and acetate fibers.

In the case of non-woven as holding sheet 80, the holding sheet has the compression energy based on ICES test is 0.01 to 10.00 gf·cm/cm$^2$, preferably 0.01 to 1.00 gf·cm/cm$^2$ and is a non-woven fabric with compression resilience of 10 to 100%, preferably 70 to 100%. Also, elastic degree of holding sheet 80 in the back and forth direction of a product is 0.05 to 0.75 g·cm$^2$/cm to reduce or prevent a shingly uncomfortable feeling resulted from super absorbent polymer particle. Herein "elastic degree in the back and forth direction of a product" means a value obtained when a sample cut to a length of 200 mm and width of 200 mm is bent using a single bending tester (KES-FB2 manufactured by Kato Tech Co., Ltd.) with DEF sensitivity: 20 and curvature range of 0.0 cm$^{-1}$ to 0.5 cm$^{-1}$.

As mentioned above, the reason for providing a holding sheet 80 is to hold absorptive polymer particles fallen off (passed out) downward from absorbent core 56 for example. Thus, the super absorbent polymer particles passed out touch a wearer through wrapping sheet 58 and holding sheet 80, so that there is no fear to pass on a shingly unconformable feeling to a wearer. Particularly, in the case of non-woven fabric with the above compression energy and compression resilience, function as a holding sheet is sufficiently exhibited.

Also, the super absorbent polymer particles passed out are held by the holding sheet 80, do not move onto the wrapping sheet 58, so that there is no fear to generate deviation of absorption capability. In particular, to prevent super absorbent polymer particles from moving onto the holding sheet 80, a hot melt adhesive with adhesion can be applied to the holding sheet 80 beforehand. Also, the upper surface (face facing use-face) of holding sheet 80 may be processed into a rough face to prevent super absorbent polymer particles from moving onto the holding sheet 80. As means for making surface rough or for carding for this purpose, there can be listed the use of non-net face which is a reverse face touching a net in production of non-woven fabric, a marble treatment, processing by needle punch and brushing treatment The holding sheet 80 may be disposed only down below the absorbent core 56 as shown in FIG. 3, or may be extended by passing through the side of absorbent core 56 to the upper surface of absorbent core 56. A plurality of holding sheets 80 can be used by piling them up.

The above examples are an example that holding sheet 80 is disposed between the absorbent core 56 and the rear face region of wrapping sheet 58, but the holding sheet 80 may be in back surface side of wrapping sheet 58 (the mode is not shown), or without purposely disposing the holding sheet 80, wrapping sheet 58 itself may be functionalized as holding sheet, in brief, holding sheet 80 is disposed in the back surface side of absorbent core 56, which reduces and prevents a shingly uncomfortable feeling when touched from the back surface side of a product.

Body fluid impermeable sheet 70 means a sheet disposed simply in the back surface side of absorbent core 56, a sheet for the absorbent core 56 to be interposed between the sheet and top sheet 30 in the present embodiment. Thus, the material of the body fluid impermeable sheet is not particularly limited. Specifically, for example, there can be exemplified olefin resins such as polyethylene and polypropylene, laminate non-woven fabrics laminated with non-woven and polyethylene sheet etc., non-woven fabric that a water proof film is interposed therein to essentially keep impermeability (in this case, body fluid impermeable sheet is composed of water proof film and non-woven). Needless to say, in addition thereto, a material having liquid impermeability and moisture permeability preferably used recently from the prevention of stuffy feeling can be exemplified. As a sheet of material having liquid impermeability and moisture permeability, for example, there can be a microporous sheet obtained in such manner that inorganic fillers are kneaded in a olefin based resin such as polyethylene and polypropylene to form a sheet, followed by stretching uniaxially or biaxially.

The body fluid impermeable sheet 70 is extended to use-surface in a so-called forehead wrapping (not shown), thereby side leakage of body fluid can be prevented, in the embodiment, the side leakage is prevented by a second body-fluid impermeable sheet 72 disposed between two-hold barrier sheet 64 forming a barrier cuff 60. Based on this mode, since the second body-fluid impermeable sheet 72 is extended to the standing of barrier cuff 60, there are merits that side leakage of body-liquid diffused crosswise being run through top sheet 30 and soft shit between barrier cuffs 60 can be prevented.

Barrier cuff 60 provided in both sides of a product is provided in order to stop urine and soft shit moving crosswise being run through top sheet 30 and to prevent side leakage, but it is an augmentative element.

Barrier cuff 60 shown in the figure is formed by two-holding the barrier sheet, it is formed by covering the folded part of top sheet 30 downwards from the back surface side of absorbent core 56 and protruding to surface side. In order to prevent urine moving crosswise in running onto the top sheet 30, in particular, the side part of body-fluid impermeable sheet 70 is inserted between two-hold non-woven fabric, which extends in the partway of barrier cuff 60 protruding to the surface side Also, the shape of barrier cuff 60 can be suitably designed, in the example shown in the figure, an elastic stretch member such as rubber thread 62 is fixed in the end and the middle part of protruding part of barrier cuff 60, barrier cuff 60 stands by the contractive force in a use state. The rubber thread 62 of middle part is located nearer to the center than the rubber threads 62 in the end, fixed in the back and forth ends of top sheet, thus, as shown in FIG. 3, the base part of barrier cuff 60 stands at a slant towards the center and becomes a state that the end from the middle part stands outwards at a slant.

Material of barrier sheet may have a permeable property to body fluid or may have a impermeable property to body fluid, and the kind is not particularly limited. For example, the same material exemplified as top sheet 30 and body fluid impermeable sheet 70 can be employed. However, non-woven is preferable from the points of skin touch and prevention of skin fit due to friction, bulky non-woven fabric such as air through non-woven is more preferable.

Also, according to functions emphasized, water repellant non-woven fabric or hydrophilic non-woven respectively can be used alone or in combination thereof. For example, in the case of emphasizing prevention of body liquid permeation or improvement of skin touch, water repellant non-woven fabric is, for example, preferably a water repellent-treated non-woven coated with silicone based, paraffin based, alkyl chromic chloride based water repellants. On the other hand, in the case of emphasizing absorption of body liquid, hydrophilic non-woven fabrics can be used such as non-woven fabric made of hydrophilic natural fiber, synthetic fiber and regenerated fiber for example, and non-woven fabric of non-hydrophilic fiber to which hydrophilic treatment is given with hydrophilic agents.

As an elastic stretch member, its kind is not particularly limited as long as it has stretchablility. For example, stretch hot melt, stretch film, rubber thread and flat rubber can be exemplified. Also, as the material, for example, there can be exemplified styrene based, olefin based, urethane based and ester based rubbers; and foams of polyurethane, polyethylene, polystyrene, styrene-butadiene, silicone and polyester.

Figure 21:
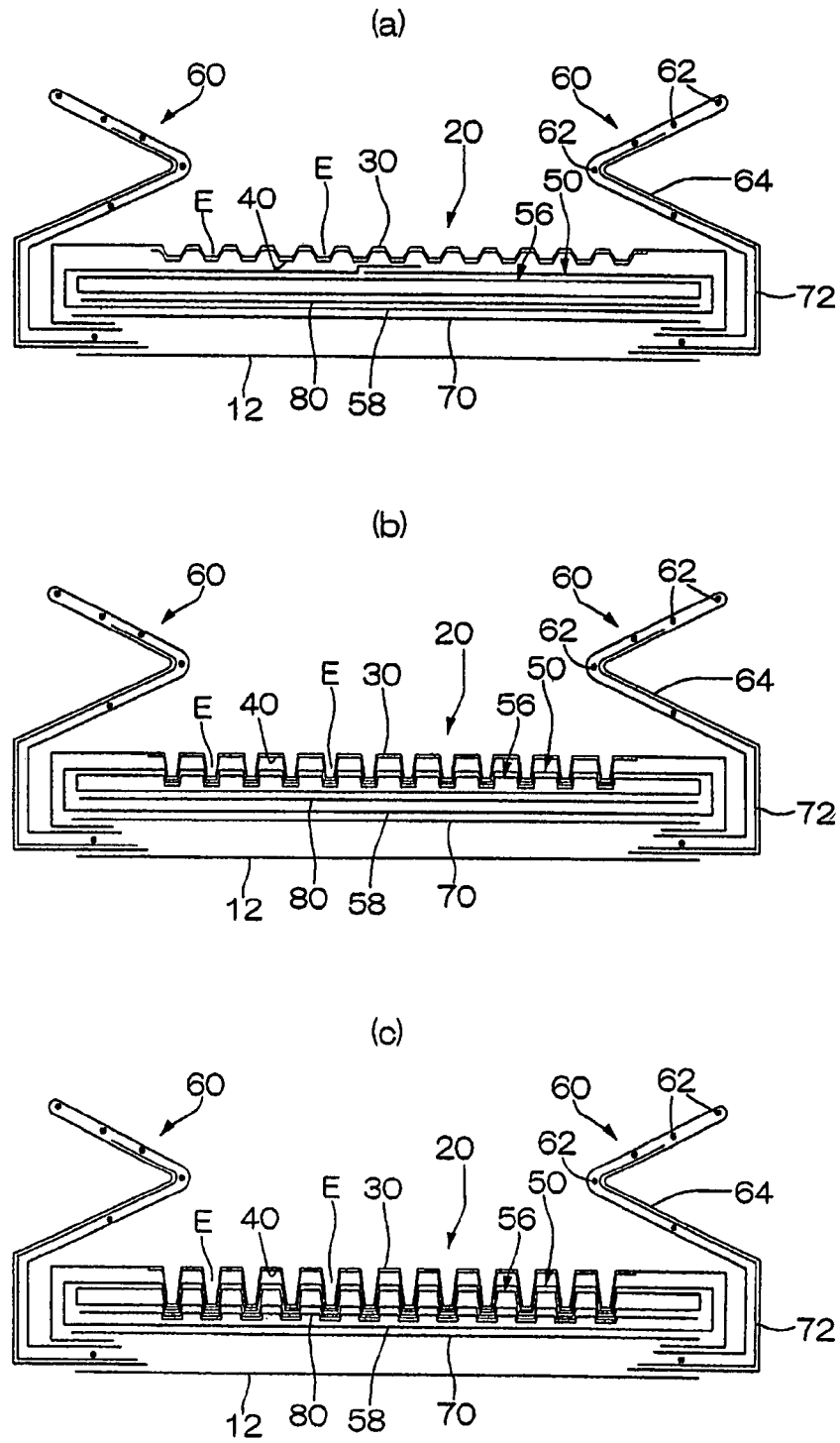
FIG. 21 is a sectional view showing another mode of absorber.

Concavity E may be formed by embossing in the thickness direction of top sheet 30 from the surface side. In this case, concavity E may be formed by embossing only top sheet 30, in addition thereto, concavity E may be formed by embossing both top sheet 30 and medium sheet 40 as shown in FIG. 21(a), concavity E may be formed by embossing to reach a part or almost entire of absorbent core 56 in the thickness direction from the surface of top sheet 30 as shown in FIG. 21(b), and concavity E may be formed by embossing to reach holding sheet 80 from the surface side of top sheet 30 as shown in FIG. 21(c). In order to form concavity E by embossing both top sheet 30 and medium sheet 40, the medium sheet 40 is preferably in a range of 8-40 $g/m^2$ in base weight and 0.2-1.5 mm in thickness, the top sheet 30 is preferably in a range of 15-80 $g/m^2$ in base weight and 0.2-3.5 mm in thickness, from the points that sufficient embossing can be done in the conditions without disturbing liquid permeability.

Also, without forming concavity on top sheet 30, concavity may be formed by embossing on only medium sheet 40, further, without forming concavity on top sheet 30 and medium sheet 40, concavity may be formed by embossing only absorbent core 56, without forming concavity on top sheet 30, medium sheet 40 and wrapping sheet 58, concavity may be formed by embossing on only absorbent core 56.

Concavity E has an effect to induce and diffuse body fluids in its extending direction. Thus, when concavity E is constructed essentially continuously in a channel, including the case where a plurality of concavities are rowed at intervals to form a channel, body fluids diffuse through concave E of the surface side layer before reaching absorbent core, which can utilize a wider part of absorbent core for absorption. Therefore, absorption capacity of a product as a whole increases, which provides absorption goods that leakage from the side and back flow due to lack of absorption capacity hardly occur.

On the other hand, absorbent core 56 composed of tow tends to decrease in rigidity compared with one of the conventional pulp, it is preferable to form concavity by embossing on the absorbent core 56 because rigidity can be increased. Being not shown in a figure, to increase rigidity of absorber 50, it is a preferable mode to form concavity by embossing from the back surface side of absorbent core 56 (opposite side to top sheet 30 side) in the thickness direction. To form concavity on this back surface side, an integrated embossing can be done so as to reach absorbent core 56 from the back surface side of holding sheet 80, wrapping sheet 58, body liquid non-permeable sheet 70 or external sheet 12. Also, such concavity of the back surface side is preferably formed together with concavity E of surface side, concavity of only back surface side can be formed without forming concavity E of surface side. In the case of forming concavity on both surface and back face sides, shape of concavity may be common in both surface and back face, or may be different each other in surface and back face.

Concavity by embossing has an effect to induce and diffuse body fluids in its extending direction. Also, it has an effect to increase rigidity. Thus, it is preferable to determine the shape of concavity by embossing in consideration of these effects. For example, in addition to the concavity being essentially continuously in a channel, including the case where a plurality of concavities are rowed at intervals to form a channel, a plurality of concavities may disposed in spots at intervals. Also, as a plane pattern, there can be adopted various shapes that channel or punctiform concavity is aligned in the longitudinal direction, in the width direction or in lattice combined therewith, zigzag configuration reciprocating in the width direction, or irregularly disposed pattern. Further, shapes such as pin-shape, Mt. Fuji-shape and accordion-shape can be suitably adopted.

Additionally, not shown in a figure, each constitutional member of absorptive body 20 is fixed each other by blanket, bead or spiral application of hot melt adhesives. In the case of applying adhesives, a part to be applied and a part not to be applied in bond area can be intentionally provided. Also, additives can be applied by curtain, spiral, slot, controlled seam (Omega-shaped) and bead applications.

Figure 22:
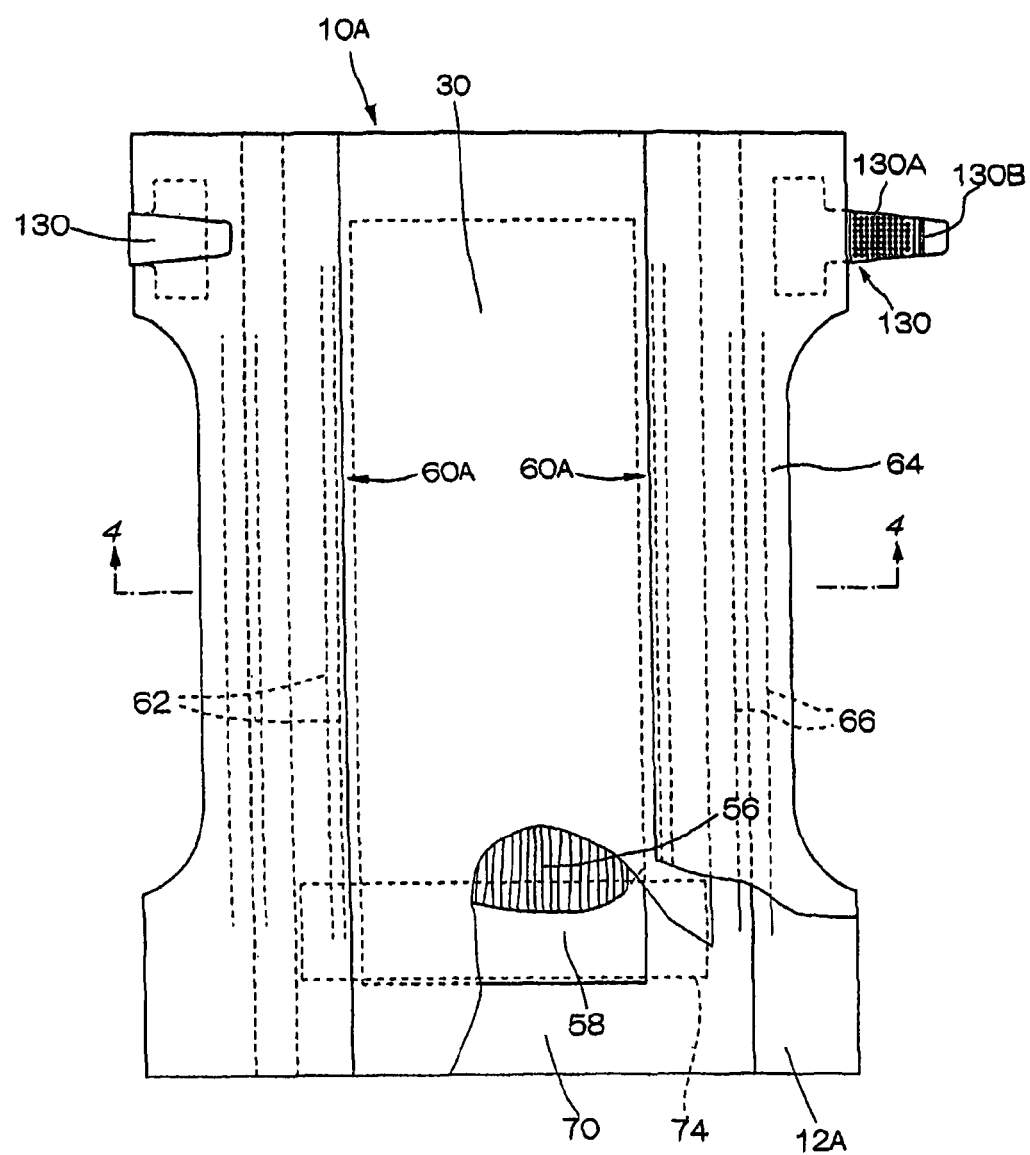
FIG. 22 is a plan view showing a tape type diaper in a development state.
Figure 23:
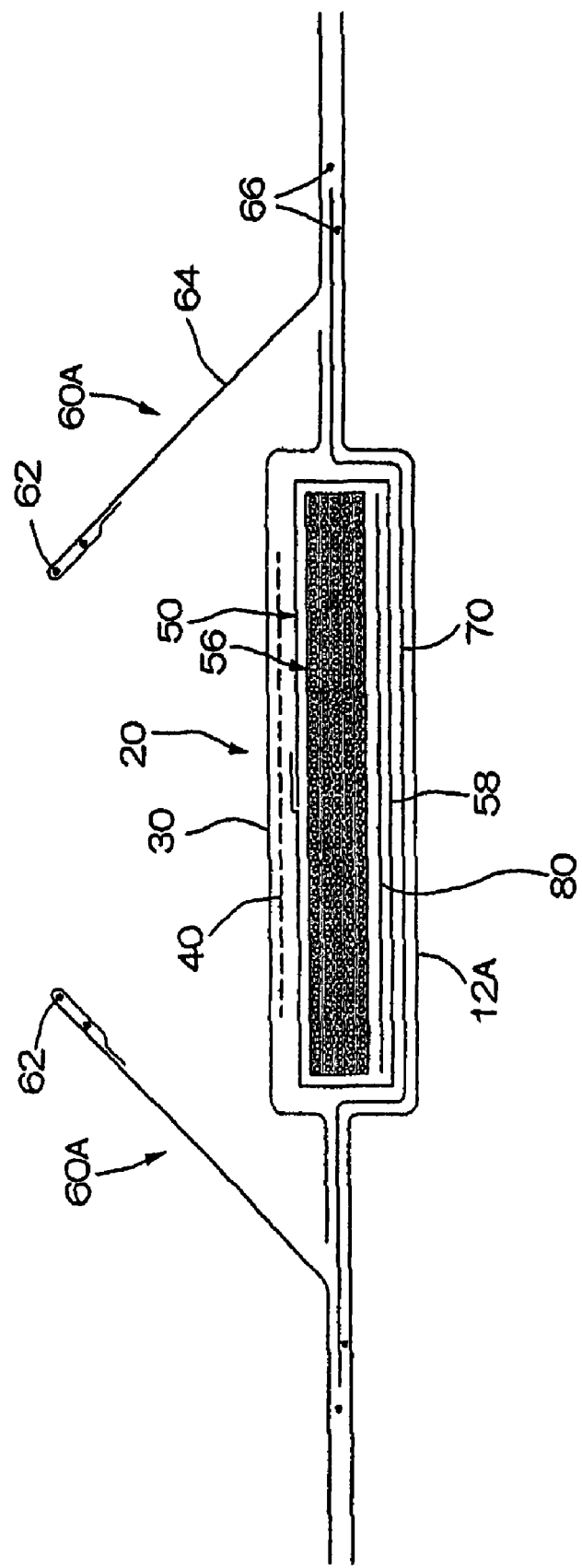
FIG. 23 is a sectional view along 4-4 line of FIG. 22.

Now, FIG. 22 and FIG. 23 show an example of tape-type disposable diaper. FIG. 23 is a sectional view along 4-4 line in FIG. 22, and absorptive body 20 is drawn somewhat in an exaggerated form.

Tape type disposable diaper 10A has a fastening piece provided in both ends of diaper back surface side, has a hook element on a fixing surface of this fastening piece and nonwoven laminate as a back sheet composing the back face of diaper, in wearing a diaper, the diaper is devised so that the hook element of fastening piece can be caught in any place on the surface of back sheet.

Absorptive body 20 is composed of absorbent core 56 interposed between top sheet 30 and body fluid non-permeable sheet 70. The absorbent core 56 is wrapped entirely with a wrapping sheet 58 of tissue paper, is rectangular as viewed in ground plan. A holding sheet 80 is provided between absorbent core 56 and wrapping sheet 58.

Further, a medium sheet 40 is interposed between top sheet 30 and absorbent core 56. The body fluid non-permeable sheet 70 is a rectangle being wider than the absorbent core 56, outside of which a back sheet 12A of non-woven in a sand clock shape is provided.

The top sheet 30 is a rectangle being wider than the absorbent core 56, extended outwards somewhat over the side edge of absorbent core 56, and fixed with body fluid non-permeable sheet 70 by hot melt adhesives etc.

Barrier cuff 60A protruding to use-surface side is formed on both sides of diaper, and this barrier cuff 60A is composed of a barrier sheet 64 of essentially continuous non-woven fabric in the width direction and rubber thread 62 as an elastic stretch member for leg periphery consisting of a piece or a plurality of pieces of rubber thread for example. A fastening piece in hook-and-loop fastener is denoted as 130.

Inner face of barrier sheet 64 has a starting edge for adhesion in a place separated from the side edge of top sheet 30, from this starting edge for adhesion over the extended edge of body fluid non-permeable sheet 70, the outward part in the width direction is bonded with hot melt adhesives etc. The outer face of barrier sheet 64 is bonded in its under surface to the back sheet 12A with hot melt adhesives etc. Further, elastic stretch member for gasket cuff, for example, rubber thread 66 is provided.

The starting edge for adhesion to the body fluid non-permeable sheet 70 in the inner face of barrier sheet 64 forms a standing edge of barrier cuff 60A. The inner side of this standing edge around a leg is a free part not fixed with product body, and this free part stands by contraction force of rubber thread 62.

In the present example, using hook-and-loop faster as fastening piece 130, it can be mechanically fixed to back sheet 12A. Thus, a so-called target tape can be omitted, and fixing position can be arbitrarily chosen by the fastening piece 130.

Regarding fastening piece 130, base of fastening base material such as plastic, poly-laminated non-woven and paper is bonded to back sheet 12A with adhesives for example, it has a hook element 130A in the edge side, the hook element 130A is bonded to the fastening base material with adhesives. The hook element 130A has a lot of hooks in the outer face. It has a temporary adhesive part 130B at the edge of hook element 130A. In a final stage of fabricating a product, the temporary adhesive part 130B is bonded to a barrier sheet 64 to prevent peeling off the edge side of fastening 130. On occasion of use, it is peeled off against the adhesion force, the edge of fastening piece 130 is brought to front body. In the edge side over the temporary adhesive part 130B, fastening base material is exposed as a tab part.

In the opening side of front body, a target print sheet 74 as a design sheet is provided in the inner side of back sheet 12A, on which a target print designed to show an indication of place for fixing the hook element 130A of fastening piece 130 is conducted, which can be recognized from outside through back sheet 12A.

In wearing a diaper, the diaper is worn around a body in a ship shape and contraction force of rubber thread 62 is exerted, so that barrier cuff 60A stands around legs due to contraction force of rubber thread 62.

A space surrounded by standing part forms a space for blocking urine or soft shit. When urine is discharged in the space, the urine is passed through top sheet 30 and absorbed in absorbent core 56, and climbing of solid part in soft shit is prevented by the barrier of standing part of barrier cuff 60A. In case when urine is leaked crossing over the standing distal edge of standing part, side leakage is prevented by a stopping function of plane touching part.

In the present mode, barrier sheet 64 forming each of standing cuffs is preferably not permeable but essentially impermeable or may be semi-permeable. Also, barrier sheet 64 may be treated with silicone to provide a liquid repellant property. At any rate, the barrier sheet 64 and back sheet 12A each are air-permeable and, the barrier sheet 64 and back sheet 12A each preferably are a sheet with a water resisting pressure of 100 mm H2O or more. By this way, side part in the width direction of product becomes air permeable, and stuffy state of wearer can be prevented.

Regarding other points, for example, for materials used in each part, the explanations are skipped because they are the same as in the foregoing underpants type paper diaper.

Figure 24:
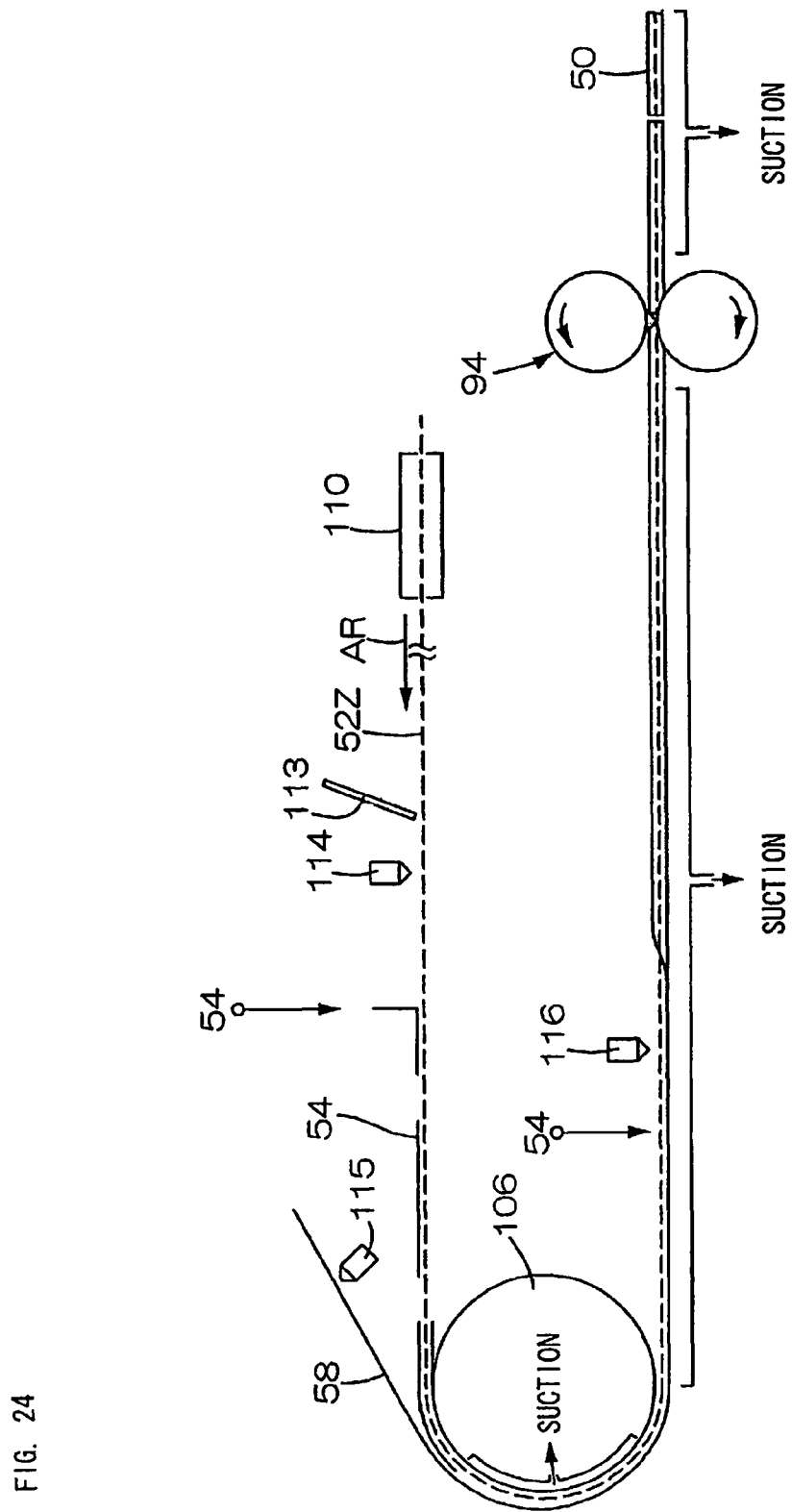
FIG. 24 is a brief overview showing a production facility example of absorber.
Figure 25:
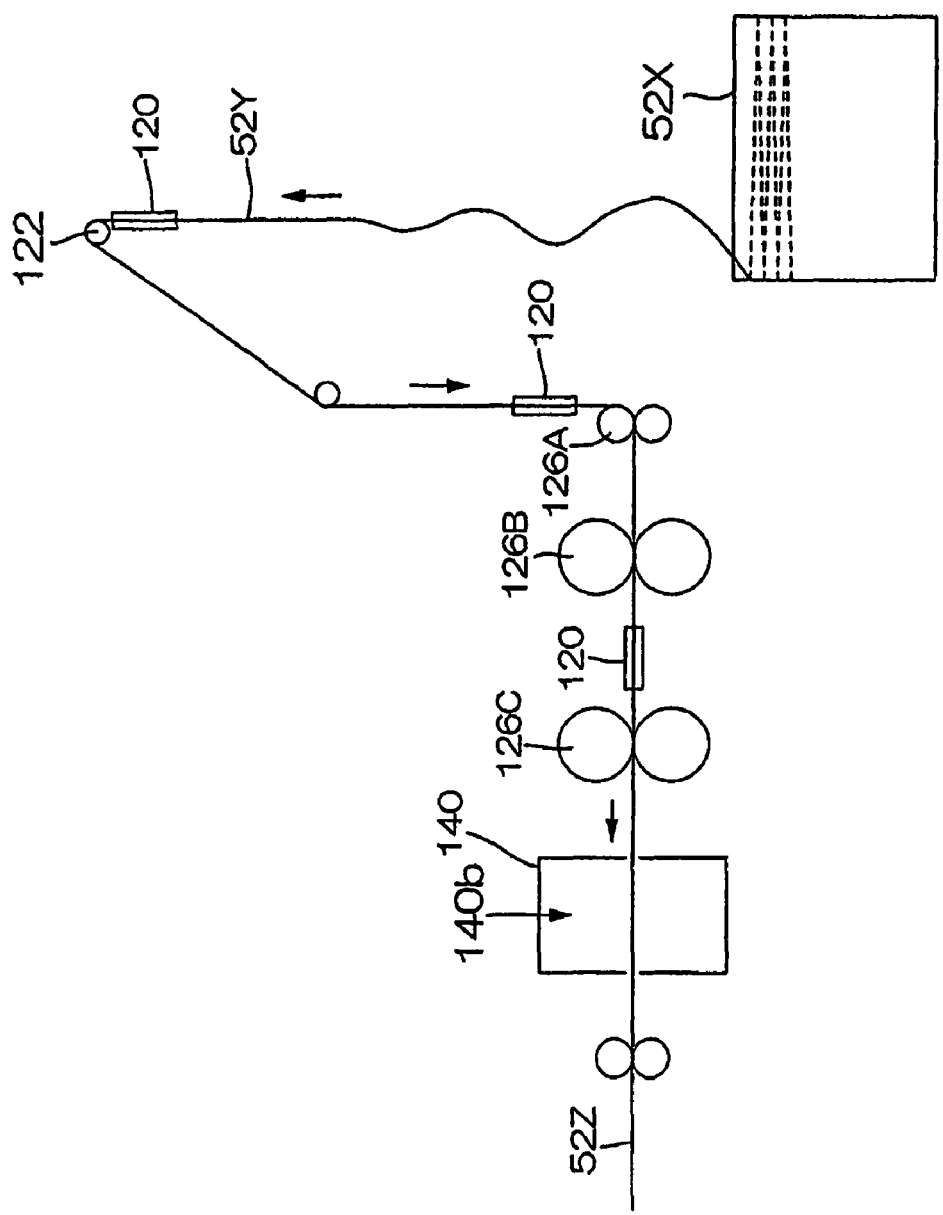
FIG. 25 is a brief overview showing a opening apparatus example.

Next, production facility of absorber will be explained. An example of production facility of absorber is shown in FIG. 24, a continuous strip fiber-aggregate 52Z with width and density desirably opened is supplied. In opening, for example as shown in FIG. 25, tow 52Y is taken out from a tow bale 52x sequentially, in the conveyor process, passed through an enlarging width/opening means 120 using compressed air, and through a opening part combined with a plurality of opening nip rolls 126A, 126B and 126C whose rotational speed is higher toward the downstream roll to widen and opened, then passed through a binder adding box 140 to add a binder 140b (e.g. triacetin mist is filled in a box), thereby to give a fiber aggregate 52Z with desired width and density of tow. It is possible to construct so that this opening line is directly connected to the production line of absorber shown in FIG. 24, the fiber aggregate 52Z produced is directly conveyed in the production line of absorber.

The fiber aggregate 52Z supplied to the production line of absorber can be applied with adhesives before a super absorbent polymer is provided. For this purpose, in the example shown in the figure, an adhesive application device 114 is aligned in the upstream of polymer scattering position in the conveyor line. As the adhesive, an adhesive of thermoplastic resin (operative examples are described above) can be preferably used. Adhesives are applied in a continuous plane by a curtain application or roll application, in addition thereto, by a spiral application, a part applied with adhesives and a plurality of parts not applied with adhesives being surrounded by the part applied with adhesives can be provided. Application amount of adhesive may be suitably determined, ordinarily, it is preferably 1 $g/m^2$ or more. However, when it is too much application, movement of super absorbent polymer is disturbed, thus, it is preferable to determine in a range of 1 to 10 $g/m^2$.

In applying adhesives, in the case where opening means 110 and 120 using compressed air are aligned in vicinity in the upstream of adhesive application device 114, there is fear that compressed air AR leaked along fiber aggregate 52Z flows in the adhesive application device 114 and disturbs the supply of adhesive, or drying adhesive. Therefore, it is preferable to construct a shielding plate 113 installed in the upstream of adhesive application device 114 so as to shield compressed air AR. The shielding plate is preferably installed at least in the side of adhesive application device 114 of fiber aggregate 52Z.

The fiber aggregate 52Z applied with adhesives is subsequently scattered on its upper surface with super absorbent polymer particles 54 by a super absorbent polymer particle scattering means. The scattering can be conducted simply in a way that super absorbent polymer particles fall due to their weights.

Figure 26:
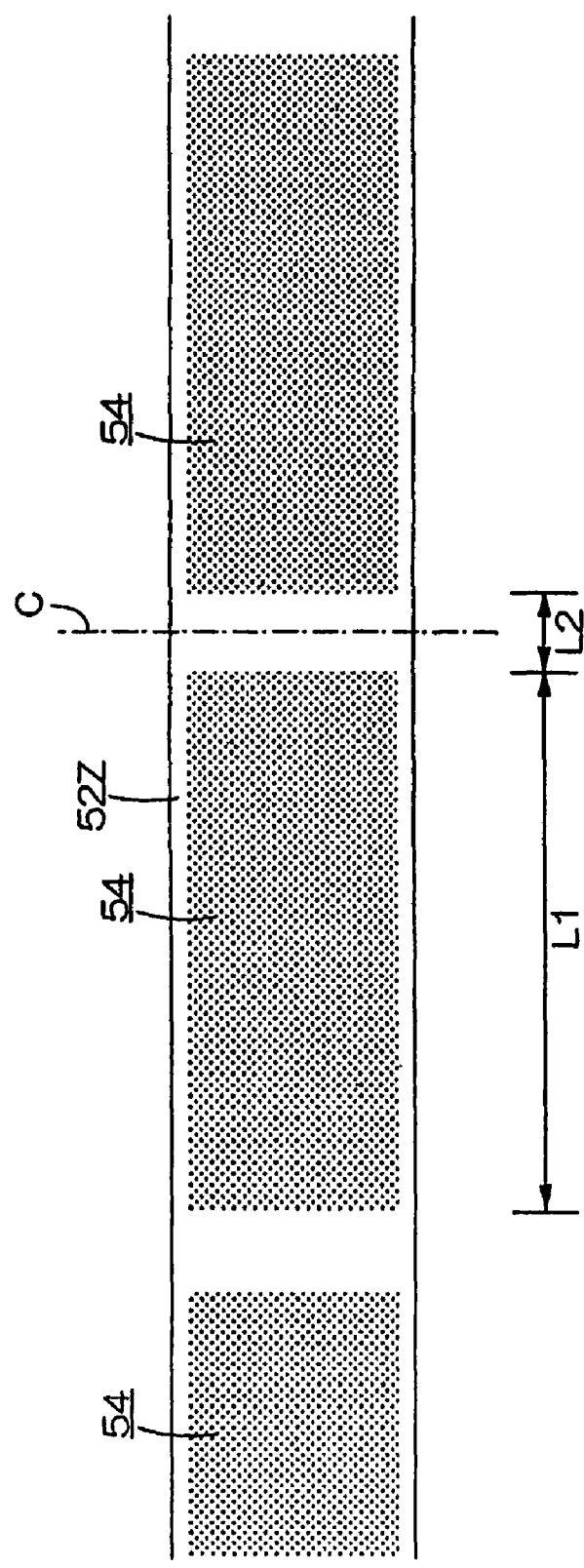
FIG. 26 is a brief overview showing the dispersion mode of super absorbent polymer particles.

In this case, the application amount of super absorbent polymer particles 54 can be periodically changed according to need. Specifically, it is a preferable mode that a scattering state and a non-scattering state are alternately repeated, a part applied with super absorbent polymer particles 54 and a part not applied therewith are alternately provided in the conveyor direction, i.e., super absorbent polymer particles 54 are intermittently applied in the conveyor direction. In this case, as shown in FIG. 26, it is particularly preferable to scatter few super absorbent polymer particles 54 in a cut off part C to be cut afterwards. Specifically, it is particularly preferable for cutting in such way that a suitable length of L1 is somewhat shorter than a length of absorber, for example, a cut off part C is determined at intervals of 10 to 30 cm in the conveyor direction, as a center from which, in a length L2 including a sufficient cut off margin, for example, in about 5 to 20 mm over the entire width direction, there is provided a state that essentially no super absorbent polymer particles 54 exist (less than 0.01 $g/cm^2$ of base weight). By synchronizing application step and cutting process in this way, as clear from the following examples, life of cuter blade is remarkably prolonged compared with the case of cutting in the part containing super absorbent polymer particles 54.

By utilizing the periodical change in the application amount of super absorbent polymer particles 54, a large part and a small part of application amount can be provided. Also, the application amount can be continuously changed, in this case, for example, there can be adopted a mode that no super absorbent polymer particles 54 are scattered in cut off part, and the application amount increases toward the center in the conveyor direction.

Subsequently; the fiber aggregate 52Z scattered with super absorbent polymer particles 54 can be only turned around by a turning roll to proceed to the following step, but, it is a preferable mode that it is simultaneously suctioned and turned around by a vacuum roll 106. The vacuum roll 106 has suction holes around the periphery wall, it is constructed for the suction to be conducted from inside by a pump not shown in the figure across a given range in the periphery direction (region of almost left half in the example shown in the figure). The fiber aggregate scattered with super absorbent polymer particles 54 is introduced while being contacted with the periphery by the vacuum roll 106. In this step, by suction through suction holes of vacuum roll 106, atmosphere is passed from the application side of super absorbent polymer particles 54, through the inside of fiber aggregate 52Z to the opposite side (vacuum roll 106 side), super absorbent polymer particles 54 are moved to the inside of fiber aggregate 52 Z by the passing force of this gas.

In a particularly preferable mode, after super absorbent polymer particles 54 are scattered on the fiber aggregate 52Z, further on which a wrapping sheet 58 is covered. In this case, in the vacuum roll 106, suction is conducted from the opposite side of the face on which the sheet 58 is covered. In this manner, when the sheet 58 is covered in suction, a strong suctioning force operates on the super absorbent polymer particles 54 compared with no covering case, which can move and disperse the super absorbent polymer particles 54 into the fiber aggregate 52Z. As such sheet, there can be used liquid permeable sheets such as crepe paper, non-woven fabric, and sheet with open holes; and liquid non-permeable sheets such as polyethylene film. In the example shown in the figure, this sheet is regarded as a wrapping sheet 58, in the case where the foregoing holding sheet 80 is provided, the holding sheet 80 together with the wrapping sheet 58 not shown in the figure are supplied, suction can be conducted in a piled sate of these sheets and the fiber aggregate 52 Z.

In order to fix super absorbent polymer particles 54 to a fiber aggregate 52Z, adhesives are applied to a fiber aggregate 52Z before applying super absorbent polymer particles 54, in addition thereto, not shown in a figure, adhesives are applied to a fiber aggregate 52Z after applying super absorbent polymer particles 54 and before moving super absorbent polymer particles 54 into a fiber aggregate 52Z, namely, regarding the example shown in the figure, adhesive can be also applied to a fiber aggregate 52 Z from after scattering super absorbent polymer particles 54 till entering into a vacuum roll 106.

Also, when after scattering super absorbent polymer particles 54 on a fiber aggregate 52Z, further, on which a holding sheet 80 and a wrapping sheet 58 are covered, an adhesive application device 115 in the sheet feeding path to a vacuum roll 106 is installed, thereby adhesives are applied to the surface of fiber aggregate 52 Z side facing to the sheet 58 beforehand. When this mode is adopted, super absorbent polymer particles 54 exposing on the fiber aggregate 52Z are fixed through adhesives on the sheet 58, non-bonded super absorbent polymer particles 54 are moved to the inside of fiber aggregate 52Z later by suction. However, there is fear of problems resulting from adhesion of adhesive in the facilities of the downstream such as adhesives adhering to the vacuum roll 106 to cause the clogging of holes, it is preferable not to dare to apply adhesives to the sheet 58.

Furthermore, an adhesive application device 116 is installed on the exposure side of fiber aggregate 52Z in the downstream of vacuum roll 106 (opposite face of sheet 58, upper face in the figure), after suction, namely, adhesives can be applied to the fiber aggregate 52 Z after the super absorbent polymer particles 54 are moved. When this mode is adopted, the super absorbent polymer particles 54 on the polymer applied side of fiber aggregate 52Z and the super absorbent polymer particles 54 moved into the opposite side can be fixed to the fiber aggregate 52Z. Also, in the case where a sheet is separately covered on the exposure side of fiber aggregate 52Z or, as described above, both sides of wrapping sheet 58 are covered by wraparound and fold-back of both ends of fiber aggregate 52 Z, the super absorbent polymer particles 54 moved into the exposure side of fiber aggregate 52Z can be fixed to the sheet 58.

Supply of these adhesives can be adopted in any one or in combination thereof. As the adhesive, an adhesive composed of thermoplastic resin (operative examples are the same as described above) can be preferably used.

Then, in this way, the fiber aggregate 52Z applied with super absorbent polymer particles 54 is cut in a given length to give a separate absorber 50 after a sheet is separately covered thereon, or both sides of sheet 58 are covered by wraparound and fold-back of both ends of fiber aggregate 10 with a sailor as shown in the figure; for example.

On the other hand, uniformity is preferable in the case of aiming at volume distribution of super absorbent polymer particles to the fiber aggregate 52Z, density distribution of super absorbent polymer particles and fiber density distribution for multi-purpose, but in the case of aiming at exhibiting a particular absorption, it is also preferable to provide relatively large part and small part, or high part and low part according to the purpose.

Specifically, in scattering polymer, relatively large part and small part of application amount in the plane direction can be provided. In absorbent article particularly, there are many cases that absorption amount is desired to increase in the center of absorber in the width direction, in this case, in scattering polymer, super absorbent polymer can be scattered so that the amount of super absorbent polymer in the middle in the width direction of fiber aggregate 52Z is larger than the amount of both sides in the width direction of fiber aggregate 52Z.

Also, in scattering polymer, super absorbent polymer can be scattered so that the amount of super absorbent polymer in the middle in the longitudinal direction of fiber aggregate 52Z (middle in the longitudinal direction of the part becoming each absorber) is larger than the amount of super absorbent polymer in back and forth parts in the longitudinal direction of fiber aggregate 52Z. This kind of scattering can be achieved by periodical change of application amount of the foregoing super absorbent polymer particles 54.

Also, relatively high part and low part in density of super absorbent polymer in fiber aggregate can be provided by providing high part and low part in suctioning force in vacuum roll 106, because of placing a larger amount of super absorbent polymer into the side of vacuum roll 106 in a place of higher suctioning force. For example, by operating stronger suctioning force in vacuum roll 106 in the middle in the width direction of fiber aggregate 52Z than both sides in the width direction of fiber aggregate 52Z (or suction time may be lengthened), like the foregoing eighth mode, higher density of super absorbent polymer in the middle in the width direction of fiber aggregate 52Z than both sides in the width direction can be achieved. In this structure, the absorption speed in the middle in the width direction of fiber aggregate 52Z becomes low, the absorption speed in both sides in the width direction becomes high, thus, liquid tends to spread entirely in an absorber, namely, improving diffusion in the case of using in absorbent article.

Furthermore, in a fiber aggregate 52Z composed of tow, since liquid flows easily along the continuous direction of fiber, a particular absorbing characteristic can be obtained by providing relatively high part and low part in fiber density. This can be achieved by conducting partially strong opening or using a plurality of tows partially bundled in production of fiber aggregate 52Z. As an operative example, a preferable mode is that the fiber density in the middle in the width direction of fiber aggregate 52Z is set to be higher than the fiber density in both sides in the width direction like the foregoing ninth mode. In a fiber aggregate 52Z composed of tow, since liquid flows easily along the continuous direction of fiber, more liquid flows along the continuous direction of fiber in the middle in the width direction of fiber aggregate 52Z.

Also, it is possible not to move super absorbent polymer particles 54 by utilizing the passing force of gas. As shown in FIG. 24, such mode can be achieved by applying super absorbent polymer particles 54 to a fiber aggregate in the downstream of vacuum roll 106 or omitting the suction by vacuum roll 106.

Also, it is possible to apply super absorbent polymer particles 54 in the upstream of vacuum roll 106 and apply super absorbent polymer particles 54 in the upstream of vacuum roll 106 on a fiber aggregate 52Z as well. In this case, it is possible to apply super absorbent polymer particles 54 entirely on the parts becoming an absorber in both upstream and downstream of vacuum roll 106, it is also possible to apply super absorbent polymer particles 54 on a part of the parts becoming an absorber in the upstream of vacuum roll 106 and apply super absorbent polymer particles 54 on the other part in the downstream of vacuum roll 106.

Further, in the case of applying super absorbent polymer particles 54 on a fiber aggregate 52Z in the downstream of vacuum roll 106, according to need, in the downstream of vacuum roll 106, particularly, in the case of applying super absorbent polymer particles 54 on a fiber aggregate 52Z in the downstream of vacuum roll 106, in almost all or partly in the conveyor line after the application position, suction is conducted downwards through a sheet 58 and a fiber aggregate 52Z, which can accelerate the movement of polymer into fiber aggregate 10.

Figure 30:
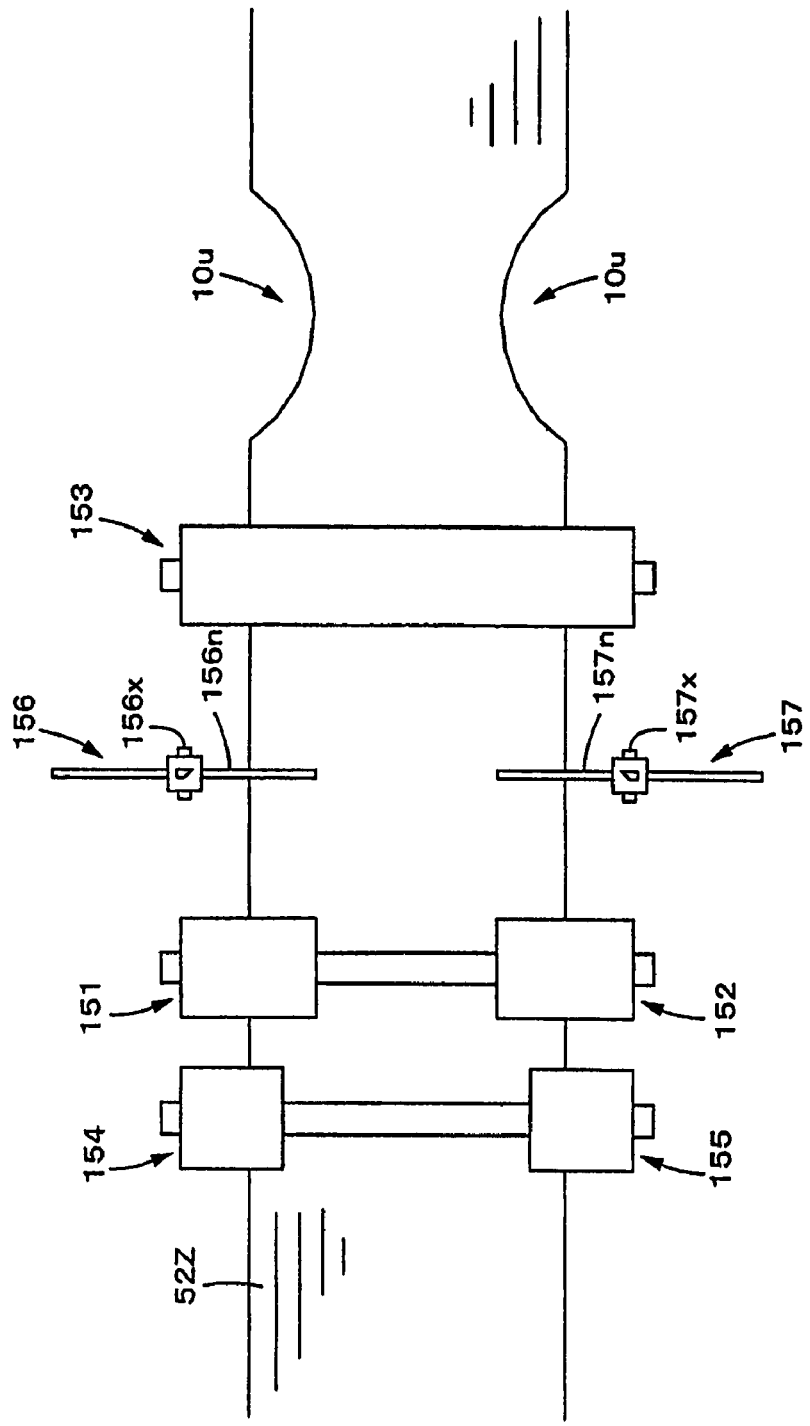
FIG. 30 is a plan view schematically showing a production facility example of absorber in another mode.
Figure 31:
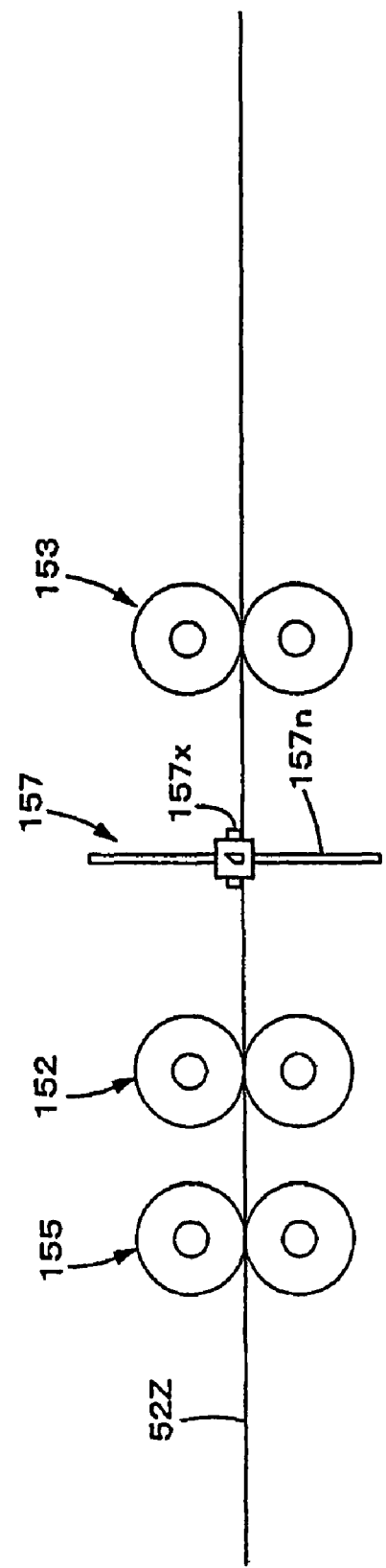
FIG. 31 is a front view schematically showing a production facility example in another mode.

Next, an example of production facility for absorber of the present invention using a fiber aggregate obtained by the facility shown in FIG. 25 will be explained. The example of production facility for absorber of the present mode is shown in FIG. 30 and FIG. 31, a continuous strip fiber aggregate 52Z with desired width and density composed of tow is provided. For this purpose, this production line is directly connected to the foregoing production line of fiber aggregate, the fiber aggregate 52Z can be directly supplied into the production line.

In the present mode, the edge in the width direction is notched under a extension force applied along the longitudinal direction to the edge in the width direction of fiber aggregate 52Z. For this purpose, in the example of facility shown in the figure, nip rolls 151 and 152 in the upstream holding the edge in the width direction of fiber aggregate 52Z continuously supplied are each installed in the edge in the width direction of fiber aggregate 52Z, and in the down stream from this, a downstream nip roll 153 holding entirely width direction of fiber aggregate 52Z is installed, by the nip pressure of nip roll in the upstream, it is constructed for a conveyor speed of edge in the width direction of fiber aggregate 52Z to be lower than the middle in the width direction in between upstream nip roll and down stream nip roll. By this difference of speed, extension force is generated to the edge in the width direction of fiber aggregate along the longitudinal direction.

Extension force applied to the edge in the width direction of fiber aggregate 52Z can be suitably set by adjusting upstream nip pressure, ordinarily, when the middle in the width direction is 100%, it is 100% or more, less than 300%, in particular, preferably 200% or less.

Figure 32:
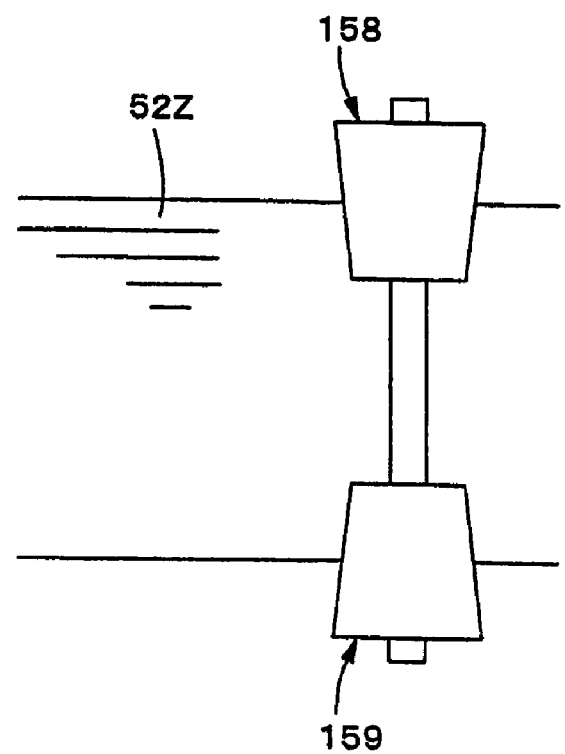
FIG. 32 is a plan view schematically showing other upstream roll example of a production facility example in another mode.

For example, to form concavity 10u with wider notch toward both ends like V character or U character, it is preferable to give extension force larger as approaching to the edges in the width direction. For this purpose, a plurality of sections of upstream rolls are installed in the stream direction of line (in the examples shown in the figure, nip roll sections shown as symbols 151 and 152, and nip roll sections shown as symbols 154 and 155), it can be constructed to be nipped by more nip rolls as they approach the edges in the width direction of fiber aggregate 52Z. Also, as shown in the FIG. 32, as upstream rolls, it is possible to adopt elastic rolls 158 and 159 with larger outer diameter as approaching to the edges in the width direction of fiber aggregate 52Z.

Further, cutting means 156 and 157 are each installed in between upstream nip rolls 151 and 152 and a downstream nip roll 153. The cutting means 156 and 157 are constructed with cutting blades 156n and 157n to notch the edges in the width direction of fiber aggregate 52Z along the width direction and a driving means of cutting blades not shown in the figure. More specifically, rotational axes 156x and 157x are each provided along MD direction at both sides of line (fiber aggregate), cutting blades 156n and 157n are installed so as to protrude in the radial direction of each rotational axis of 156x and 157x, both axes 156x and 157x are rotated by a driving unit not shown in the figure, in association with therewith, rotating each of cutting blades 156n and 157n passes through the edges in the width direction of fiber aggregate 52Z from above to down to cut. The number of cutting blades 156n and 157n is suitably determined, a plurality of blades at intervals of equal distance in the rotational direction are set up in the example shown in the figure. Also, the rotating speed can be suitably adjusted according to the line speed and interval of cutting place.

In production, regarding the edges in the width direction of fiber aggregate 52Z passing through between upstream nip rolls 151 and 152 and a downstream nip roll 153, the edges in the width direction of fiber aggregate 52Z are notched by cutting means 154 and 155 along the width direction under extension force applied according to nip pressure of upstream nip rolls 151 and 152. The extension force applied on the edges in the width direction of fiber aggregate 52Z is released by this notch, contraction takes place in the longitudinal direction for the parts notched to separate each other, concavity 10u is formed so that the edges in the width direction of fiber aggregate 52Z are narrowed toward the middle in the width direction. In this way, concavity 10u can be very easily formed in a place around a leg in even fiber aggregate composed of tow 52Z.

Figure 33:
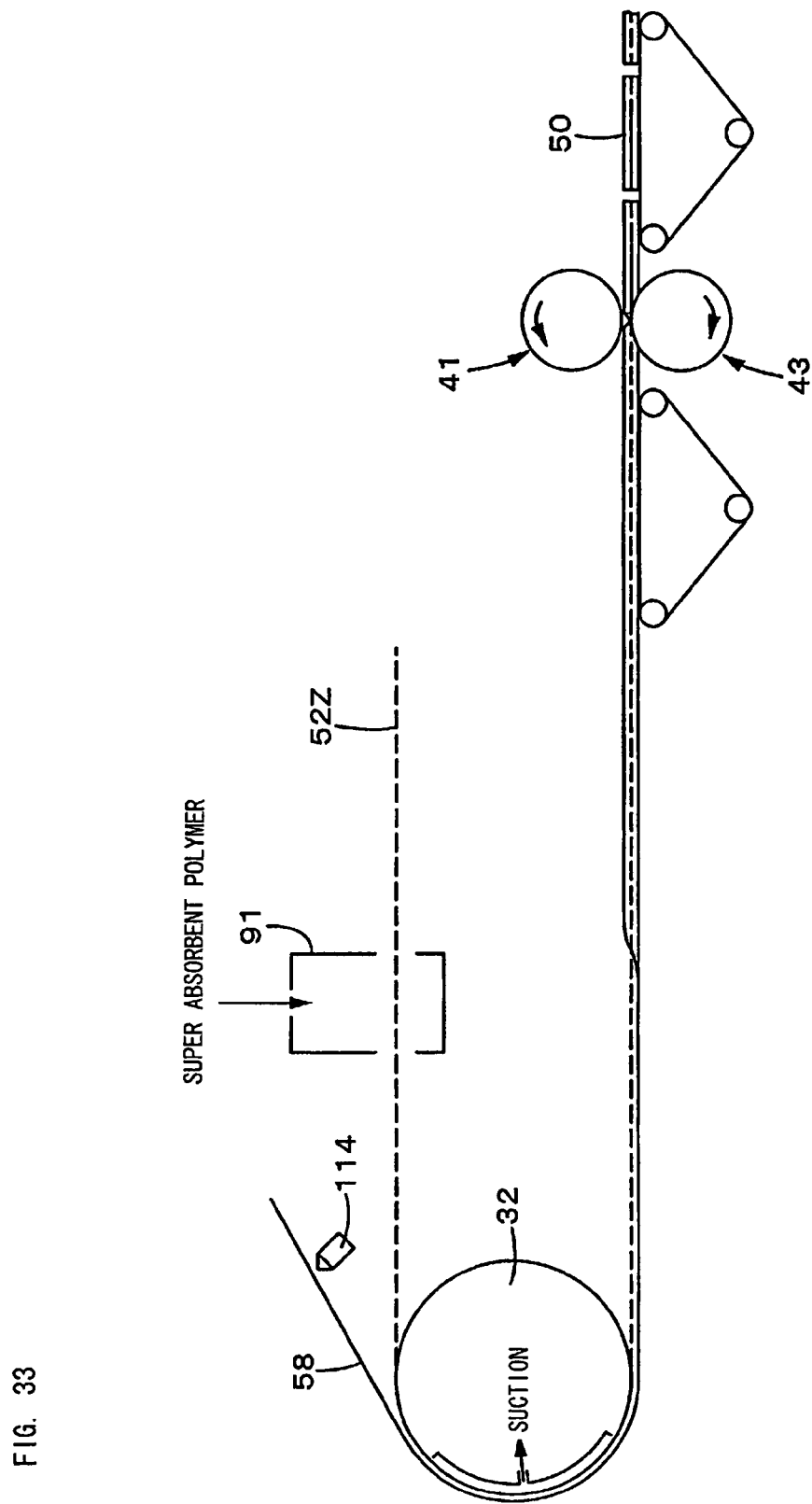
FIG. 33 is a brief overview showing the production flow of another mode of absorber.

The fiber aggregate 52Z formed with concavity 10u is converted to a separate absorber shown in FIG. 33, for example, supplied to an assembly line of product not shown in the figure, and can be embedded into absorbers of diaper and sanitary napkin.

Namely, in the example shown in FIG. 33, the fiber aggregate 52Z formed with concavity 10u is first passed through a polymer scattering box 91, scattered with super absorbent polymer on the upper surface. The application amount (base weight) of super absorbent polymer can be suitably determined according to the absorption amount required in applications of the absorber as described above.

In a preferable mode, then, the fiber aggregate 52Z scattered with super absorbent polymer is sent to a suction drum 32. The suction drum 32 has suction holes on the periphery wall, it is constructed so as to suck from inside by a suction pump not shown in the figure over a given range of periphery direction (region of almost left half in the example shown in the figure). The fiber aggregate 52Z scattered with polymer is introduced while being contacted with the periphery by the vacuum drum 32. In this step, by suction through suction holes of suction drum 32, atmosphere is passed from the application side of super absorbent polymer, through the inside of fiber aggregate to the opposite side, super absorbent polymer is moved to the inside of fiber aggregate by the passing force.

In the mode shown in the figure, a fiber aggregate is wrapped with a sheet, an adhesive is applied to the cutting place in the inner face of sheet. After super absorbent polymer is scattered on the fiber aggregate 52Z, further, on which a wrapping sheet 58 is covered. In the case of no suction, it is also possible to adopt a simple method of placing a fiber aggregate on a sheet and further on which super absorbent polymer is scattered. As this wrapping sheet 58, there can be used liquid permeable sheets such as crepe paper, non-woven fabric, and sheet with open holes; and liquid impermeable sheets such as polyethylene film.

Also, an adhesive application device 114 is installed for fiber aggregate 52Z in the sheet supplying pass way, wrapping sheet 58 is applied with adhesives on the surface to be fiber aggregate 52Z side by the adhesive application device 114, then, placed on the upper surface of fiber aggregate 52Z. As the adhesive, an adhesive composed of thermoplastic resin (operative example is the same as described above) can be preferably used.

Figure 34:
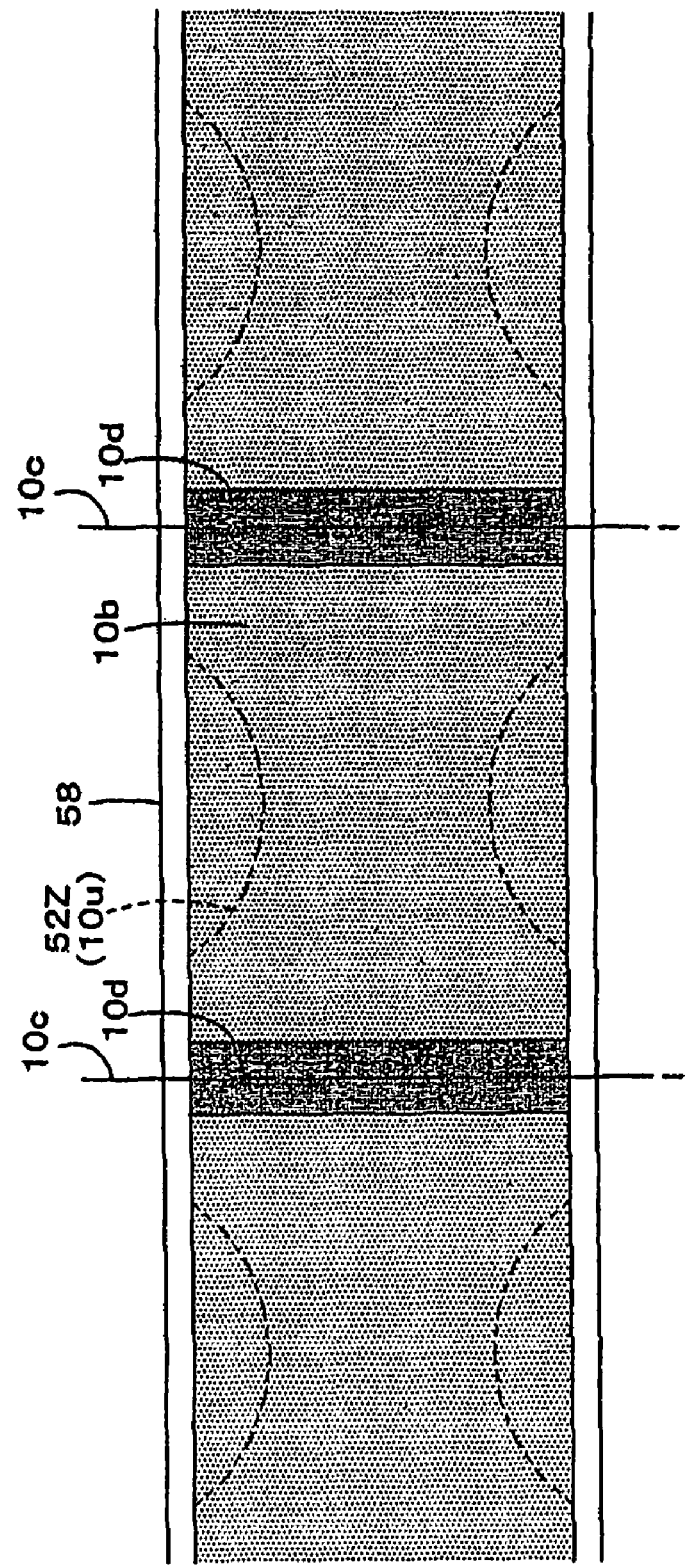
FIG. 34 is a plan view schematically showing an adhesive application example to sheet.
Figure 35:
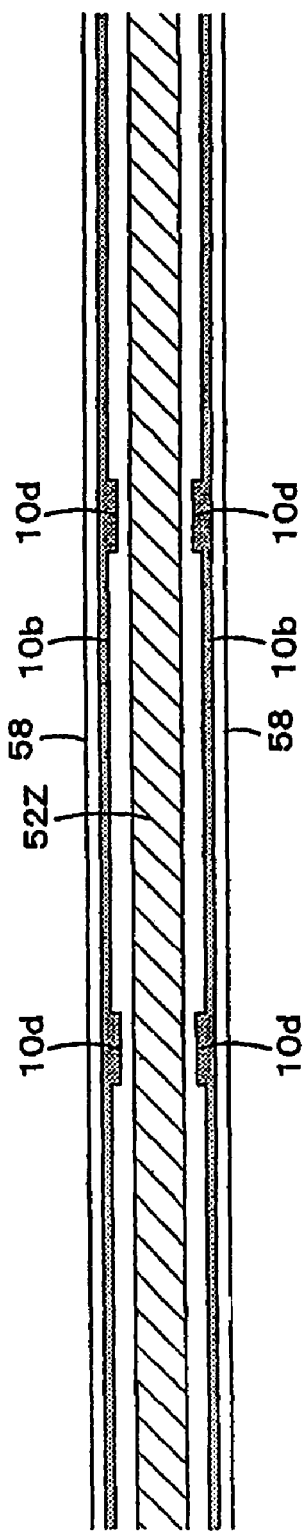
FIG. 35 is a longitudinal sectional view schematically showing an adhesive application example to sheet.

In the example show in the figure, this adhesive is applied to a region including at least a place for cutting to separate into an absorber (planned cut place). The application amount is 2 g/m2 or more, preferably 5 g/m2 or more to enhance reliability of pressure adhesion explained later. Adhesives can be applied only on a part including the planned cut place, namely, can be applied intermittently in MD direction, it can also applied in a continuous plane. In this case, super absorbent polymer exposing on the surface of fiber aggregate 52Z is fixed with a wrapping sheet 58 through adhesive. As shown in FIG. 34 and FIG. 35, from the points of reliability in pressure adhesion and fixation of super absorbent polymer, adhesive 10b is applied continuously in MD direction, the application amount only at cut place is preferably increased. This increased part of adhesive is denoted as a symbol 10d in the figure. In this case, the application amount can be changed at one adhesive, application device 114, it is preferable that application devices for continuous application and intermittent application are set up at the same time, an adhesive for fixing highly adsorptive polymer is applied continuously by the former, intermittent application for the planned cut place is carried out by the latter.

Also, in regard to the application of adhesive 10d on the planned cut place 10c, as shown in FIG. 36(a), it is also preferable mode that adhesive 10d is applied to the planned cut place in the inner face of wrapping sheet 58 in the same application width as the design width of fiber aggregate 52Z to keep minimally, a fiber aggregate 52Z opened over this application width is bonded in the inner face of wrapping sheet 58 with adhesive 10d. In this case, as shown in FIG. 36(b), the fiber aggregate 52Z tries to contract after adhesion, but it does not contract down to application width of adhesive 10d by the constraint operation of adhesive 10d. Therefore, dimensional stability is improved in the width direction of fiber aggregate 52Z.

Also, in the example shown in FIG. 36, this adhesive 10d is applied for the inner face of wrapping sheet 58 into faces facing to the both sides in the thickness direction of fiber aggregate 52Z, but it is also possible to apply only into a face of one side of thickness direction of fiber aggregate 52Z On the other hand, the fiber aggregate 52Z bonded to the inner face of wrapping sheet 58 through adhesives 10b and 10d is converted to a separate absorber 50 with a given length, for example, in such manner that it is covered with other sheet or, the back surface side of wrapping sheet is wrapped by wraparound and fold-back of both edges of fiber aggregate 52Z with a sailor as shown in the figure, followed by cutting subsequently in the planned cut place.

Figure 37:
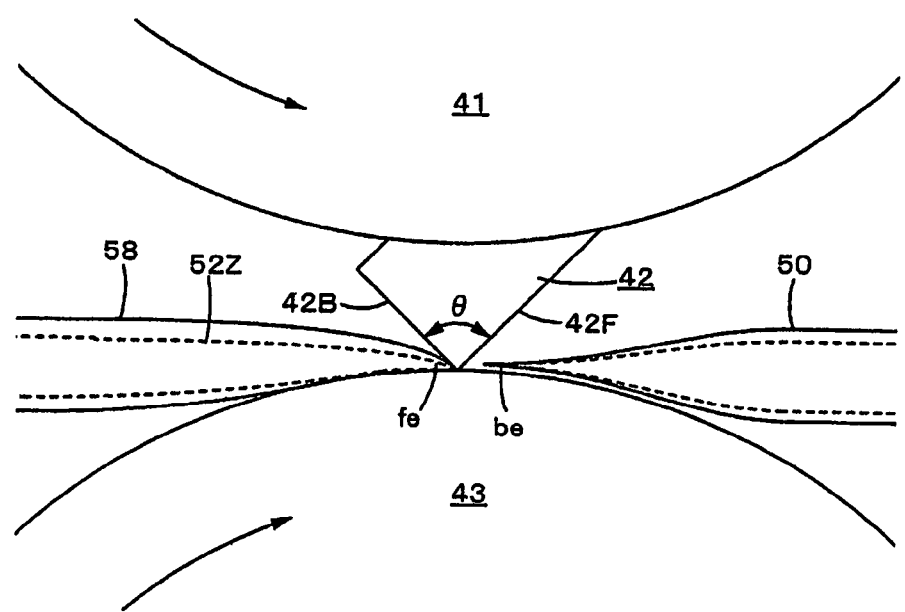
FIG. 37 is an enlarged diagram of cutter roll part.

In cutting, in a particularly preferable mode, the edges formed by cutting are pressure bonded at the same time in cutting. In the case of continuous treatment in a production line, specifically, as shown in FIG. 33 and FIG. 37, a blade edge 42 extending along the width direction of roll is protruded, it is preferable to use pressure bond cutting means equipped with a cuter roll 41 with an angle θ between front face and rear face in the rotational direction of blade edge 42 of 90 degrees or more and a anvil roll 43 contacting the blade edge. The fiber aggregate 52Z wrapped with the wrapping sheet 58 is passed between the cutter roll 41 and anvil roll 43, thereby it is cut by the blade edge 42 of cutter roll 41, the downstream edge of absorber 50 that has been separated and the upstream edge of absorber to be separated next are formed. In concurrence with this cutting, in the downstream edge be of the separated absorber 50 and the upstream edge fe of absorber to be separated next are pressure bonded by front face 42F and rear face 42B in the rotational direction of blade edge 42.

Figure 38:
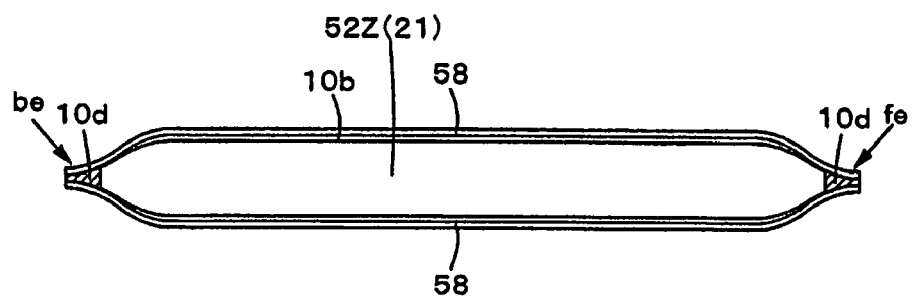
FIG. 38 is a schematic diagram of longitudinal cross section of absorber.

As described above, as shown in FIG. 38, absorber 50 is produced with a structure such that both ends in longitudinal direction are formed by cutting, and the fiber aggregate 52Z in wrapping sheet 58 is wedged at both edges fe and be in the longitudinal direction, and these are pressure bonded using adhesive 10d.

Figure 39:
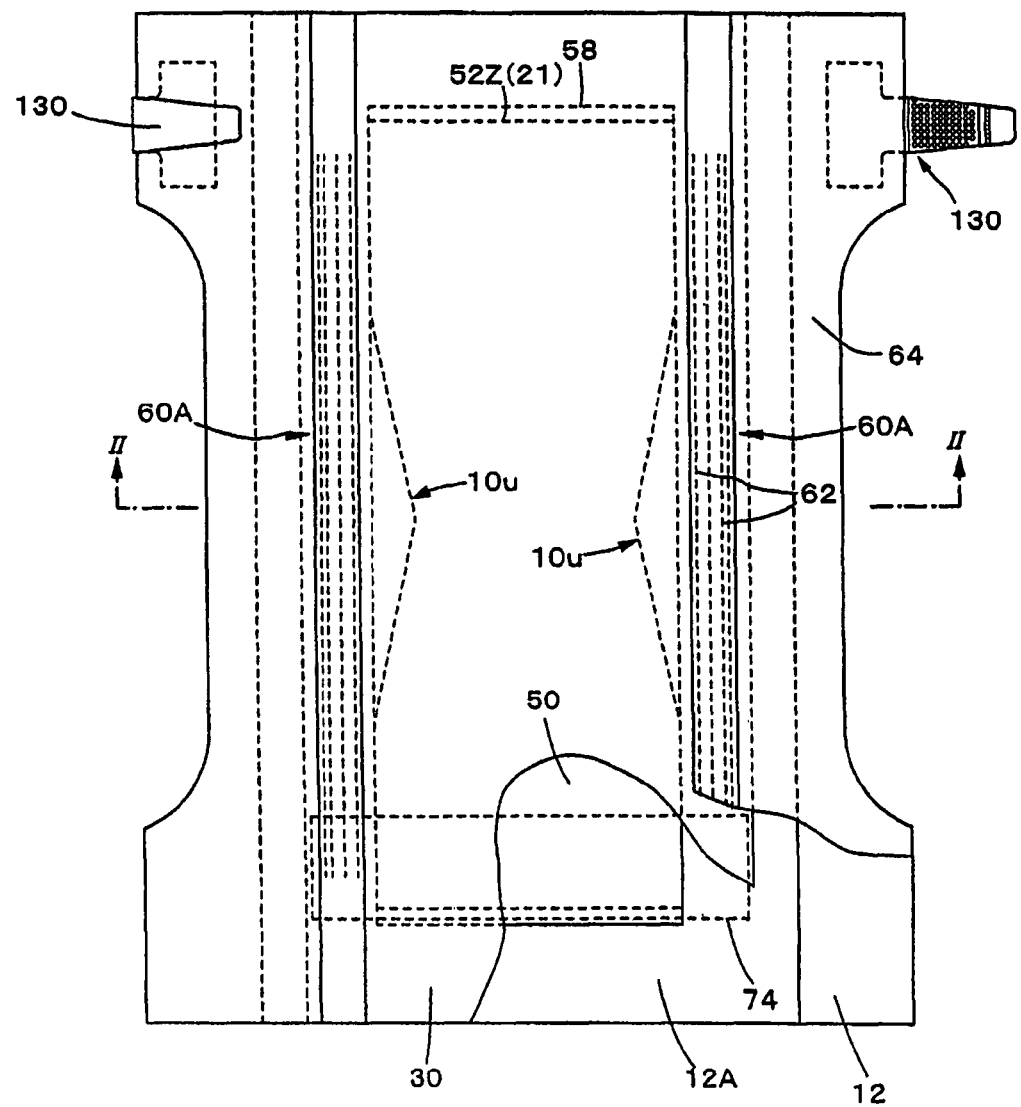
FIG. 39 is a plan view of paper diaper example in a development state.
Figure 40:
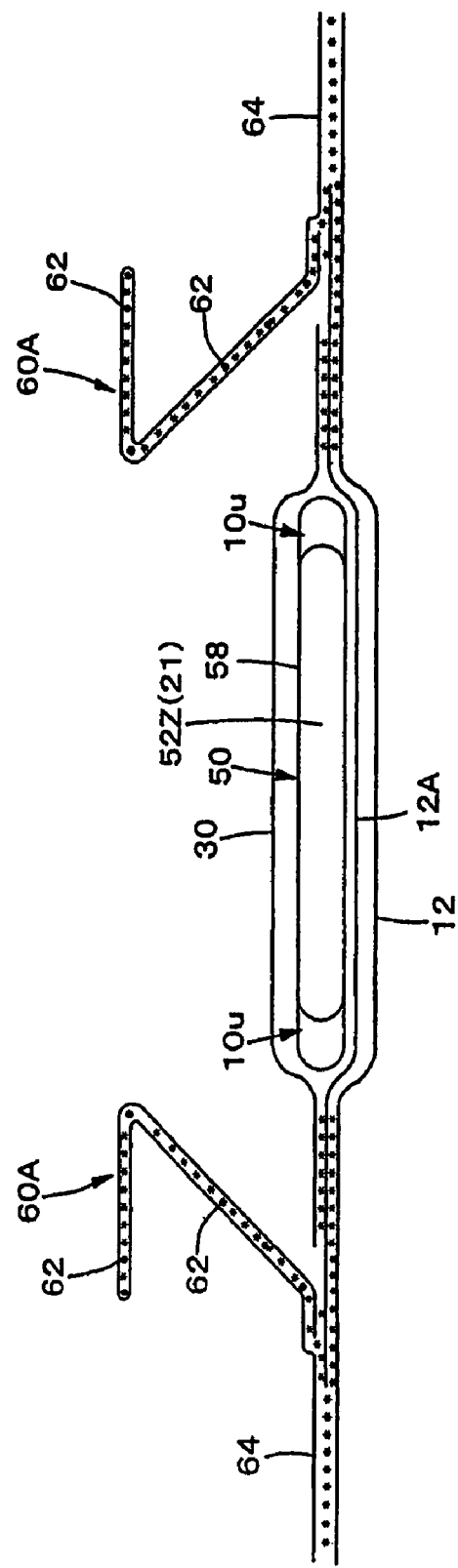
FIG. 40 is a sectional view along II-II line of FIG. 39.

FIG. 39 and FIG. 40 show an example that absorber 50 containing a fiber aggregate 52Z is adopted to a paper diaper, the absorber 50 of the present invention is present between a liquid permeable top sheet 30 facing the skin of a wearer and a liquid impermeable sheet being placed outside a product which does not essentially allow liquid to permeate, for example, a liquid impermeable sheet such as polyethylene which does not allow liquid to permeate at all.

Absorber 50 is provided with a fiber aggregate 52Z composed of tow that the continuous direction of fiber is aligned to the longitudinal direction. The fiber aggregate is wrapped with a liquid permeable sheet 58 like crepe paper, and super absorbent polymer is enclosed inside the wrapping sheet 58. The super absorbent polymer can exist between the fiber aggregate 52Z and the wrapping sheet 58, or in the fiber aggregate 52Z. In the both edges of the width direction of the middle in the longitudinal direction of fiber aggregate 52Z, concavity 10u narrowed toward the center in the width direction is formed. Such fiber aggregate 52Z can be produced by the foregoing method of the present invention. The concavity 10u of fiber aggregate 52Z can employ suitable shapes such as V character other than the U character of the example shown in the figure. The concave shape can be adjusted by suitably setting extension force using the foregoing production method of the present invention.

Back sheet 12A is a rectangle with wider than absorption elements, and provided outsides with an external sheet 12 of non-woven in a sand clock shape. On the other hand, liquid permeable top sheet 30 is a rectangle with wider than absorption elements, somewhat extending outwards over the side edge of absorption element, and is fixed with the back sheet 12A with a hot melt adhesive etc (fixed parts related to the present mode is denoted as symbol * including this fixed part).

A barrier cuff 60A for leg periphery protruding to the use-face side is formed in both sides of diaper. The standing cuff 60A is constructed with a side sheet composed of essentially continuous non-woven in the width direction and an elastic member, for example, one piece of rubber thread, or a plurality of pieces consisting of elastic stretch member 62 for leg periphery as shown in the figure. Side sheet 64 is not liquid permeable, but preferably essentially liquid impermeable (may be semi-permeable), for example, it may be treated with silicone to give liquid repellency to non-woven fabric.

In wearing a diaper, the diaper is worn in a ship shape, a barrier cuff 60A stands around a leg by operation of contraction force of each of elastic stretch members 62 so on. The space surrounded by the standing part of barrier cuff 60A forms a space for enclosing body liquids like urine. When body fluids are discharged in the space, the body fluids are passed through the top sheet 30 to be absorbed in the absorber 50, in this time, the standing part of barrier cuff 60A becomes barrier to prevent leakage of body fluid from both crotches.

The diaper of the mode shown in the figure has a belly side part and a back surface side part, and a stopper 130 each at both edges of either part of the belly side part and back surface side part (back surface side in the example of the figure), is a so called tape stopping paper diaper that an opening around trunk and a pair of openings around legs are formed by fixing the stopper 130 in one part with another part (target tape 74 in belly side in the example of the figure), needless to say, it may be applied to a underpants type paper diaper that both edges of belly side and back surface side are bonded beforehand and to other absorbent article of body fluid.

On the other hand, also in the present mode, in the same mode as shown in FIGS. 18 (*a*) and (*b*), it is preferable to provide a fiber aggregate for the fiber continuous direction of tow to be the longitudinal direction (back and forth direction) of product, it is also possible to provide a fiber aggregate for the fiber continuous direction of tow to be the width direction of product as the example shown in FIGS. 18 (*c*) and (*d*).

Figure 41:
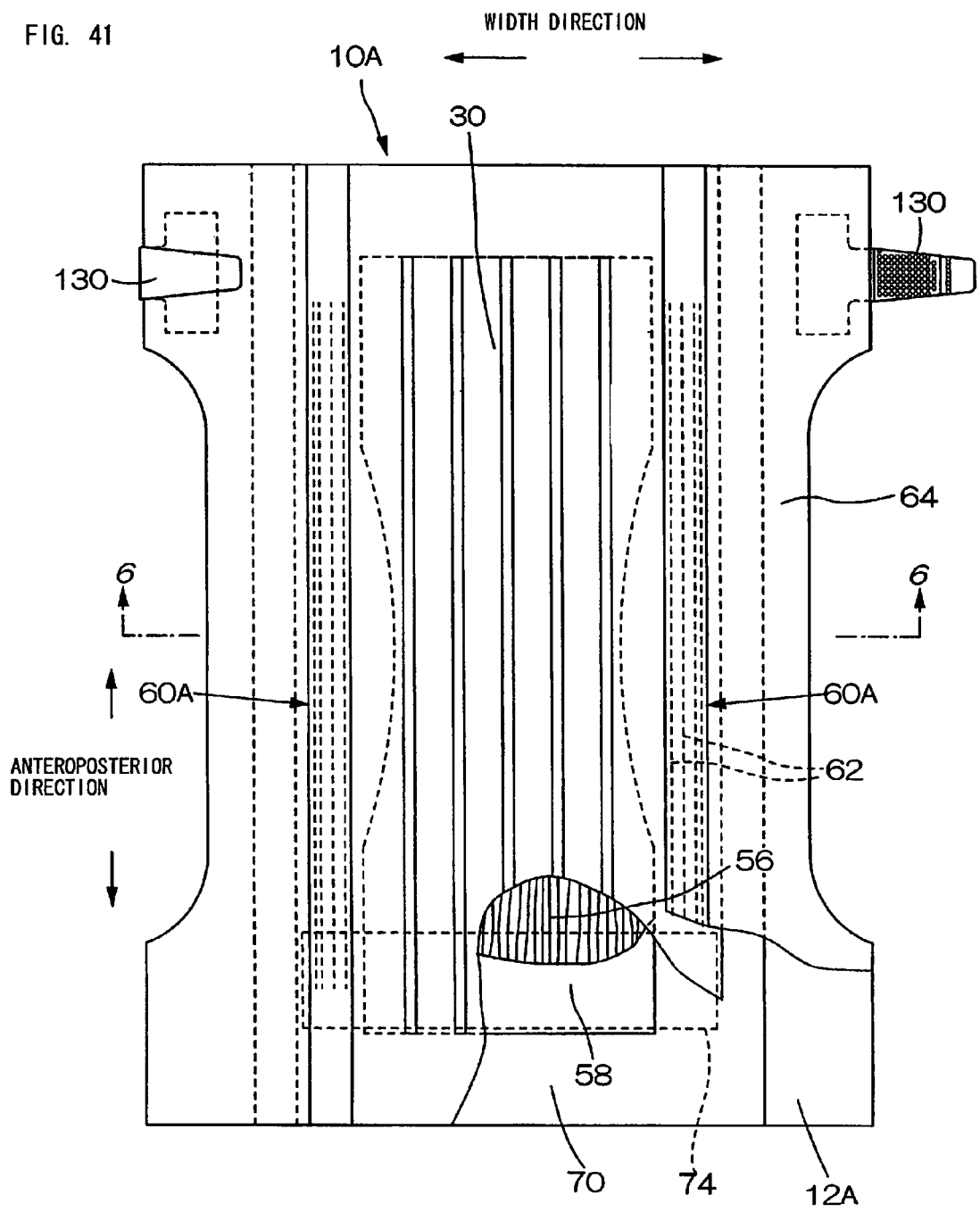
FIG. 41 is a plan view of paper diaper in a development state.
Figure 42:
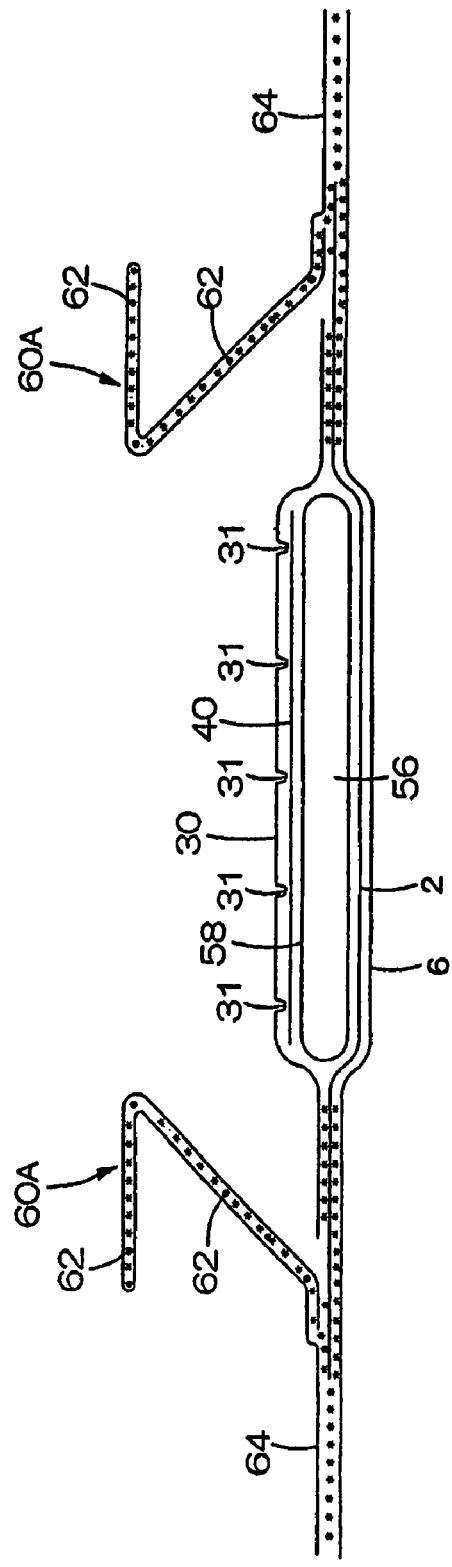
FIG. 42 is a sectional view along II-II line of FIG. 41.

As shown in FIG. 41 and FIG. 42, it is possible to provide a channel 31 of a continuous line in any one or, two or more, or all of layers provided on the surface of absorbent core 56, namely a top sheet 30, a medium sheet 40 and a wrapping sheet 58 in order to improve liquid diffusion. When the top sheet 30 is provided with the channel 31, body fluids can be diffused advantageously more quickly. Also, when the medium sheet 40 and wrapping sheet 58 are provided with the channel, body fluids can be diffused into farther place from skin, advantageously giving reduced wet feeling. From the consideration of balance between ease of production and effect, the channel 31 is preferably provided to only either top sheet 30 or medium sheet 40, or both sheets 30 and 40.

As a shape of channel 31, it can be suitably determined from the main consideration of diffusion direction of body fluid, for example, the following shapes can be adopted:

(1) A shape that channel 31 is provided along the back and forth direction of goods as shown in FIG. 41.

Figure 43:
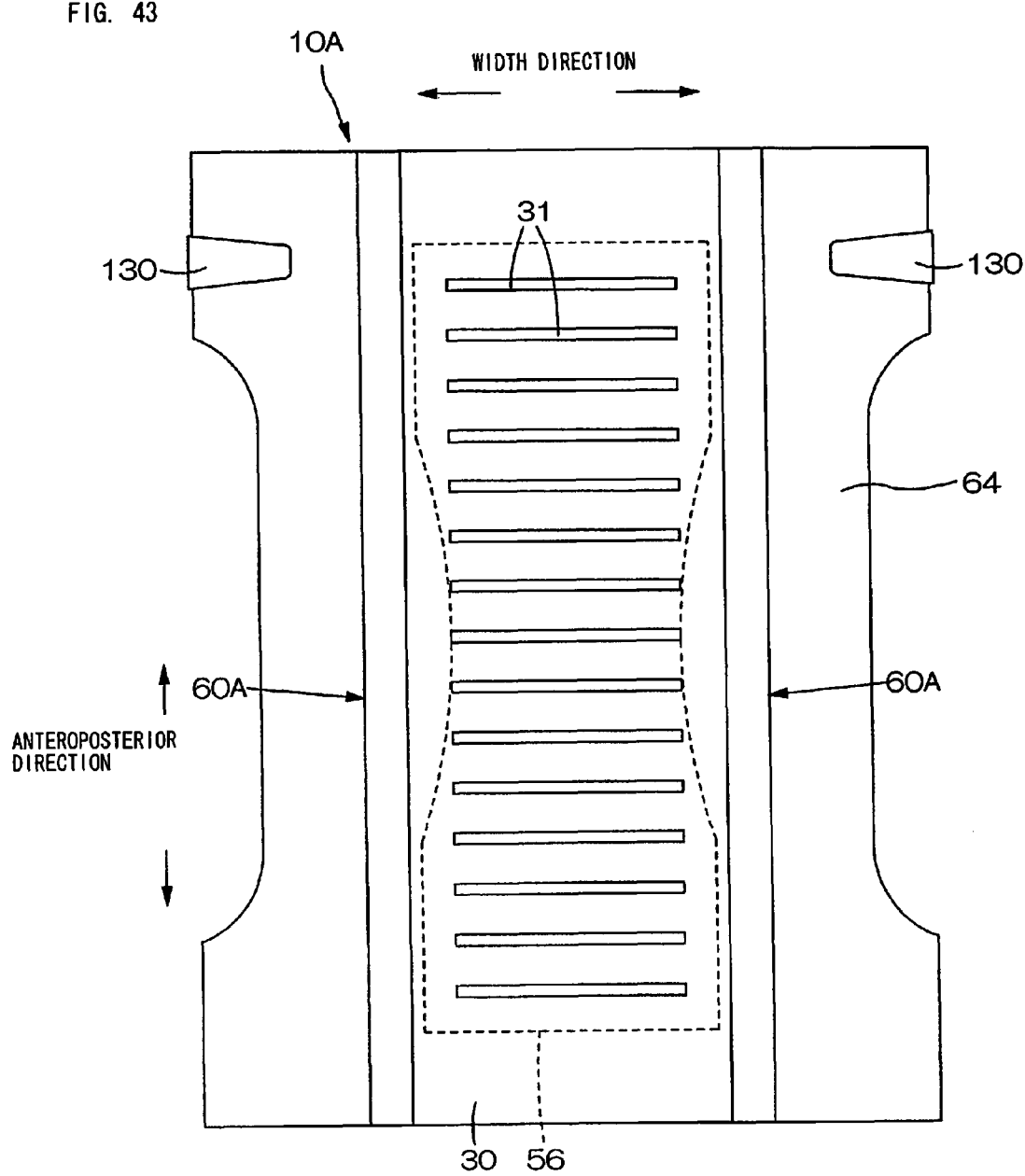
FIG. 43 is a plan view of another paper diaper example.

(2) A shape that plural rows of channel 31 is provided along the width direction of goods as shown in FIG. 43.

(3) A shape that plural rows of channel 31 is provided at suitable intervals as shown in FIG. 41 and FIG. 42.

Figure 44:
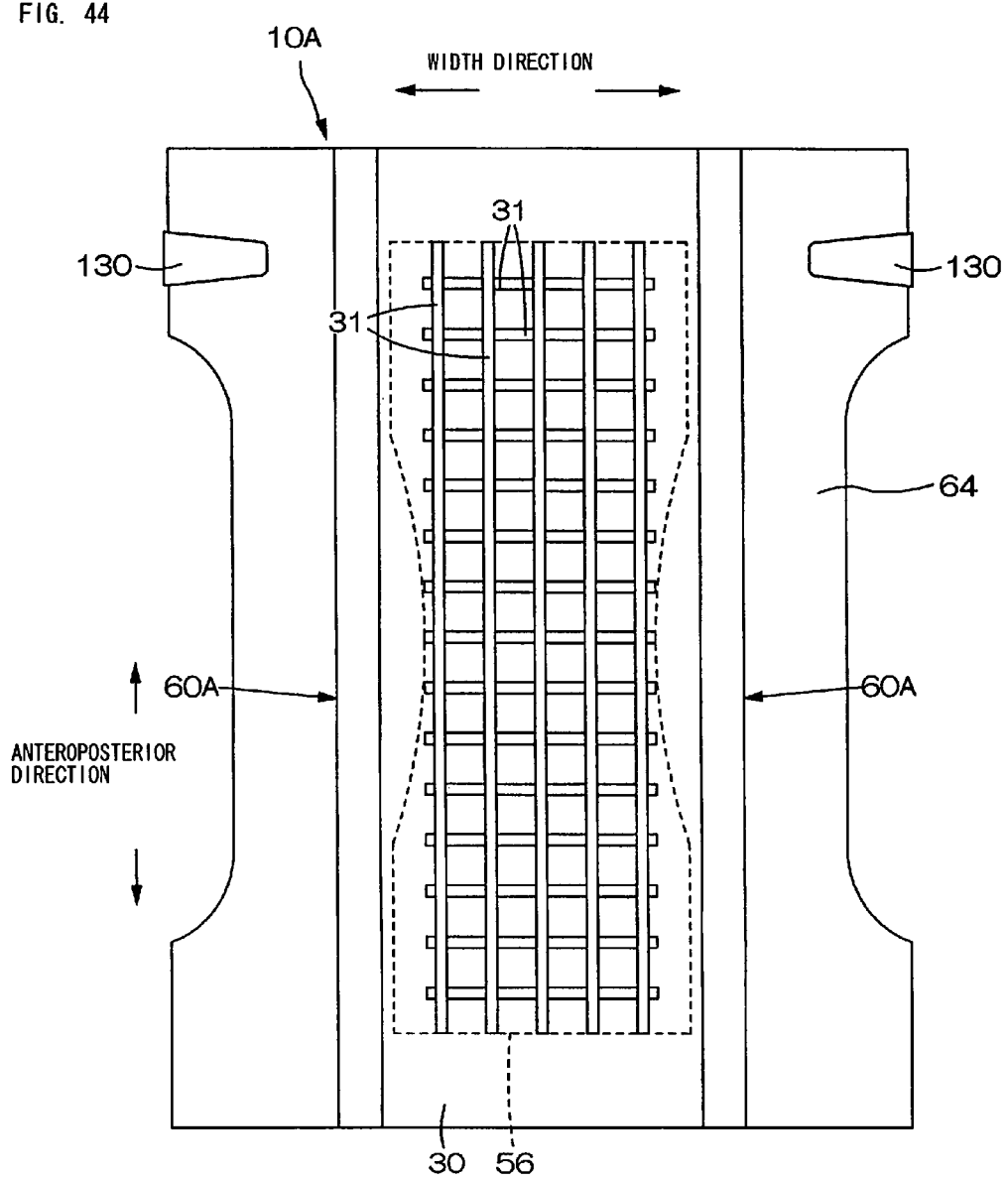
FIG. 44 is a plan view of another paper diaper example.

(4) A shape crossed so that plural rows of channel 31 are disposed along the back and forth direction of goods and plural rows of channel 31 are disposed along the width direction of goods (namely a shape in lattice with channels 31 provided) as shown in FIG. 44.

Figure 45:
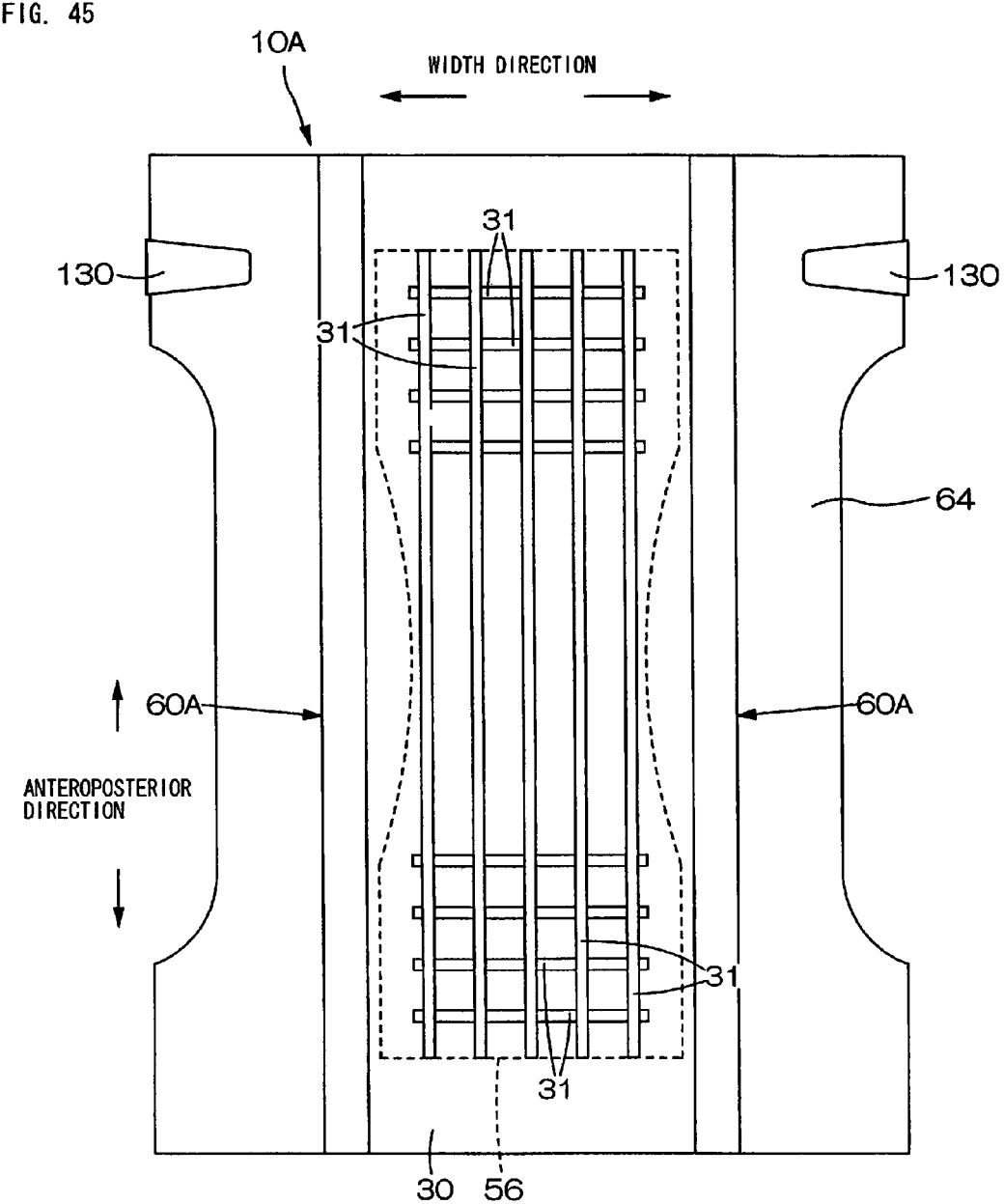
FIG. 45 is a plan view of another paper diaper example.

(5) A shape that plural rows of channel 31 are disposed along the back and forth direction of goods and channel 31 is disposed only the back and forth parts along the width direction of goods as shown in FIG. 45.

Figure 46:
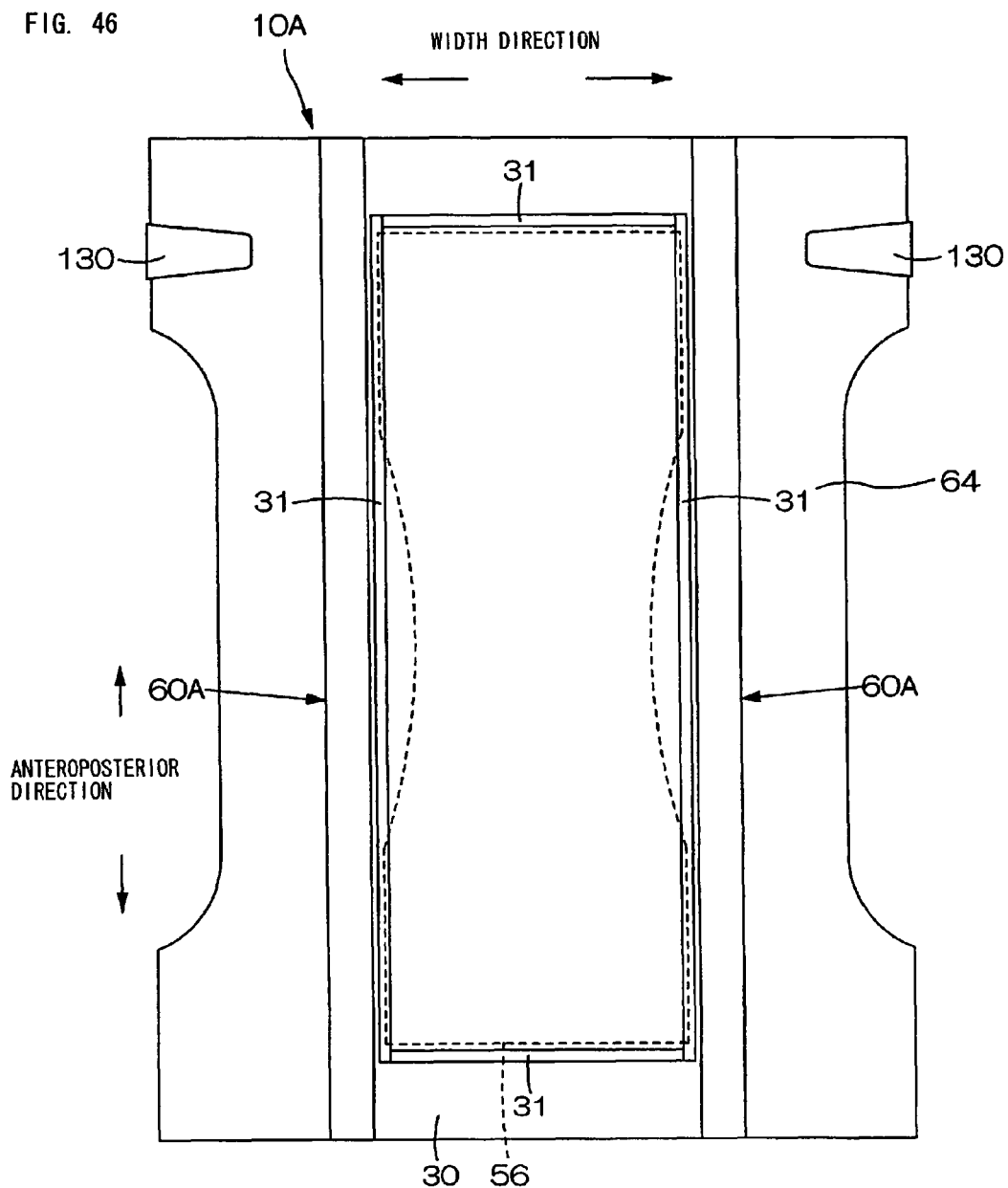
FIG. 46 is a plan view of another paper diaper example.

(6) A shape that channel 31 is provided circularly to surround an excretion place as shown in FIG. 46.

In the range of providing channel 31, it can be suitably determined from the consideration of diffusion range of body fluid, for example, the following shapes can be adopted:

(a) All or almost all of target sheet (e.g. area rate of 80% or more)

Figure 47:
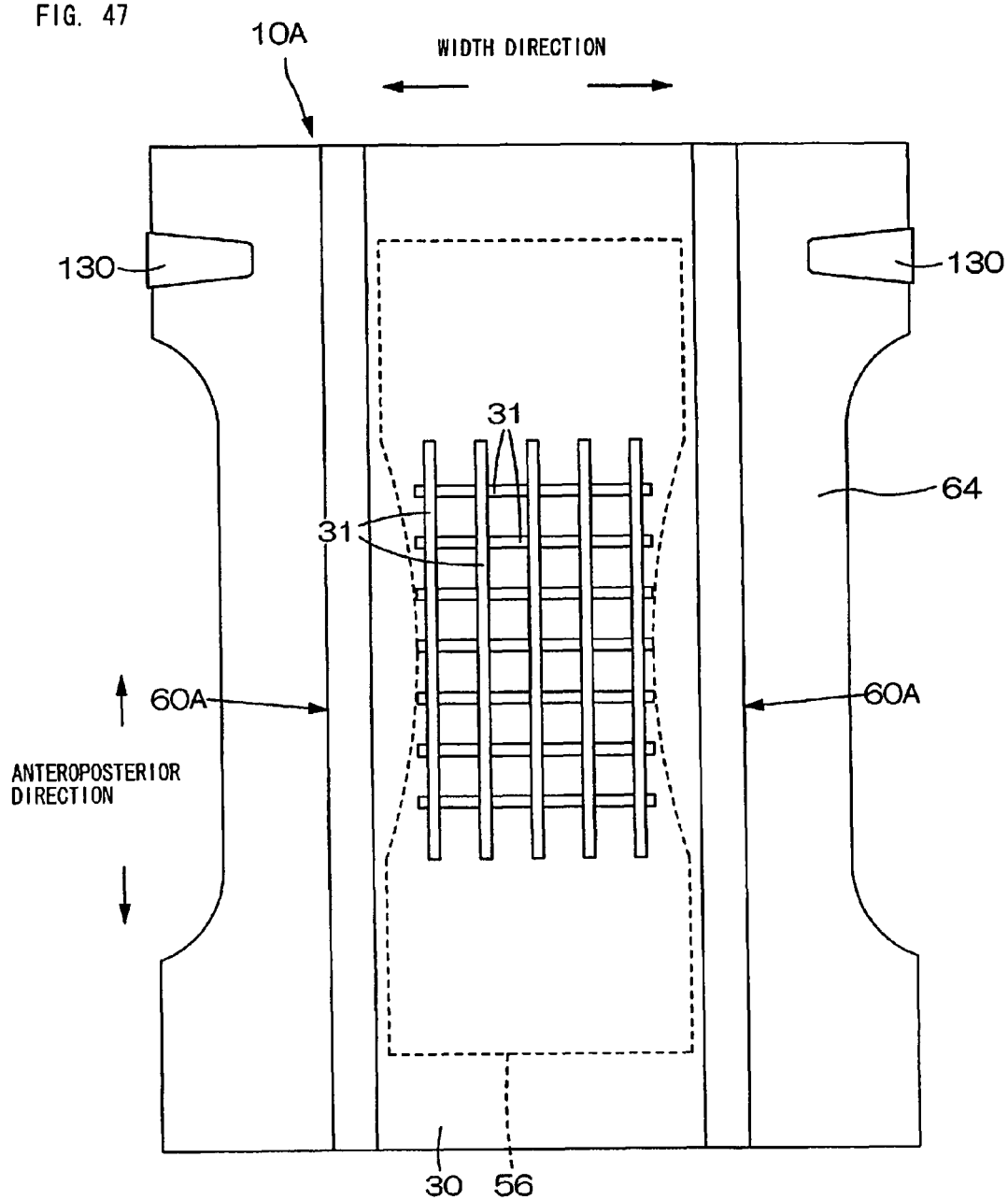
FIG. 47 is a plan view of another paper diaper example.

(b) Part of target sheet, for example, in the back and forth direction of goods or middle in the width direction or only at both edges as shown in FIG. 47.

(c) Overlap range with at least absorber 3 as shown in FIG. 41 etc.

The number of channels 31 is suitably determined, it may be one piece, a plurality of pieces, particularly 3 pieces or more are preferable, in particular, a preferable shape is to set up channels of 3 pieces or more along the back and forth direction of goods.

There can be suitably set up the length, width and depth of channel 31, and the intervals in the case where a plurality of channels are provided. These sizes cannot be categorically determined, in ordinary shapes of paper diaper and sanitary napkin, the length of channel 31 is 50 mm to 1000 mm, particularly preferably 70 mm to 700 mm. Also, the width of channel 31 is 0.5 mm to 50 mm, particularly preferably 1 mm to 20 mm. Also, the depth of channel 31 is 0.05 mm to 10 mm, particularly preferably 0.1 mm to 5 mm. Further, the intervals of channel 31 are 0.5 mm to 150 mm, particularly preferably 1 mm to 50 mm.

Figure 48:
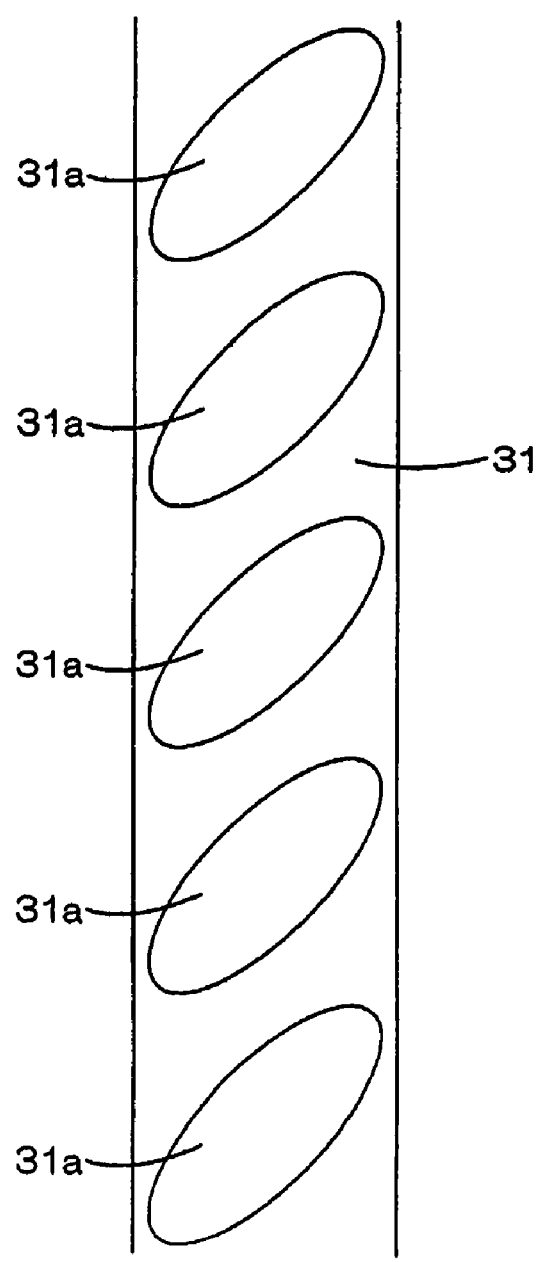
FIG. 48 is a plan view showing a channel example by compression processing.

Regarding channel 31, channel 31 may be formed in such way that a raw material itself is produced (e.g. produced in a section wave), it is preferably formed by pressure processing such as embossing of target member in a suitable production step. In this case, the channel 31 is formed by continuous line pattern, in addition thereto, a method for forming a continuous line channel 31 by adapting the pattern that a great number of punctiform compressed parts 31*a* compressed parts 31*a* as shown in FIG. 48 are overlapped for compressed parts 31*a* to come close each other.

In the case where channel 31 is provided to a plurality of sheets, it is possible to make the shape of channel 31 different. For example, channel 31 is extended along the back and forth direction of goods in a top sheet 30, and channel 31 is extended along the width direction in a medium sheet 40.

Next, other embodiment will be explained on the basis of an example of application in a tape stopping type paper diaper, needless to say, the present invention can be applied to other absorbent article of body fluid such as underpants type paper diaper underpants type paper diaper and sanitary napkin.

Figure 49:
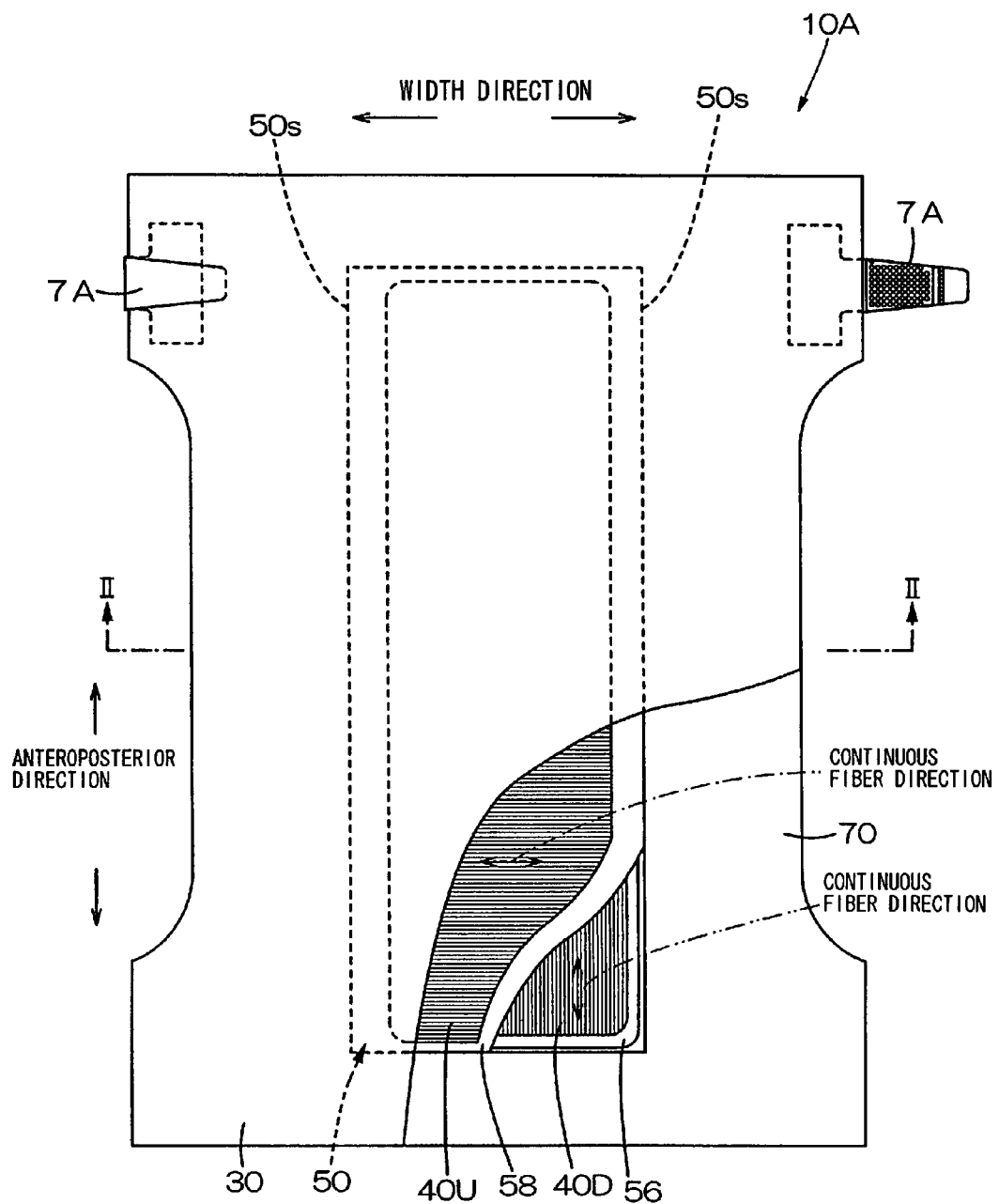
FIG. 49 is a plan view a stopping type paper diaper in another mode.
Figure 50:
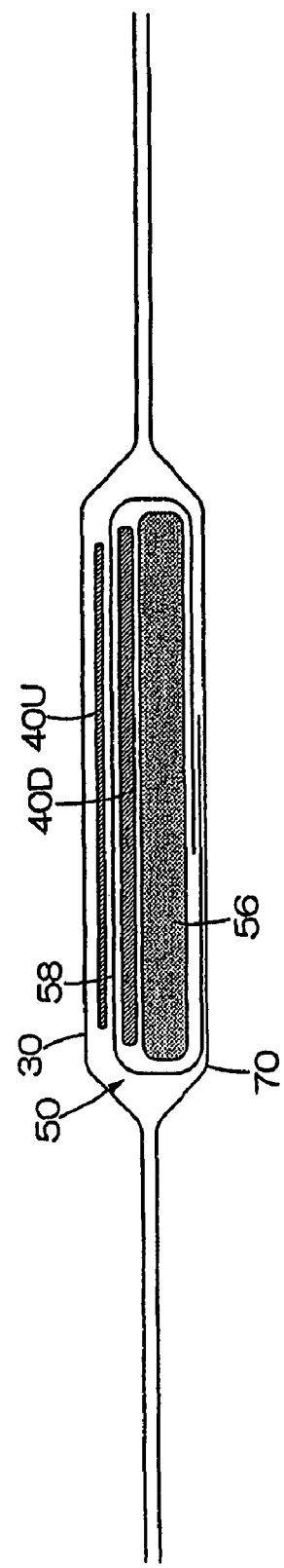
FIG. 50 is a sectional view along II-II line of FIG. 49.

FIG. 49 and FIG. 50 show stopping type paper diaper 10A as an target in the present invention. This paper diaper 10A is provided with an absorber 50 having rigidity on some level shaping a rectangle or preferably a sand clock shape placing between a liquid permeable surface (top) sheet 30 facing skin of wearer and a liquid impermeable back surface sheet 70 that does not essentially allow liquid to permeate placing outside of product.

Rear sheet 70 is a rectangle with wider than absorber 50. In the outer face, it is possible to provide an external sheet composed of non-woven fabric to improve skin touch. The back surface sheet 70 can be formed by plastic film like polyethylene film.

On the other hand, surface sheet 30 is a rectangle with wider than absorber 50, extends outwards over the side edge 50s of absorber 50, and is bonded to back surface sheet 70 with hot melt adhesives etc. The surface sheet 30 can employ various non-woven fabrics such as spun bond non-woven, air-through non-woven, SMS non-woven and point bond non-woven; plastic films such as polyethylene film; and laminate non-woven fabric laminated with plastic film and non-woven. Also, a net material that threads of nylon or polyethylene terephthalate are plain woven can be used.

A second (medium) sheet 40U is provided between surface sheet 30 and absorber 50 in order to diffuse body fluids passed through the surface sheet 30 to a wide region quickly or move them to the absorber 50 quickly. In the absorbent article of body fluid in the present mode, the second sheet 40U is composed of a fiber aggregate made of tow (hereinafter, the fiber aggregate as the second sheet is also called second fiber aggregate). This second fiber aggregate is aligned so that continuous fiber direction is along the width direction of absorbent article of body fluid, body fluids arrived to the second sheet 40U through surface sheet 30 are moved to the absorber 50 while being diffused in the width direction of absorbent article of body fluid 10A.

As an absorber 50, a fiber aggregate 40D other than the second sheet 40U (hereinafter, a fiber aggregate composing absorber is also called first fiber aggregate) is disposed in lamination on the surface sheet 30 side of absorbent core 50, it is formed in such way that these are wrapped with a liquid permeable sheet 58, for example, liquid permeable sheets such as crepe paper, non-woven fabric, a sheet with holes. The first fiber aggregate 40D is aligned on the absorbent core 56 for the continuous fiber direction to be the back and forth direction of absorbent article of body fluid, being different from the second sheet (second fiber aggregate) 40U. Therefore, body fluids arrived to the first fiber aggregate 40D through the second sheet 40U and crepe paper 58 are moved to the absorbent core 56 and absorbed/maintained therein while being diffused in the back and forth direction of absorbent article of body fluid 10A.

Namely, in the absorbent article of body fluid 10A of the present mode, the second fiber aggregate 40U and the first fiber aggregate 40D form a laminate structure between the surface sheet 30 and absorbent core 56, and the continuous fiber direction of the second fiber aggregate 40U is aligned along the width direction of absorbent article of body fluid 10A, the continuous fiber direction of the first fiber aggregate 40D is aligned along the back and forth direction of absorbent article of body fluid 10A. Thus, body fluids brought in the absorbent article of body fluid through the surface sheet 30 are first diffused in the width direction of absorbent article of body fluid 10A, and permeated into the crepe paper 58, further, diffused in the back and forth direction of the first fiber aggregate 40D to reach the absorbent core 56. Therefore, it is possible to receive body fluids in a wide region of absorbent core 56, so that there is no lowering of absorption due to the absorption of body fluid in a certain place intensively. Also, body fluids can be absorbed without loss up to every corner of absorbent core 56.

The second fiber aggregate 40U as a second sheet and the first fiber aggregate 40D as the absorber structure may be a fiber aggregate with the same construction, may be different in fiber diameter or degree of fiber opening. These can be suitably designed.

On the other hand, the absorbent core 56 includes absorptive polymer therein. Additionally, super absorbent polymer may be included in the first fiber aggregate 40D. As a preferable super absorbent polymer, there can be used carboxymethyl cellulose, polyacrylic acid and its salts, crosslinked polyacrylic acid salt, starch-acrylic acid graft copolymer, hydrolyzed product of starch-acrylic nitrile graft copolymer, crosslinked polyoxyethylene, crosslinked carboxymethyl cellulose, polyethylene oxide, partly crosslinked water-swelling polymer like polyacrylamide and isobutylene-maleic acid copolymer. It is possible to use a material that anti-blocking agent is added to suppress blocking due to moisture absorption. Also, there are super absorbent polymers with various shapes such as powder, particulate, granule, pellet, sol, suspension, gel, film and non-woven, these are usable in the present invention, in particular, particulate shape is preferably used.

Additionally, being not shown in a figure, needless to say, a technique for disposing elastic stretch members like rubber thread used in absorbent article such as stopping type paper diapers can be used in every place.

Figure 51:
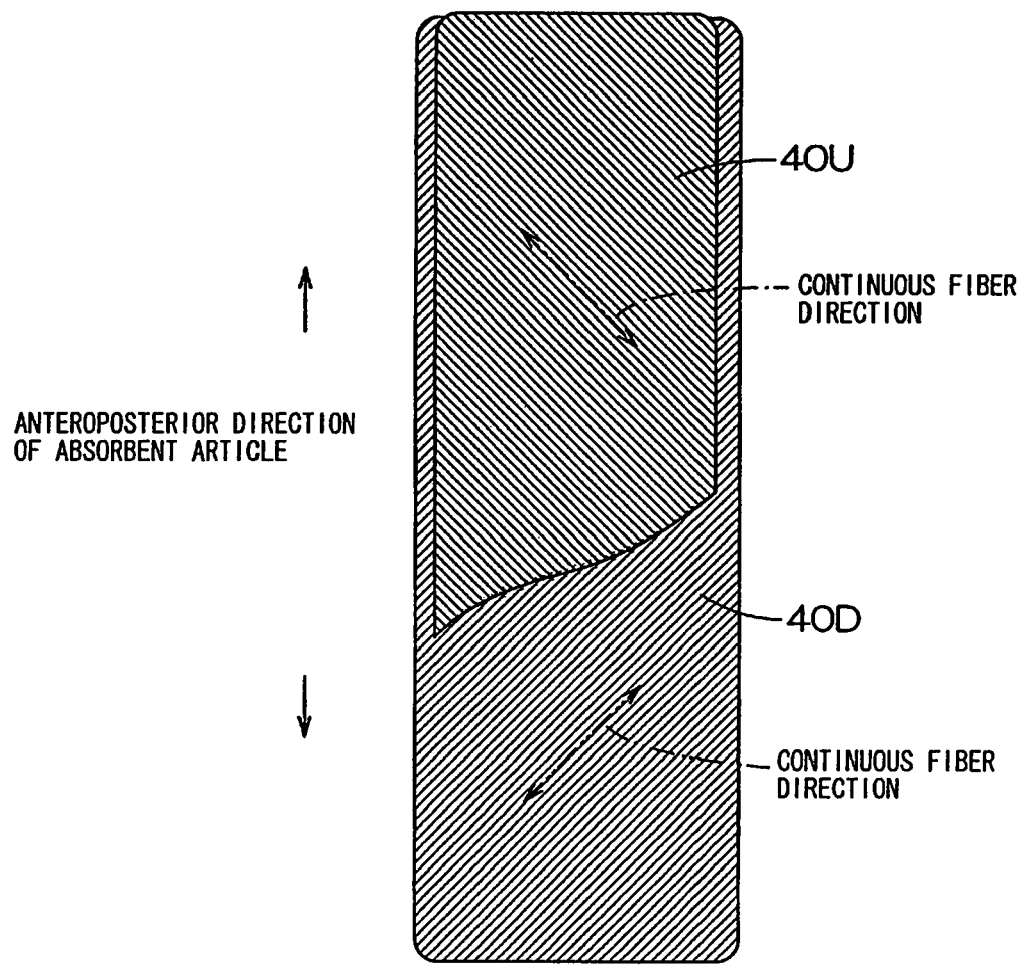
FIG. 51 is a schematic diagram showing a laminate mode of fiber aggregate layer.

In the above modes, absorbent article of body fluid 10A is composed in such way that each continuous fiber direction of second sheet (second fiber aggregate) 40U and absorber structure (first fiber aggregate) 40D is aligned in lamination to be almost perpendicular to the back and forth direction and the width directions, but the continuous fiber direction of each layer is not necessary to be perpendicular one another. In brief, fiber aggregate layers with two or more layers are provided between liquid permeable surface sheet and absorbent core, and those continuous fiber directions are merely different. For example, as shown in FIG. 51, it can be a mode which is laminated with each fiber aggregate in such way that the second fiber aggregate 40U like second sheet is aligned so that the continuous fiber direction (dashed line in the figure) is at about 45 degree left to the back and forth direction of absorbent article, the first fiber aggregate 40D like absorber structure is aligned so that the continuous fiber direction (chain double-dashed line in the figure) is at about 45 degree right to the back and forth direction of absorbent article. Also, the foregoing mode is a mode of absorbent article of body fluid provided with fiber aggregate layers of two layers of second sheet (second fiber aggregate) 40U and the first fiber aggregate 40D placed between liquid permeable surface sheet 30 and absorbent core 56, a mode may be provided with fiber aggregate layers of three layers or four layers placed between liquid permeable surface sheet 30 and absorbent core 56.

Figure 52:
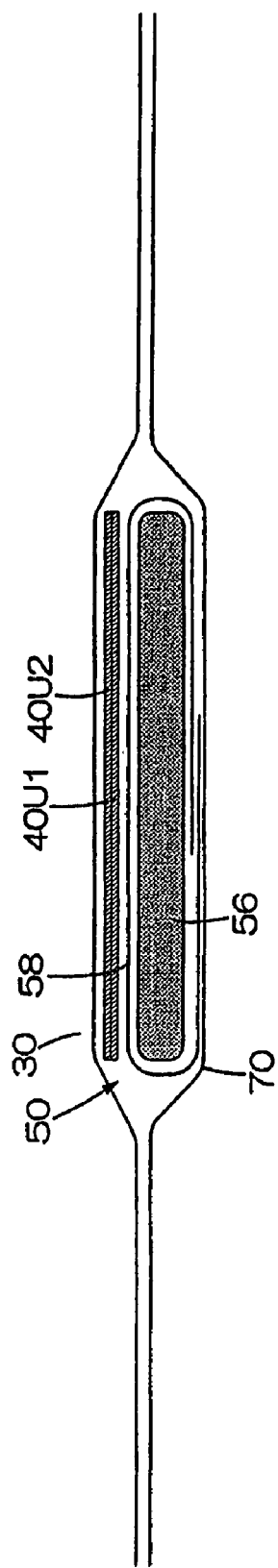
FIG. 52 is a schematic diagram of cross section of absorbent article of body fluid in another mode.

Further, in the foregoing mode, fiber aggregate layers of two layers are constructed by using a fiber aggregate in absorber structure 40D and second sheet 40U, as shown in the sectional view of FIG. 52, a mode may be provided with second sheet 40U aligned in lamination of fiber aggregates 40U1 and 40U2 with different continuous fiber directions between absorber 50 and liquid permeable surface sheet 30.

Figure 53:
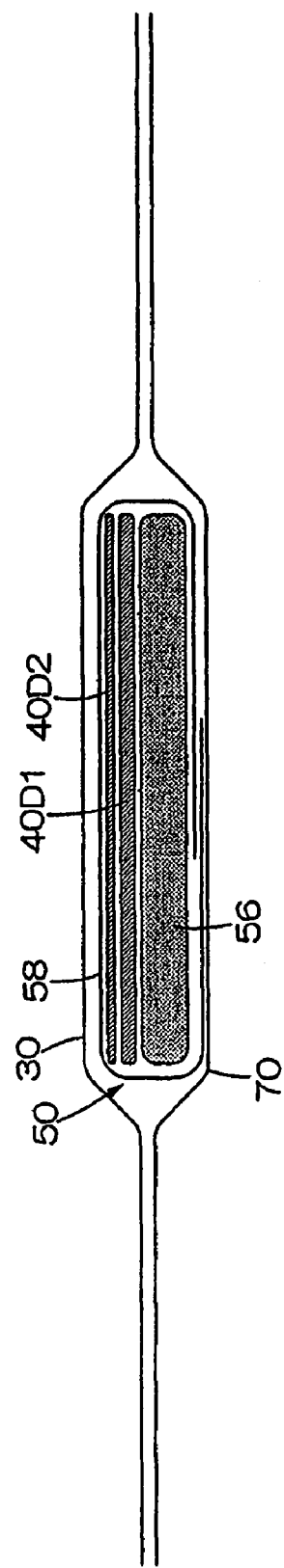
FIG. 53 is a schematic diagram of cross section of absorbent article of body fluid in another mode.

As shown in FIG. 53, a mode may be provided with absorber 50 aligned in lamination of fiber aggregates 40U1 and 40U2 with different continuous fiber directions on liquid permeable surface sheet 30 side of absorbent core 56. In this mode, not shown in the figure, a second sheet can be separately provided, as a second sheet in this case, there can be used a fiber aggregate, in addition thereto, non-woven fabric with no hole or open holes, short fiber or long fiber non-woven fabric, and mesh film. In the case of using non-woven fabric, it is possible to contain water retention fibers such as rayon or cellulose derivatives in non-woven, and to add hydrophilic agent thereto. In the case of using non-woven fabric, fiber density is preferably smaller than that of surface sheet 1, for example, fineness of more than 2.1 dtex, particularly fineness of more than 2.1 dtex, and 11.0 dtex or less can be used. As a material of non-woven fabric used in the second sheet of this mode, there can be listed polypropylene, polyethylene, polyethylene terephthalate, polyamide, nylon, rayon, vinylon, acrylic resin, in the case of a direct method, polypropylene, polyethylene terephthalate and nylon fibers can be preferably adopted. In conjugating short fibers, in association to wet method, dry method (air lay method or carding method) and spun lace method, spot bonding by heat or adhesive, intertwine by water stream or needing can be listed. A non-woven fabric made of conjugate fiber of core/shell and side-by-side structures can be also listed, as this conjugate fiber, there can be listed polyethylene terephthalate/polyethylene, polypropylene/polyethylene and polypropylene/polypropylene.

Next, the above fiber aggregate will be explained. The above fiber aggregate is composed of tow, as fiber composing the fiber aggregate composed of tow (hereinafter, simply, called tow composing fiber), for example, there can be used polysaccharides and the derivatives such as cellulose, cellulose ester, chitin and chitosan; and synthetic polymers such as polyethylene, polypropylene, polyamide, polyester, polylactamide and polyvinyl polyacetal, in particular, cellulose ester and cellulose are preferable.

As cellulose, there can be used cellulose derived from plant such as cotton, linter, wood pulp and bacteria cellulose, regenerated cellulose like rayon may be used, regenerated cellulose may be a spun fiber. The shape and size of cellulose can be selected from various sizes such as from continuous fiber that can be considered essentially as an infinite length to about several mm to several cm in major axis (e.g. 1 mm to 5 cm), fine powder with a particle diameter of about several microns (e.g. 1 to 100 μm). Cellulose may be fibrillated like beating pulp.

As cellulose ester, for example, there can be used organic acid ester such as cellulose acetate, cellulose butyrate and cellulose propionate; mixed acid ester such as cellulose acetate propionate, cellulose acetate butyrate, cellulose acetate phthalate, and cellulose acetate nitrate; and cellulose ester derivatives such as polycaprolactone graft cellulose ester. These cellulose esters can be used alone or, in two or more kinds thereof. The viscosity average degree of polymerization in cellulose ester is, for example, 50 to 900, preferably about 200 to 800. The average degree of substitution of cellulose ester is, for example, about 1.5 to 3.0 (e.g. 2 to 3).

The average degree of polymerization in cellulose ester can be, for example, 10 to 1000, preferably 50 to 900, further preferably about 200 to 800, the average degree of substitution in cellulose ester can be, for example, about 1 to 3, preferably 1 to 2.15, and further preferably about 1.1 to 2.0. The average degree of substitution in cellulose ester can be selected from the points of biodegradation etc.

As cellulose ester, organic acid ester (e.g. ester of organic acid having carbon atoms of about 2 to 4), cellulose acetate is particularly preferred. Acetylation degree of cellulose acetate is often about 43 to 62%, about 30 to 50% is particularly preferable due to good biodegradation.

Tow composing fiber may contain, for example, heat stabilizer, pigment, oil, yield improving agent, whiteness improving agent and the like.

Fineness of tow composing fiber can be, for example, 1 to 16 deniers, preferably 1 to 10 deniers, and further preferably about 2 to 8 deniers. Tow composing fiber may be non-crimped fiber, preferably crimped fiber. Degree of crimp of crimped fiber can be, for example, 5 to 75 pieces per one inch, preferably 10 to 50, and further preferably about 15 to 50. Also, there are many cases that crimped fiber uniformly crimped is used. When crimped fiber is used, a bulky and light-weight absorber can be produced and also highly integrated tow can be easily produced by intertwine of fibers. Cross section of tow composing fiber is not particularly limited, for example, may be circular, elliptical, non-circular (e.g. Y-shape, X-shape, 1-shape, R-shape) or hollow shape. Tow composing fiber can be used in tow (fiber bundle) formed by bundling filaments of 3000 to 1000000 for example, preferably 5000 to 1000000. It is preferably that fiber bundle is constructed by bundling continuous filaments of about 3000 to 1000000.

Tow is weak in intertwine of fibers, thus mainly to maintain the shape, binders capable of adhesion or thermally bonding operation can be used. The binder can employ ester based plasticizers such as triacetin, triethylene glycol diacetate, triethylene glycol dipropionate, dibutyl phthalate, dimethoxyethyl phthalate and triethyl citrate ester, in addition thereto, may employ various resin adhesives, particularly thermoplastic resins.

The thermoplastic resin is a resin exhibiting adhesion force resulting from melting and solidification, includes water insoluble or water hardly soluble resin, and water soluble resin. Water insoluble or water hardly soluble resin and water soluble resin can be in concomitant use according to need.

As the water insoluble or water hardly soluble resin that can be used, for example, there are listed olefin based homopolymer or copolymer such as polyethylene, polypropylene, ethylene-propylene copolymer and ethylene-vinyl acetate copolymer, polyvinyl acetate, acrylic resins such as polymethyl methacrylate, methyl methacrylate-acrylate copolymer, and (meth)acrylic monomer-styrene monomer copolymer; polyvinyl chloride, vinylacetate-vinylchloride copolymer, polystyrene, styrene based polymer such as copolymer of styrene type monomer with (meth)acrylic type monomer; polyesters that may be modified; polyamide such as nylon 11, nylon 12, nylon 610 and nylon 612; rosin derivatives (e.g. rosin ester); hydrocarbon resins (e.g. terpene resin, dicyclopentadiene resin, petroleum resin); hydrogenated hydrocarbon resin. These thermoplastic resins can be alone or, in two or more kinds thereof.

As the water soluble resin that can be used, there are listed various water soluble polymers, for example, polyvinyl alcohol, polyvinyl pyrrolidone, polyvinyl ether, vinyl based water soluble resins such as copolymers of vinyl monomer with copolymerizable monomer having a carboxyl group, sulfonic group or their salts; acrylic based water soluble resin, polyalkylene oxide, water soluble polyester and water soluble polyamide. These water soluble resins may be used alone or, in combination of two or more kinds thereof.

The thermoplastic resin may be added with various additives such as stabilizers like antioxidant and ultraviolet absorbing agent, filler, plasticizer, antiseptic and fungus proofing agent.

Additionally, a fiber aggregate made of the above tow can be produced by a known method, in this case, tow is opened to obtain a desired size and bulkiness in the present invention. The width of opened tow is arbitrary, for example, can be 100 to 2000 mm in width, preferably about 150 to 1500 mm. Opening tow is preferable because super absorbent polymer is easily contained. The density of fiber aggregate 10 can be adjusted by adjusting the degree of opening tow. As the above fiber aggregate, the fiber density is 0.0075 g/cm$^3$ or less in the thickness of 10 mm, particularly preferably 0.0060 to 0.0070 g/cm$^3$. When the fiber density is too high, there becomes few merit in using a fiber aggregate composed of tow, for example, weight saving and reduction of thickness become difficult. Also, the base weight of fiber aggregate 10 of the present invention is 0.0075 g/cm$^2$ or less, particularly preferably 0.0060 to 0.0070 g/m$^2$. The base weight of fiber can be adjusted by selecting tow for original fabric or by the production conditions.

As a method for opening tow, for example, there can be used a method that a tow is loaded to a plurality of opening rolls, in proceeding of tow, the width of tow is gradually enlarged, a method of opening tow by repeating strain (extension) and relaxation (construction) of tow, and a method of widening/opening tow using a compressed air.

EXAMPLES

Experiment 1

Using a fiber aggregate without containing super absorbent polymer (base weight of 0.000 g/cm$^2$) and a fiber aggregate with super absorbent polymer of 0.020 g/cm$^2$, cutting was repeated until the cutter blade was broken. As a result, it has been found that cutting in a place containing no super absorbent polymer at all or containing almost no super absorbent polymer can lengthen a life of cutter blade by about 30% at the maximum.

Experiment 2

Regarding a underpants-type paper diaper provided with a absorber produced using a fiber aggregate that tow of cellulose diacetate fiber was opened (Example and Comparative example), an ordinary absorber using shot fiber pulp and a product thereof (Conventional example), the following measurements were conducted. The results are shown in Table 5 and Table 6.

Figure 27:
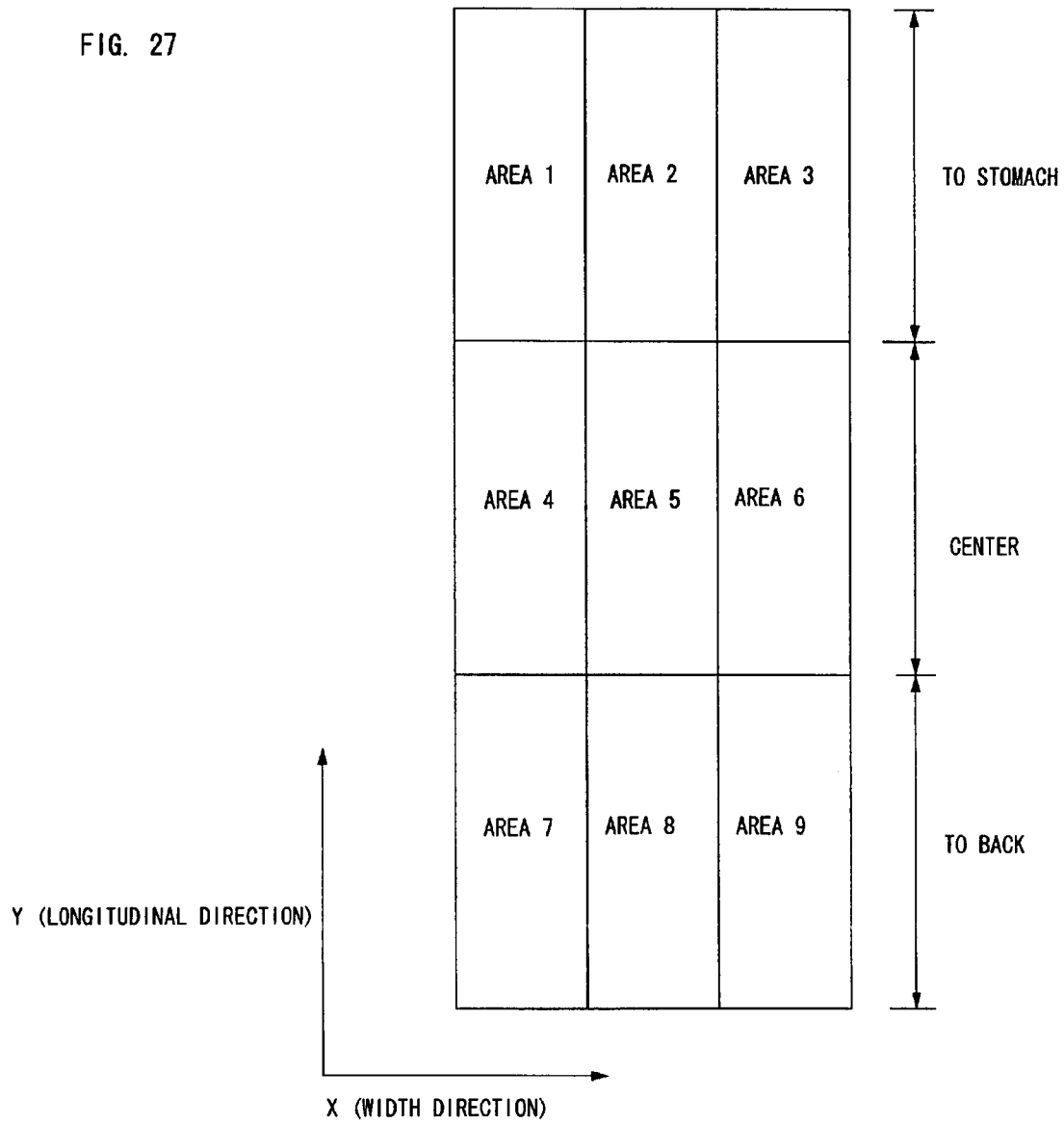
FIG. 27 is a brief overview explaining the directions of absorber.

For the base weight of super absorbent polymer particles (SAP), as shown in FIG. 27, the plan project area of target absorber is equally divided into three in the width direction and equally divided into three in the longitudinal direction to give nine divided areas, the weight of super absorbent polymer particles to each area is defined as a dispersion density.

Also, measuring methods in the Table are as follows:

Measurement for the Amount of Water Absorption of Super Absorbent Polymer Particle To a beaker of 1 liter with a stirrer, 500.00±0.10 g of 0.9% aqueous sodium chloride (prepared by dissolving 9.00 g of sodium chloride of reagent chemical in 991.0 g of ion-exchanged water) is loaded, 2.0000±0.0002 g of sample is added thereto while stirring the liquid with a magnetic stirrer, being covered with Saran Wrap for 1 hour.

The content of beaker is filtered through a standard sieve (38 μm, 200 mmΦ×45 mm), gel left on the sieve is dewatered with a Teflon plate, allowed to stand for 15 minutes, the weight A of gel left on the sieve is measured, and the amount of water absorption is calculated by the following formula:

$$C = A/S \tag{1}$$

wherein C is the amount of water absorption for fresh (g/g), A is a weight of gel left on sieve (g), and S is a weight of sample (g).

Figure 28:
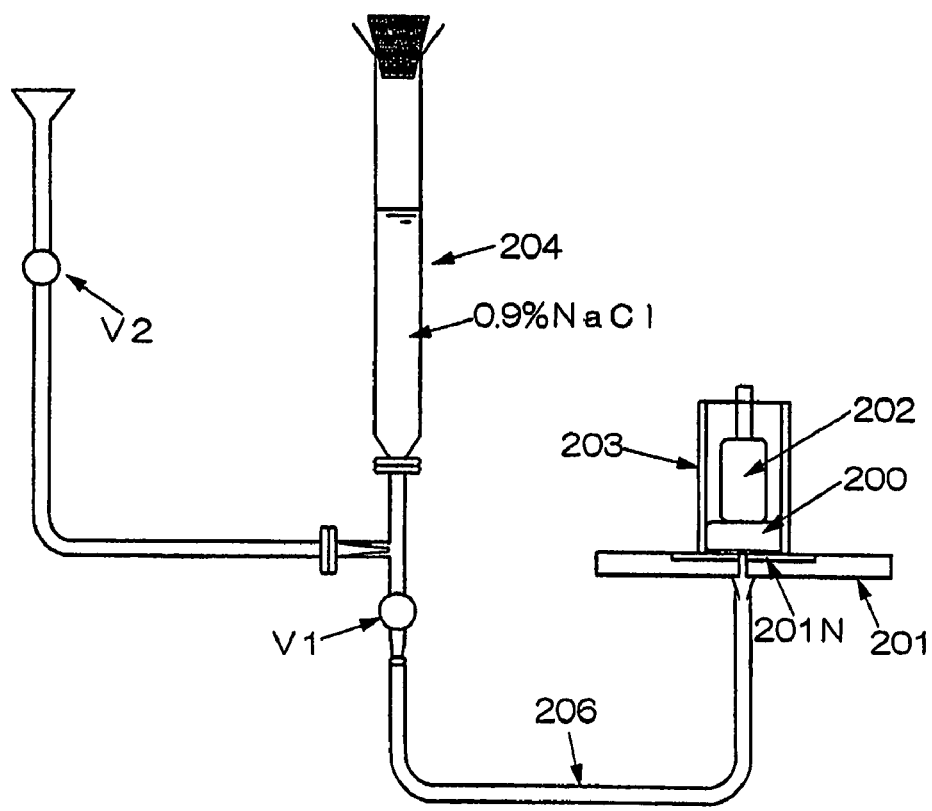
FIG. 28 is an explanatory drawing showing a test apparatus.

Measurement for the Amount of Water Absorption of Super Absorbent Polymer Particle Under Pressure As shown in FIG. 28, a cylinder of acrylic resin 203 (inner diameter of 2 cm, height of 5 cm, bottom surface equipped with nylon net 201N of 75 μm) centered to a through-bore ups and downs in the center of support stand 201 is stood up, 0.100±0.0002 g of sample 200 is loaded in the cylinder 203, a cylindrical weight 202 (diameter of 1.9 cm, weight of 120 g) is placed on the sample 200.

An exhaust of burette 204 is connected with downside opening of through-bore of support stand 201 through a conduit 206, scale markings (ml) before opening valves V1 and V2, and after 30 minutes are read.

The amount of water absorption under pressure is calculated by the following formula:

$$C = (A-B)/S \tag{3}$$

wherein C is the amount of water absorption under pressure (ml/g), A is a scale marking (ml) after 30 minutes from start of water absorption, B is a scale marking (ml) before water absorption, and S is a weight of sample (g).

Measurement for Gel Strength of Super Absorbent Polymer Particle 20.0 g of urea, 8.0 g of sodium chloride, 0.3 g of calcium chloride, 0.8 g of magnesium sulfate, 970.9 g of ion-exchanged water and 0.25 g of ferrous sulfate are mixed, an artificial urine (iron ion of 50 ppm) of 1 liter as a whole is prepared.

To a beaker of 100 milliliter with a stirrer, 49±0.1 g of artificial urine containing 50 ppm of iron ion is added, and stirred using a magnetic stirrer. A sample of 1.0000±0.0002 g is weighed out, poured into vortex in the beaker, stirred until vortex disappears and liquid level becomes horizontal.

Gel generated is allowed to stand in a box with constant temperature and humidity at 40° C. and 60% RH for 3 hours.

After being immersed in tank with constant temperature at 25° C. for 5 minutes, gel strength is measured by a Neocard meter. The measurement is converted into a unit by the following formula to calculate gel strength (Pa):

$$C = A \times 0.1 \tag{4}$$

wherein C is gel strength (Pa), A is a gel strength (dyne/cm$^2$) obtained by Neocard meter, and 0.1 is a constant.

Measurement for the Amount of Back Flow in Diaper State

A top sheet is placed on an absorber cut to 100 mm×300 mm, four sides are sealed to prepare a sample.

A cylindrical instrument of 27 mm in inner diameter (support part 150 mm×150 mm) is placed in the center of sample. The cylindrical instrument is weighted if necessary.

Artificial urine of 50 cc is dripped three times at intervals of 10 minutes.

After 10 minutes from the third dripping, filter paper (ADVANTEC No. 2, 10 cm×10 cm, in piles of 30 pieces) is placed thereon, 5 kg of weight is loaded for 10 seconds, then, the weight of kitchen paper is measured, subtracted by the weight of kitchen paper before absorption measured beforehand to calculate the amount of artificial urine moved into kitchen paper, which is defined as an amount of back flow (g).

Measurement of Absorption Speed in Diaper State

There is used a U-shaped instrument with fill port formed in the center in the width direction at the bottom being made from U-shaped plate on the assumption of from crotch to buttock.

An absorber in a sample diaper is marked at the center position in the longitudinal direction, this marked position is fit in the fill port, and the sample is fixed in the outer face of U-shaped instrument.

The U-shaped instrument that the sample was fixed is placed on a hammock not so as to slant. A weight having a through-bore in the center (1 kg, 10 cm×10 cm) is placed on the U-shaped instrument. In this case, the through-bore of the weight is fit in the fill port of U-shaped instrument.

The foregoing urine of 100 cc is injected into the sample through the through-bore of the weight and fill port of U-shaped instrument, a time required for total absorption is measured, which is defined as an absorption speed (second).

Sensory Evaluation of Resilience

A sample of paper diaper in a common way except for absorber was produced using each absorber. There were prepared a sample not compressed after production and one unwrapped after wrapping in a common shape under compression, resilience was evaluated through visual check and hand feeling by 20 persons being tested. As a result, the evaluations with high resilience and sufficient flexibility were obtained as compared with the conventional example as a standard (expressed as ○ in the table).

Evaluation of Absorption Performance

By preparing dummy dolls of L size for man and women, in each state lying on one back and one's stomach, it was evaluated as the number of roll over until leakage occurs when 100 cc of artificial urine was injected at an injection speed of 12.5 cc/min.

TABLE 5

| | | Comparative Example 1 | Example 1 | Example 2 | Example 3 | Example 4 | Example 5 | Example 6 |
|---|---|---|---|---|---|---|---|---|
| Super absorbent polymer | SAP used amount[g] | 11 | 11 | 11 | 11 | 11 | 11 | 11 |
| | Absorption amount | 52 | 52 | 52 | 52 | 52 | 52 | 52 |
| | Absorption speed | 39 | 39 | 39 | 39 | 39 | 39 | 39 |
| | Absorption amount under pressure | 33 | 33 | 33 | 33 | 33 | 33 | 33 |
| | Gel strength | 1000 | 1000 | 1000 | 1000 | 1000 | 1000 | 1000 |
| Fiber aggregate | kinds | Acetate tow | Acetate tow | Acetate tow | Acetate tow | Acetate tow | Acetate tow | Acetate tow |
| | Fiber used amount[g] | 3.1 | 3.1 | 3.1 | 3.1 | 3.1 | 3.1 | 3.1 |
| Absorber | Area[$m^2$] | 0.0553 | 0.0553 | 0.0553 | 0.0553 | 0.0553 | 0.0553 | 0.0553 |
| | Thickness[mm] | 1.5 | 1.5 | 1.5 | 1.5 | 1.5 | 1.5 | 1.5 |
| | Fiber basis weight[g/$m^2$] | 56 | 56 | 56 | 56 | 56 | 56 | 56 |
| | SAP basis weight[g/$m^2$] | | | | | | | |
| | Area 1 | 199 | 278 | 159 | 159 | 199 | 199 | 199 |
| | Area 2 | 199 | 278 | 159 | 159 | 199 | 199 | 199 |
| | Area 3 | 199 | 278 | 159 | 159 | 199 | 199 | 199 |
| | Area 4 | 199 | 159 | 278 | 159 | 199 | 199 | 199 |
| | Area 5 | 199 | 159 | 278 | 159 | 199 | 199 | 199 |
| | Area 6 | 199 | 159 | 278 | 159 | 199 | 199 | 199 |
| | Area 1 | 199 | 159 | 159 | 278 | 199 | 199 | 199 |
| | Area 8 | 199 | 159 | 159 | 278 | 199 | 199 | 199 |
| | Area 9 | 199 | 159 | 159 | 278 | 199 | 199 | 199 |
| | average | 199 | 199 | 199 | 199 | 199 | 199 | 199 |
| | Z directional position of SAP | uniform | uniform | uniform | uniform | Near to skin side | Near to backside | medium |

| | | Example 7 | Example 8 | Example 9 | Example 10 | Conventional Example 1 | Conventional Example 2 |
|---|---|---|---|---|---|---|---|
| Super absorbent polymer | SAP used amount[g] | 11 | 11 | 11 | 21 | 11 | 11 |
| | Absorption amount | 52 | 52 | 52 | 52 | 53 | 53 |
| | Absorption speed | 39 | 39 | 39 | 39 | 45 | 45 |
| | Absorption amount under pressure | 33 | 33 | 33 | 33 | 33 | 33 |
| | Gel strength | 1000 | 1000 | 1000 | 1000 | 700 | 700 |
| Fiber aggregate | kinds | Acetate tow | Acetate tow | Acetate tow | Acetate tow | pulp | pulp |
| | Fiber used amount[g] | 3.1 | 3.1 | 3.1 | 3.1 | 9 | 3.9 |
| Absorber | Area[$m^2$] | 0.0553 | 0.0553 | 0.0553 | 0.0553 | 0.0553 | 0.0553 |
| | Thickness[mm] | 1.5 | 1.5 | 1.5 | 1.5 | 3.5 | 1.5 |
| | Fiber basis weight[g/$m^2$] | 56 | 56 | 56 | 56 | 163 | 70 |
| | SAP basis weight[g/$m^2$] | | | | | | |
| | Area 1 | 159 | 159 | 159 | 380 | 199 | 199 |
| | Area 2 | 159 | 159 | 159 | 380 | 199 | 199 |
| | Area 3 | 159 | 159 | 159 | 380 | 199 | 199 |
| | Area 4 | 278 | 278 | 278 | 380 | 199 | 199 |
| | Area 5 | 278 | 278 | 278 | 380 | 199 | 199 |
| | Area 6 | 278 | 278 | 278 | 380 | 199 | 199 |

TABLE 5-continued

| | | | | | | |
|---|---|---|---|---|---|---|
| Area 1 | 159 | 159 | 159 | 380 | 199 | 199 |
| Area 8 | 159 | 159 | 159 | 380 | 199 | 199 |
| Area 9 | 159 | 159 | 159 | 380 | 199 | 199 |
| average | 199 | 199 | 199 | 380 | 199 | 199 |
| Z directional position of SAP | uniform | uniform | uniform | uniform | uniform | uniform |

TABLE 6

| | | Comparative example 1 | Example 1 | Example 2 | Example 3 | Example 4 | Example 5 | Example 6 |
|---|---|---|---|---|---|---|---|---|
| Wrapping sheet | | present | present | present | present | present | present | present |
| Support sheet | | present | present | present | present | present | present | absent |
| Medium sheet | | present | present | present | present | present | present | present |
| Absorption performance | Male dummy laid on its back[number] | 4 | 4 | 4 | 5 | 4 | 4 | 4 |
| | Male dummy laid on its stomach [number] | 2 | 3 | 2 | 1 | 2 | 2 | 2 |
| | Female dummy laid on its back[number] | 3 | 2 | 4 | 4 | 3 | 3 | 3 |
| | Female dummy laid on its stomach [number] | 3 | 4 | 4 | 2 | 3 | 3 | 3 |
| | Back flow amount[g] | 3.0 | 4.0 | 2.2 | 4.0 | 2.0 | 3.5 | 3.3 |
| | Absorption speed[sec] | 263 | 295 | 231 | 292 | 261 | 199 | 268 |
| Shingly feel | Sensory | ◎ | ◎ | ◎ | ◎ | ◎ | ◎ | ◎ |
| Resilience (softness) | Sensory | ◎ | ◎ | ◎ | ◎ | ◎ | ◎ | ◎ |

| | | Example 7 | Example 8 | Example 9 | Example 10 | Conventional example 1 | Conventional example 2 |
|---|---|---|---|---|---|---|---|
| Wrapping sheet | | present | present | present | present | present | present |
| Support sheet | | Present large elasticity | Present small elasticity | absent | present | absent | absent |
| Medium sheet | | present | present | absent | present | present | present |
| Absorption performance | Male dummy laid on its back[number] | 4 | 4 | 4 | 5 | 4 | 3 |
| | Male dummy laid on its stomach [number] | 2 | 2 | 2 | 3 | 2 | 1 |
| | Female dummy laid on its back[number] | 4 | 4 | 4 | 4 | 3 | 2 |
| | Female dummy laid on its stomach [number] | 4 | 4 | 4 | 4 | 3 | 2 |
| | Back flow amount[g] | 2.1 | 2.4 | 2.2 | 1.9 | 7.0 | 7.3 |
| | Absorption speed[sec] | 222 | 241 | 332 | 202 | 238 | 328 |
| Shingly feel | Sensory | ◎ | ○ | Δ | Δ | ◎ | X |
| Resilience (softness) | Sensory | Δ | ○ | Δ | ○ | X | X |

Wrapping sheet: all are crepe papers 20 gsm
Support sheet is present, and medium sheet is present: air through non-woven cloth (30 gsm, PE/PET 2.2 dtex, fiber length 44 mm, eccentric 50%, durable and hydrophilic, PE/PET 2.8 dtex, fiber length 51 mm, eccentric and hollow 50%, durable and hydrophilic, manufactured by Fukuron Corporation) is used (elastic degree B 0.300 gfc m$^2$/cm)
Support sheet of example 7: air through non-woven cloth (50 gsm, PE/PP 5.6 dtex, crimped fiber length 51 mm, water repellent, manufactured by Fukuron Corporation) is used (elastic degree B 0.850 gfc m$^2$/cm)
holding sheet of example 8: (SMMS, 13 gsm, PP 100%, manufactured by TSI Corporation) is used (elastic degree B 0.03 gfc m$^2$/cm)
L size is used in dummy test
"large elasticity" means that elasticity is excessively large, and "small elasticity" means that elastic degree is excessively small.

Experiment 3

As shown in Table 7, for an absorber of the present invention using a fiber aggregate made of tow of cellulose acetate fiber (Example), an ordinary absorber by using short fiber pulp (Conventional example), and an absorber not satisfying the condition of the present invention in spite of using a fiber aggregate made of tow of cellulose acetate fiber, the following measurements were conducted. Additionally, the evaluation results were also shown in FIG. 7.

Also, measuring methods in the Table are as follows:

Measurement for the Amount of Water Absorption of Super Absorbent Polymer

To a beaker of 1 liter with a stirrer, 500.00±0.10 g of 0.9% aqueous sodium chloride (prepared by dissolving 9.00 g of sodium chloride of reagent chemical in 991.0 g of ion-exchanged water) is loaded, 2.0000±0.0002 g of sample is added thereto while stirring the liquid with a magnetic stirrer, being covered with Saran Wrap for 1 hour.

The content of beaker is filtered through a standard sieve (38 μm, 200 mmΦ×45 mm), gel left on the sieve is dewatered with a Teflon plate, allowed to stand for 15 minutes, the weight A of gel left on the sieve is measured, and the amount of water absorption is calculated by the following formula:

$$C=A/S \qquad (1)$$

wherein C is the amount of water absorption for fresh (g/g), A is a weight of gel left on sieve (g), and S is a weight of sample (g).

Measurement for the Amount of Water Retention of Super Absorbent Polymer

To a stainless steel container, 0.9% aqueous sodium chloride is loaded in about 80% thereof.

A sample of 2.0000±0.0002 g is precisely weighed out, placed into a cotton bag (cotton broad count 60, 100 mm×200 mm), then, about 100 ml of 0.9% aqueous sodium chloride is poured into the cotton bag, simultaneously, the whole is immersed in the aqueous solution in the stainless steel container.

The upper part of cotton bag is bound with a rubber band, after immersion for 15 minutes, followed by dewatering with a spin dryer (167G) for 1 minute to measure the weight of cotton bag and gel weight.

The same operation is conducted without placing a sample, blank weight of cotton bag in wet condition is measured.

The amount of water retention is calculated by the following formula:

$$C=(A-B)/S \qquad (2)$$

wherein C is the amount of water retention (g/g), A is a weight of cotton bag and gel (g), B is a blank weight of cotton bag in wet condition (g), and S is a weight of sample (g).

Measurement for Absorption Speed of Super Absorbent Polymer

To a beaker of 100 milliliter with a stirrer, 50.00±0.01 g of 0.9% aqueous sodium chloride is added, maintained at 25±0.2° C. in a tank with a constant temperature.

The solution is stirred at rotating speed 600±10 rpm using a magnetic stirrer and a tachometer. A sample of 2.0000±0.0002 g is weighed out, poured into vertex in the beaker, simultaneously, measurement of time is started using a stop watch. Time until the vertex disappears and liquid level becomes horizontal is recorded, which is defined as an absorption speed.

Measurement for the Amount of Water Absorption of Super Absorbent Polymer Under Pressure As shown in FIG. 28, a cylinder of acrylic resin 203 (inner diameter of 2 cm, height of 5 cm, bottom surface equipped with nylon net 201N of 75 μm) centered to a through-bore ups and downs in the center of support stand 201 is stood up, 0.100±0.0002 g of sample 200 is loaded in the cylinder 203, a cylindrical weight 202 (diameter of 1.9 cm, weight of 120 g) is placed on the sample 200.

An exhaust of burette 204 is connected with downside opening of through-bore of support stand 201 through a conduit 206, scale markings (ml) before opening valves V1 and V2, and after 30 minutes are read.

The amount of water absorption under pressure is calculated by the following formula:

$$C=(A-B)/S \qquad (3)$$

wherein C is the amount of water absorption under pressure (ml/g), A is a scale marking (ml) after 30 minutes from start of water absorption, B is a scale marking (ml) before water absorption, and S is a weight of sample (g).

Measurement for Gel Strength of Super Absorbent Polymer 20.0 g of urea, 8.0 g of sodium chloride, 0.3 g of calcium chloride, 0.8 g of magnesium sulfate, 970.9 g of ion-exchanged water and 0.25 g of ferrous sulfate are mixed, an artificial urine (iron ion of 50 ppm) of 1 liter as a whole is prepared.

To a beaker of 100 milliliter with a stirrer, 49±0.1 g of artificial urine containing 50 ppm of iron ion is added, and stirred using a magnetic stirrer. A sample of 1.0000±0.0002 g is weighed out, poured into vortex in the beaker, stirred until vortex disappears and liquid level becomes horizontal.

Gel generated is allowed to stand in a box with constant temperature and humidity at 40° C. and 60% RH for 3 hours.

After being immersed in tank with constant temperature at 25° C. for 5 minutes, gel strength is measured by a Neocard meter. The measurement is converted into a unit by the following formula to calculate gel strength (Pa):

$$C=A\times0.1 \qquad (4)$$

wherein C is the gel strength (Pa), A is a gel strength (dyne/cm$^2$) obtained by Neocard meter, and 0.1 is a constant.

Measurement for the Amount of Absorption Under Pressure in Diaper State

First, a weight of sample before absorption is measured.

Figure 29:
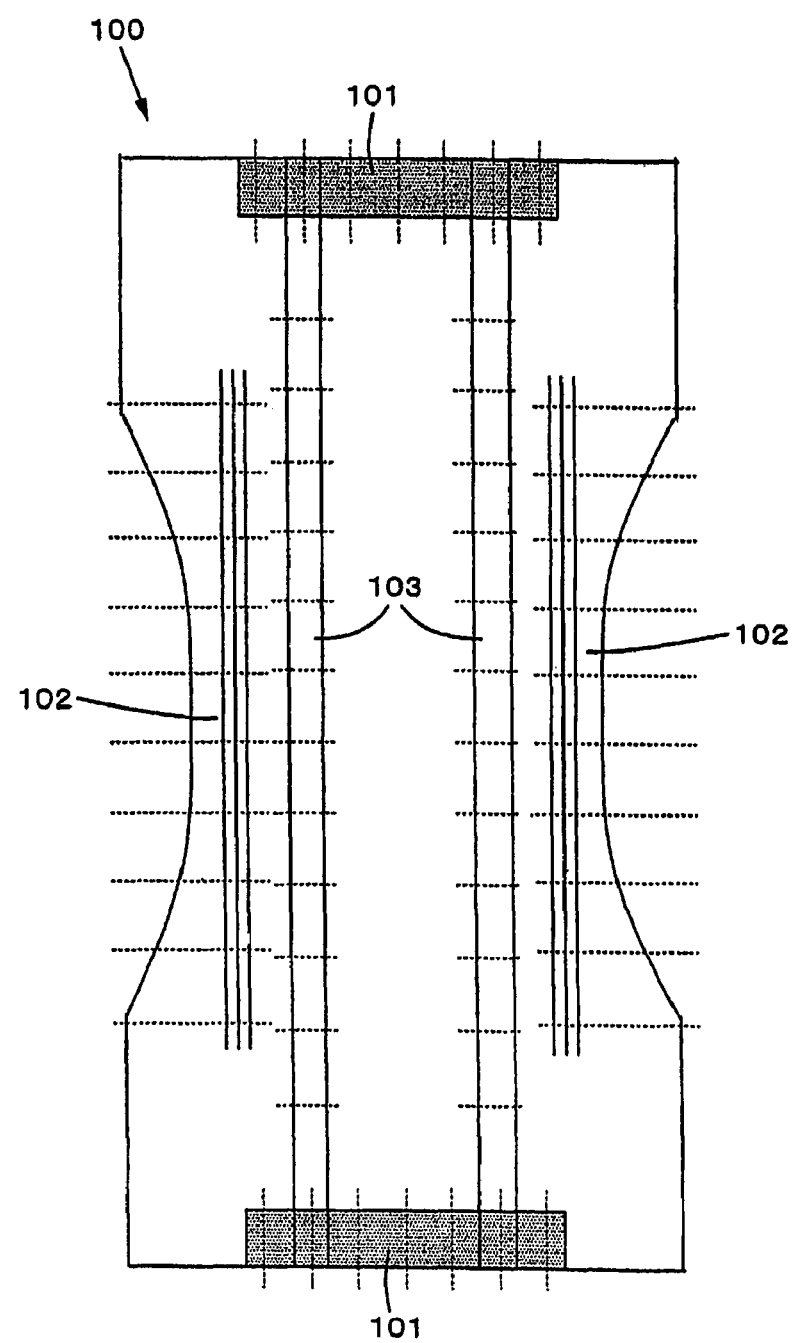
FIG. 29 is a plan view schematically showing a measuring method for the amount of absorption under pressure in a diaper state.

Next, as shown in FIG. 29, a part contracted by rubber thread in a sample diaper 100, for example, a waist part 101, a part around leg 102, a gather part 103, is notched at intervals of 2 cm as shown in a dotted line for the diaper to become flat non-forcibly (naturally).

Being use-surface (inner face) upward, the sample is inserted in flat between an acrylic plate and a metal plate, a weight (10 kg) is placed on the acrylic plate, immersed in the foregoing artificial urine maintained at 37° C. for 30 minutes.

The sample is taken out from the artificial urine after 30 minutes, after the weight and acrylic plate are removed, the sample is three-folded, placed on a scale to measure the weight.

The weight of sample after absorption is subtracted by the weight of sample before absorption to calculate the amount of absorption under pressure (g).

Measurement of Absorption Speed in Diaper State

There is used a U-shaped instrument with fill port formed in the center in the width direction at the bottom being made from U-shaped plate on the assumption of from crotch to buttock.

An absorber in a sample diaper is marked at the center position in the longitudinal direction, this marked position is fit in the fill port, and the sample is fixed in the outer face of U-shaped instrument.

The U-shaped instrument that the sample is fixed is placed on a hammock not so as to slant. A weight having a through-bore in the center (1 kg, 10 cm×10 cm) is placed on the U-shaped instrument. In this case, the through-bore of the weight is fit in the fill port of U-shaped instrument.

The foregoing urine of 100 cc is injected into the sample through the through-bore of the weight and fill port of U-shaped instrument, a time required for total absorption is measured, which is defined as an absorption speed (second).

Measurement for the Amount of Back Flow in Diaper State

A top sheet is placed on an absorber cut to 100 mm×300 mm, four sides are sealed to prepare a sample.

A cylindrical instrument of 27 mm in inner diameter (support part 150 mm×150 mm) is placed in the center of sample. The cylindrical instrument is weighted if necessary.

Artificial urine of 50 cc is dripped three times at intervals of 10 minutes.

After 10 minutes from the third dripping, filter paper (AD-VANTEC No. 2, 10 cm×10 cm, in piles of 30 pieces) is placed thereon, 5 kg of weight is loaded for 10 seconds, then, the weight of kitchen paper is measured, subtracted by the weight of kitchen paper before absorption measured beforehand to calculate the amount of artificial urine moved into kitchen paper, which is defined as an amount of back flow (g).

Measurement of Compression Resilience RC and Compression Energy WC

Using a compression tester manufactured by Kato Tech Co., Ltd. a sample is compressed in conditions: speed: 0.01 cm/sec., compression area: 2 cm2, sensitivity: 2 (pressure gauge 200 g/10 v), compression load: 50 gf/cm2, from the correlation chart between pressure and amount of deformation, compression resilience RC and compression energy WC are calculated. Larger value of compression resilience RC means higher reliance after compression, and larger value of compression energy WC means easier compression.

Sensory Evaluation of Resilience

A sample of paper diaper in a common way except for absorber was produced using each absorber. There were prepared a sample not compressed after production and one unwrapped after wrapping in a common shape under compression, resilience was evaluated through visual check and hand feeling by 20 persons being tested. The case that almost no change is felt is expressed as Δ, and the case that resilience is high and flexibility is sufficient is expressed as ○ in the evaluation as compared with the conventional example as a standard.

TABLE 7

|  |  | Example A | Conventional example B | Comparative example C |
|---|---|---|---|---|
| Super absorbent polymer | SAP used amount(g) | 11 | 11 | 12 |
| | SAP basis weight(g/cm$^2$) | 0.02 | 0.0200 | 0.0312 |
| | Absorption amount(g/g) | 60 | 53 | 54 |
| | Retention amount(g/g) | 40 | 34 | 35 |
| | Absorption speed(sec) | 40 | 45 | 75 |
| | Absorption amount under pressure(ml/g) | 33 | 33 | 31 |
| | Gel strength(Pa) | 1000 | 700 | 400 |
| Fiber aggregate | Fiber used amount(g) | 3.0 | 9.0 | 3.0 |
| | Fiber density at thickness 10 mm(g/cm$^3$) | 0.006 | 0.016 | 0.008 |
| | Fiber density at thickness 2 mm(g/cm$^3$) | 0.028 | 0.082 | 0.039 |
| | Fiber basis weight(g/cm$^2$) | 0.006 | 0.0164 | 0.0078 |
| Absorber | Absorber area(cm2) | 539 | 550 | 385 |
| | Absorber thickness(cm) | 1 | 1 | 1.1 |
| | Absorber weight(g) | 14 | 20 | 16 |
| Absorption performance in diaper state | Absorption amount under pressure(g) | 480 | 520 | 1.5 |
| | absorption speed(sec) | 450 | 238 | 1560 |
| | Back flow amount(g) | 9.0 | 7.0 | 400 |
| Compression characteristics of absorber | Compression energy WC (gf·cm/cm$^2$) | 4.0~7.0 | 2.5 | 8.1 |
| | Compression resilience RC(%) | 46 | 43 | 36 |
| | Sensory evaluation of compression resilience | ○ | — | Δ |

The present invention provides a preferable production method of absorber for absorbent article such as paper diaper, sanitary napkin, incontinence pad and absorption pad in concomitant use of diaper cover.

The invention claimed is:

1. An absorbent article comprising a body fluid permeable top sheet, a body fluid impermeable sheet, an absorber provided between the body fluid permeable top sheet and the body fluid impermeable sheet, and an exterior sheet of a nonwoven fabric provided on a back surface side of the body fluid impermeable sheet, wherein the absorber includes an absorbent core having a fiber aggregate formed by opening a tow and super absorbent polymer particle held in the fiber aggregate, and a covering sheet covering at least a backside and sides of the absorbent core;

the absorbent core has a thickness of 1-5 mm;

the fiber aggregate is made of crimped fibers having a fineness of 1 to 16 deniers and a degree of crimp of 15 to 50 pieces per one inch and has a fiber density of 0.0075 g/cm$^3$ or less, a compression energy WC based on KES test of 4.0 to 7.0 gf·cm/cm$^2$ and a compression resilience RX based on KES test of 45 to 60%;

a particle diameter of the super absorbent polymer particle is 20-850 μm;

the covering sheet is 8 to 20 g/m$^2$ in basis weight;

a basis weight of the super absorbent polymer particle in the absorbent core is 400 g/m$^2$ or less, and a weight ratio of super absorbent polymer particle/filament in a plane area of 5 cm×5 cm in a region directly receiving body fluid in the absorbent core is 3 to 9;

a holding sheet is provided between the absorbent core and the covering sheet on the back surface side of the absorbent core, the holding sheet being composed of nonwoven cloth which has a compression energy WC based on KES test of 0.01 to 10.00 gf·cm/cm$^2$ and a compression resilience RC based on KES test of 10 to 100%, and the holding sheet being applied with hot melt adhesives so that the super absorbent polymer particle is held on the holding sheet via the hot melt adhesives with super absorbent polymer particle slipped out of the fiber aggregate being prevented from moving; and the holding sheet is a non-woven fabric having a rough, face or a carded face on an upper surface thereof.

2. The absorbent article according to claim 1, wherein an upper surface of the holding sheet is a non-net face in production of non-woven fabric.

3. The absorbent article according to claim 1, wherein an upper surface of the holding sheet is processed by one selected from the group consisting of a marble treatment, needle punch processing and brushing treatment.

* * * * *